(12) United States Patent
Angenent et al.

(10) Patent No.: US 11,203,770 B2
(45) Date of Patent: *Dec. 21, 2021

(54) METHODS FOR PRODUCING CAPRYLIC ACID AND/OR CAPRYLATE

(71) Applicant: Cornell University, Ithaca, NY (US)

(72) Inventors: Largus T. Angenent, Tübingen (DE); Leo Kucek, Lake Mills, WI (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,469

(22) Filed: Jan. 6, 2020

(65) Prior Publication Data
US 2020/0283808 A1 Sep. 10, 2020

Related U.S. Application Data

(63) Continuation of application No. 15/607,188, filed on May 26, 2017, now Pat. No. 10,526,624.

(60) Provisional application No. 62/341,910, filed on May 26, 2016.

(51) Int. Cl.
*C12P 7/64* (2006.01)

(52) U.S. Cl.
CPC .................. *C12P 7/6409* (2013.01)

(58) Field of Classification Search
None
See application file for complete search history.

(56) References Cited

U.S. PATENT DOCUMENTS

| 8,956,834 B2 | 2/2015 | Roessler et al. | |
| 9,650,652 B2 * | 5/2017 | Angenent | C12M 41/26 |
| 2010/0317071 A1 | 12/2010 | Hamelers et al. | |
| 2014/0322772 A1 * | 10/2014 | Angenent | C12M 41/26 |
| | | | 435/136 |

FOREIGN PATENT DOCUMENTS

| CN | 101423471 | 5/2009 |
| CN | 101381297 | 7/2011 |
| CN | 104651440 | 5/2015 |

OTHER PUBLICATIONS

Agler et al. Energy & Environmental Science (2012), 5(8), 8189-8192 (Year: 2012).*
Steinbusch et al. Energy Environ. Sci., 2011, 4, pp. 216-224 (Year: 2011).*
Kenealy, et al., Microbiol Biotechnol. Dec. 1995; 44(3-4): 507-13. (Year: 1995).
Hu, et al. International Journal of Food Microbiology (2015), 214, 116-112 [Available online Aug. 2, 2015] (Year: 2015).
Kucek, et al., "Waste Conversion into n-Caprylate and n-Caproate: Resource Recovery from Wine Lees USing Anaerobic Reactor Microbiomes and In-line Extraction," Frontiers in Microbiology, vol. 7, Art. 1892, 14 pages Nov. 24, 2016.

* cited by examiner

*Primary Examiner* — Christian L Fronda
(74) *Attorney, Agent, or Firm* — Johnson, Marcou, Isaacs & Nix, LLC; Paul J. Roman, Jr.

(57) ABSTRACT

Methods and systems to produce product compositions comprising caprylate products using chain-elongating bacteria. For example, the caprylate product in the product composition is n-caprylic acid (C8) and the n-caprylic (C8) to n-caproic (C6) acid ratio is higher than 1:1. These methods use chain elongation towards C8 rather than C6. High n-caprylate productivity and specificity was accomplished by: 1) feeding a substrate with, for example, ethanol as the carbon source or alternatively, a high ethanol-to-acetate ratio as the carbon source; 2) extracting caprylate product(s) (e.g., n-caprylate product) from the bioreactor broth; and 3) acclimating an efficient chain-elongating microbiome. The methods can produce caprylate products such as, for example, n-caprylic acid, which is a higher value chemical than C4 and C6.

19 Claims, 32 Drawing Sheets
(32 of 32 Drawing Sheet(s) Filed in Color)

METHODS FOR PRODUCING CAPRYLIC ACID AND/OR CAPRYLATE

CROSS REFERENCE TO RELATED APPLICATIONS

This application is a continuation of U.S. Non-Provisional application Ser. No. 15/607,188, filed on May 26, 2017, which claims priority to U.S. Provisional Application No. 62/341,910, filed on May 26, 2016, the disclosures of which are incorporated herein by reference.

STATEMENT REGARDING FEDERALLY SPONSORED RESEARCH

This invention was made with government support under contract no. W911NF-12-1-0502 awarded by the U.S. Army Research Office and award no. 1336186 awarded by the National Science Foundation (SusChEM Program). The government has certain rights in the invention.

FIELD OF THE DISCLOSURE

The disclosure generally relates to biological production of caprylic acid or caprylate. More particularly the disclosure generally relates to production of caprylic acid or caprylate using a microbiome.

BACKGROUND OF THE DISCLOSURE

Ethanol as a biorefinery end product has shortcomings, including its low value and high-energy needs for extraction. Concomitantly, researchers and engineers have developed a chain-elongation platform with open cultures (reactor microbiomes) with the goal of producing medium-chain carboxylates (MCCs), such as n-caproate (C6) and n-caprylate (C8), from ethanol and short-chain carboxylates. MCCs have a higher value and are easier to extract than ethanol due to their hydrophobic characteristics when in their undissociated chemical form. The longer the chain, the more value the product will have.

Anaerobic reactor microbiomes are capable of converting organic wastes to medium chain carboxylates via a process termed reverse beta-oxidation. Generally, an electron-rich substrate, such as one containing ethanol or lactic acid, is used to drive the chain elongation of shorter chain carboxylates, such as acetate and n-butyrate, to longer chain carboxylates, such as n-caproate or n-caprylate.

Medium-chain carboxylates (MCCs, ranging from six to 12 carbons), such as n-caproate (C6), n-heptanoate (C7), and n-caprylate (C8), can be produced within the carboxylate platform by chain elongating SCCs, such as acetate (C2), propionate (C3), and n-butyrate (C4), via the reverse 3-oxidation pathway by adding two carbons during each cycle. There are a variety of different processes which result in medium chain and short chain carboxylates, but the use of bioreactors and reverse beta oxidation seems particularly promising as a sustainable platform. Reverse beta oxidation is a metabolic pathway found in prokaryotes where carboxylate chains are reduced by the addition of two carbons from a substrate, the best studied of which is probably ethanol. Since chains are elongated two carbons at a time, an acetate molecule could go to butyrate, which could go to caproate, which could go to caprylate, however this progression to caprylate does not occur or results in rather low levels. Common substrates that have been demonstrated in using reverse beta oxidation include lactate, carbohydrates, and ethanol.

*Clostridium kluyveri*, which is the type strain for the reverse β-oxidation pathway, has been well studied to ascertain the mechanistic understanding of this pathway. In several studies with microbiomes the main product has been the even-chain MCC n-caproate, while small amounts of n-caprylate have been co-produced. Reactor microbiomes have also produced the uneven-chain MCC n-heptanoate, albeit at a lower selectivity (product vs. consumed substrate) than for n-caproate production. MCCs can be utilized as antimicrobial agents in agriculture; intermediates for fragrances and flavors; and precursors for renewable diesel fuel and aviation fuel. In all of these markets, a premium is available for longer-chain products (e.g. n-caprylic acid vs. n-caproic acid) due to their increased hydrophobicity and energy density.

Until now, the literature has described chain elongation processes to work by elongating dilute ethanol and acetate into n-caproate (6-carbons; C6), but with n-caprylate as a minor component side product, if produced at all. The value of n-caprylate is about twice that of caproate on a weight basis. Since n-caprylate is considerable more valuable than n-caproate by weight, the question was raised whether mainly n-caprylate could be produced.

SUMMARY OF THE DISCLOSURE

In an aspect, the present invention provides methods of producing caprylate/caprylic acid. The methods are based on reaction of a carbon substrate (e.g., ethanol or an ethanol/acetate mixture) with a microbiome that has been acclimated to produce caprylate/caprylic acid. The methods are also based on removal of a portion of or all of the caprylate/caprylic acid during the acclimation phase and/or production phase. In an example, a method for producing a product composition comprises caprylate(s) (e.g., n-caprylic acid, n-caprylate, or a combination thereof) comprising an acclimation phase, a production phase, and, optionally, one or more selection periods.

In an example, a method for producing a product composition comprising caprylate(s) comprises an acclimation phase, a production phase, and, optionally, one or more selection periods. For example, a method comprises: providing a reaction medium comprising one or more chain-elongating bacteria species, which may be present as all of or a portion of a microbiome having a pH of 5-8; adding substrate comprising ethanol or a mixture of ethanol and acetate; holding the reaction medium at a desired temperature for a desired times during an acclimation phase until the reaction mixture produces a desired about of n-caprylic acid or n-caprylate; continuously removing at least a portion or all of the caprylic acid formed in the reaction medium during the acclimation phase, where the reaction medium is maintained at a pH of 5-8 during the holding and, optionally, continuously removing, where after the acclimation phase the reaction mixture produces a composition comprising, for example, at least 0.01% by weight caprylic acid in the reaction medium based on the total weight of the reaction medium, and continuously removing during a production phase at least a portion or all of the n-caprylic acid or n-caprylate formed in the reaction medium to form the product composition.

In another example, a method comprises: providing a reaction medium comprising an acclimated microbiome or one or more chain-elongation bacteria; holding the reaction medium at a desired temperature and maintaining the reaction medium a pH of 5-8, and continuously removing during a production phase at least a portion or all of the n-caprylic acid or n-caprylate formed in the reaction medium to form the product composition. The pH of the reaction medium can be held at 5-8 during the production phase.

Additional substrate can be added to the reaction mixture (e.g., during the acclimation phase and production phase, and, if carried out, during one or all of the selection periods). In various examples, additional substrate is added periodically added, continuously added, or a combination thereof during one of more of the periods.

A method can comprise one or more selection periods. During the selection period the amount of caprylate in the reaction mixture is allowed to increase (e.g., built up) such that microbiome constituents that cannot tolerate the increased amount of caprylate do not survive and microbiome constituents that tolerate the increased amount of caprylate (do not die) are increased in the microbiome. The resulting microbiome exhibits desirable production of caprylate. For example, a selection period comprises decreasing or stopping removal of caprylate from the reaction mixture (e.g., by decreasing or stopping extraction of caprylate from the reaction mixture).

A method can comprise a production phase. During a production phase caprylate products are formed in the reaction medium. A product composition is formed by removal (e.g., by liquid extraction) of product compounds from the reaction mixture. A product composition comprises one or more caprylate.

In an aspect, the present invention provides systems for producing caprylic acid. The systems comprise a continuous extraction system (e.g., an in-line continuous extraction system). Examples of systems include, but are not limited to, anaerobic upflow bioreactors comprising a continuous extraction system (e.g., an in-line continuous extraction system). The systems can carry out a method of the present disclosure. Examples of systems are provided herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a fuller understanding of the nature and objects of the disclosure, reference should be made to the following detailed description taken in conjunction with the accompanying figures.

were not collinear (VIF<5), but they were significant variables ($p<0.05$) that explained 88% of the variation seen in the PCoA.

Figure 7:
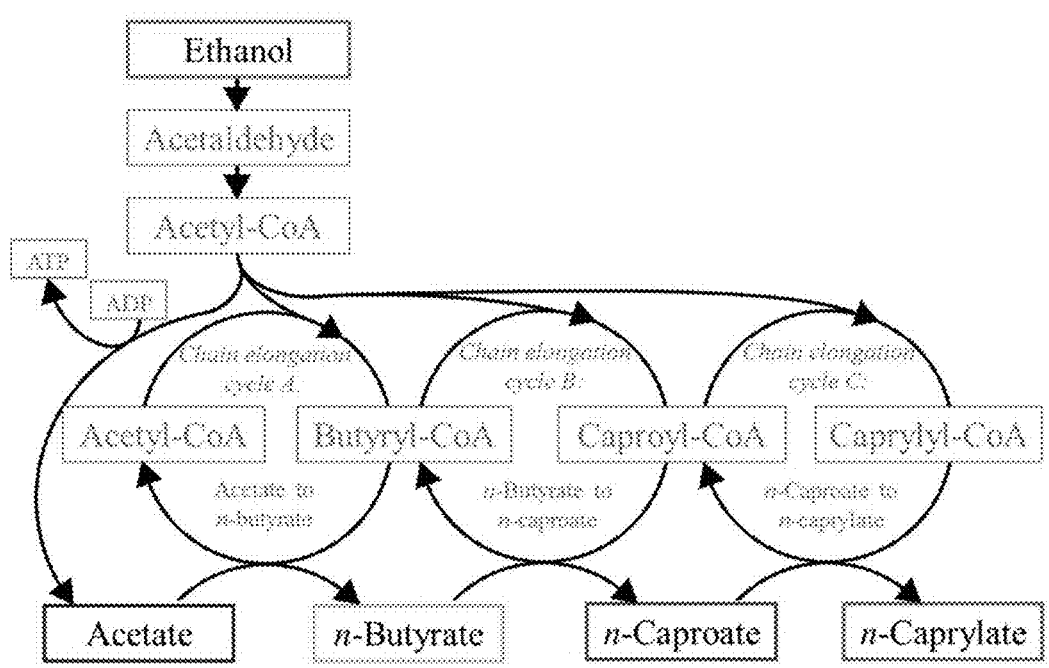

FIG. 7 shows the reverse β-oxidation pathway. With the addition of ethanol, short-chain carboxylates (e.g. acetate) can be chain elongated to medium-chain carboxylates (e.g. n-caprylate).

Figure 8:
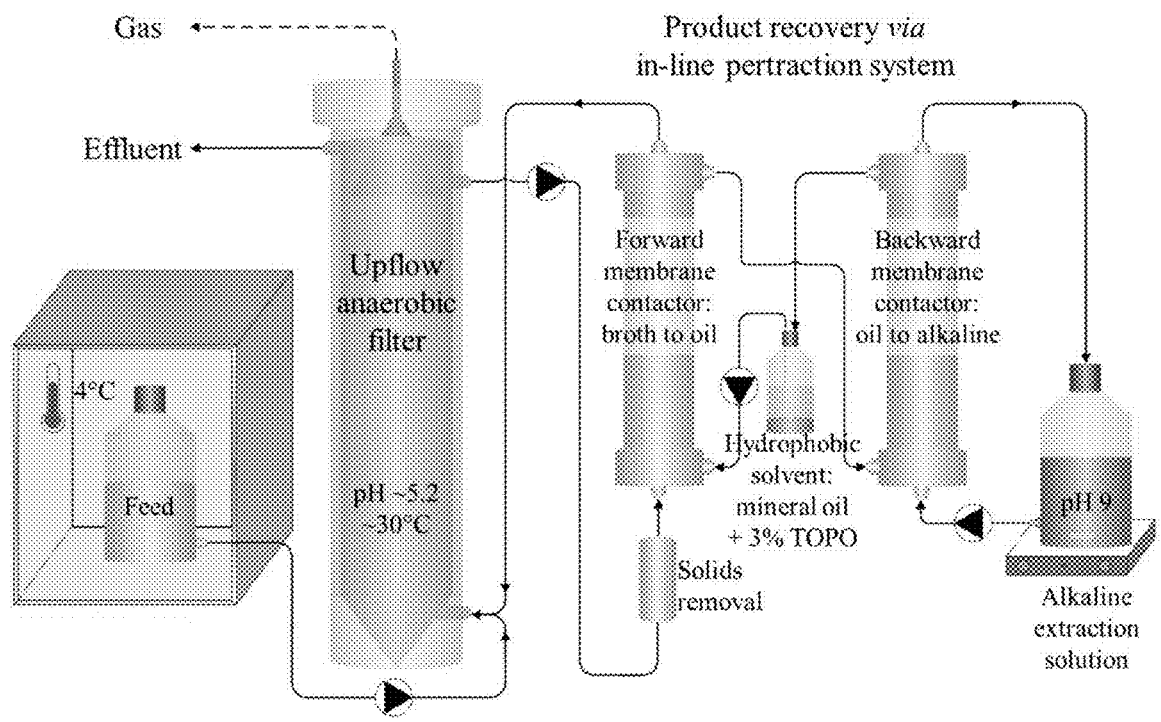

FIG. 8 shows a schematic of an example of a bioreactor system. An upflow anaerobic filter was continuously fed with ethanol and acetate. In-line product extraction was used to continuously recover hydrophobic, undissociated MCCAs from a bioreactor broth recycle flow through the forward membrane contactor. After intermediary recovery in a mineral oil solvent, MCCAs were then transferred across a second, backward membrane contactor to an alkaline extraction solution. Through automatic base addition to the alkaline extraction solution, the pH gradient was maintained, and these products accumulated in the alkaline extraction solution as MCCs.

Figure 9:
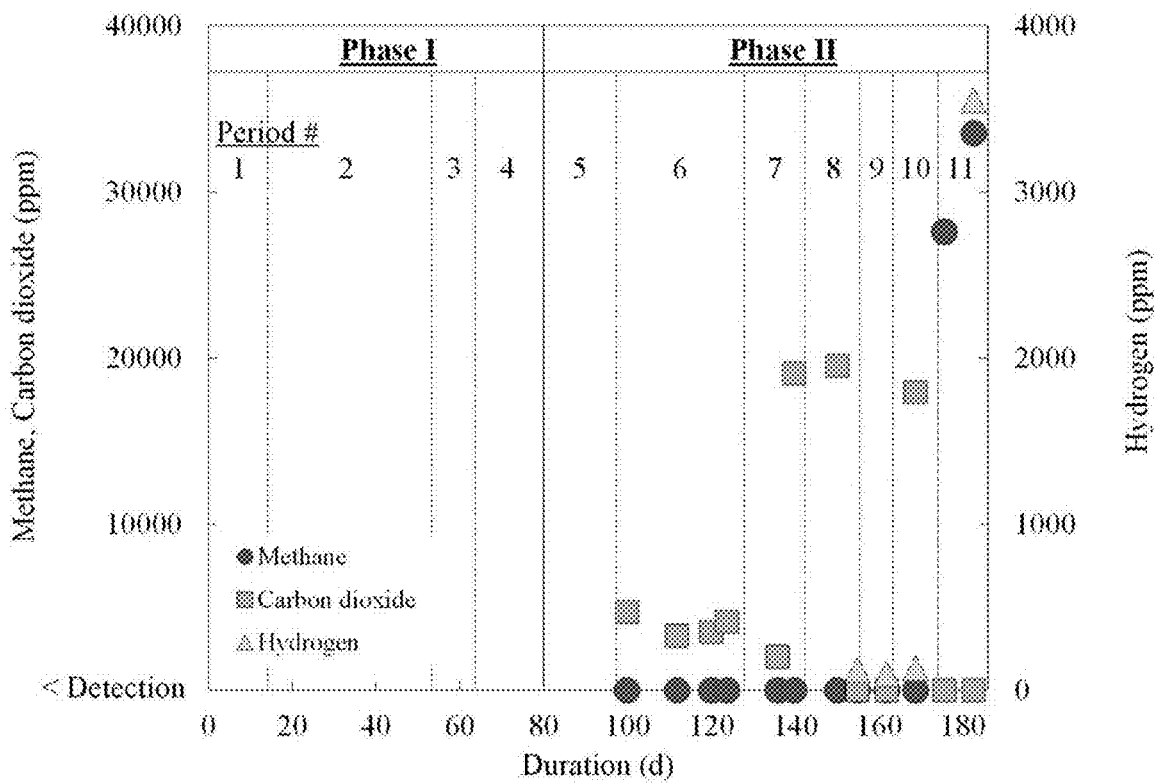

FIG. 9 shows biogas composition during Phase II. Hydrogen was quantified using the reduced gas detector at concentrations beneath 2000 ppm, while it was quantified with a gas chromatograph at higher concentrations. Methane concentrations were undetectable until Period 11 in Phase II, and the methane increase corresponded with increasing hydrogen concentrations and undetectable carbon dioxide concentrations.

Figure 10:
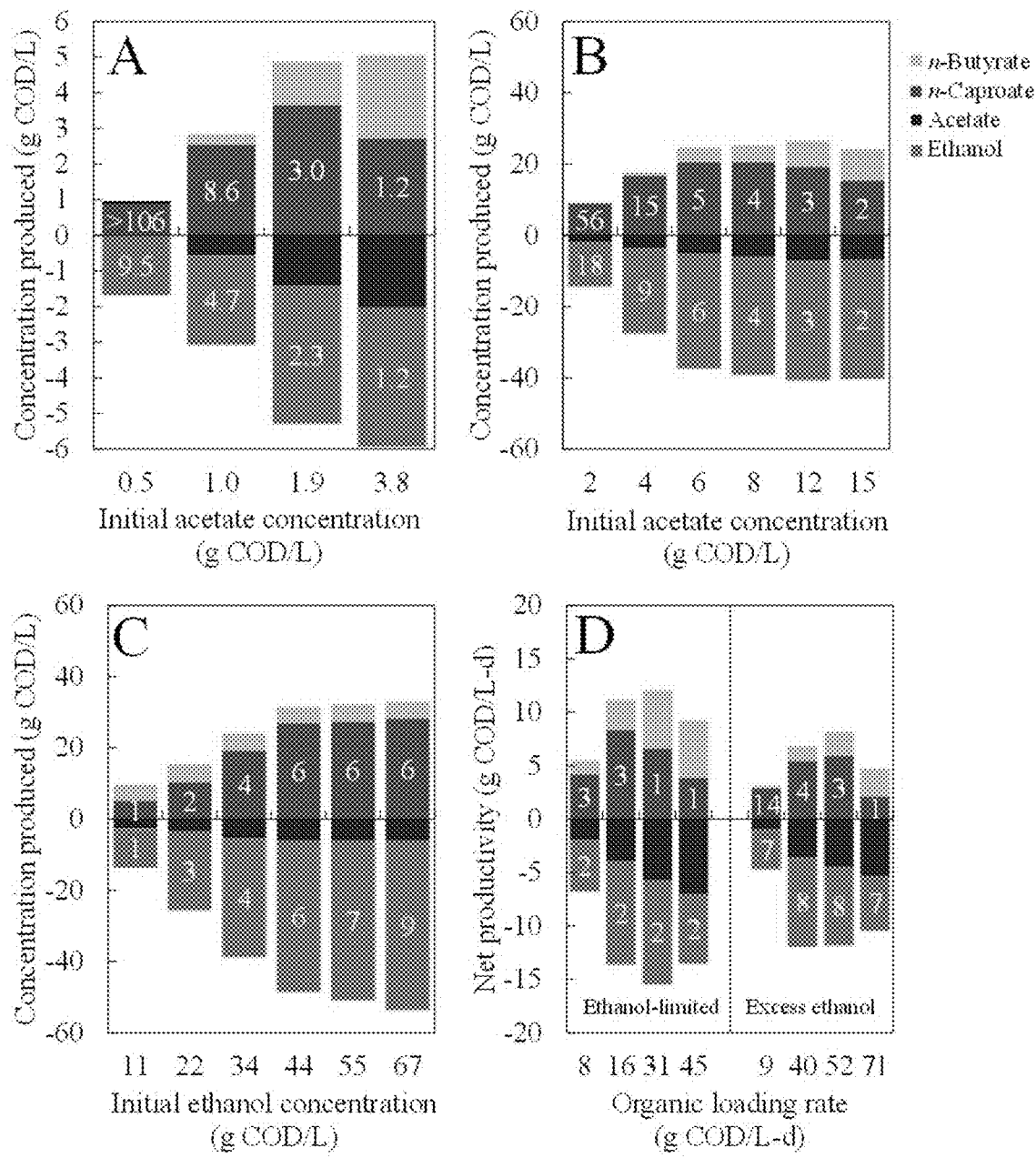

FIG. 10 shows substrate ratios and concentrations affected carboxylate product ratios and concentrations in batch and continuously fed bioreactors of *C. kluyveri*. For (A)-(C), the concentrations of ethanol and carboxylates that were either produced (positive values) or consumed (negative values) are shown for batch bioreactor experiments of *C. kluyveri*. For (D), the net volumetric production rate (productivity) of ethanol and carboxylates that were either produced (positive values) or consumed (negative values) are shown for a continuously fed bioreactor of *C. kluyveri*. In all experiments, ethanol and acetate were fed. The initial substrate ratio (ethanol to acetate) for each treatment is displayed upon the concentration of the ethanol consumed. In addition, the product ratio (n-caproate to n-butyrate) for each treatment is displayed upon the concentration of the n-caproate produced. More specifically: (A) in this batch study, the initial concentration of ethanol was fixed (4.5 g COD/L, 47 mM) and the initial concentration of acetate was varied. The bioreactor temperature was 30° C., the pH was 7, and the duration was 12 d. When the initial concentration of acetate was increased, the ratio of n-caproate to n-butyrate produced decreased. At the maximum initial concentration of acetate fed, the produced n-caproate concentration decreased; (B) in this batch study, the initial concentration of ethanol was fixed (33.6 g COD/L, 350 mM) and the initial concentration of acetate was varied. The bioreactor temperature was 39° C., the initial pH was 6.8, and the duration was 3 d. When the initial concentration of acetate was increased, the ratio of n-caproate to n-butyrate produced decreased. At the maximum initial concentration of acetate fed, the produced n-caproate concentration decreased; (C) in this batch study, the initial concentration of acetate was fixed (7.7 g COD/L, 120 mM) and the initial concentration of ethanol was varied. The bioreactor temperature was 39° C., the initial pH was 6.8, and the duration was 3 d. When the initial concentration of ethanol was increased, the ratio of n-caproate to n-butyrate produced increased until the initial concentration of ethanol was 44 g COD/L (460 mM); higher initial levels of ethanol led to substrate inhibition and decreased ethanol utilization; and (D) in this continuously fed bioreactor study, the substrate ratio of ethanol to acetate was either ethanol-limited or had excess ethanol (2 or ~7 g COD/g COD, respectively, which is 1.04 or ~3.63, respectively, by weight [divided by 1.927]). Increased substrate ratios and decreased substrate concentrations led to increased product ratios.

Figure 11:
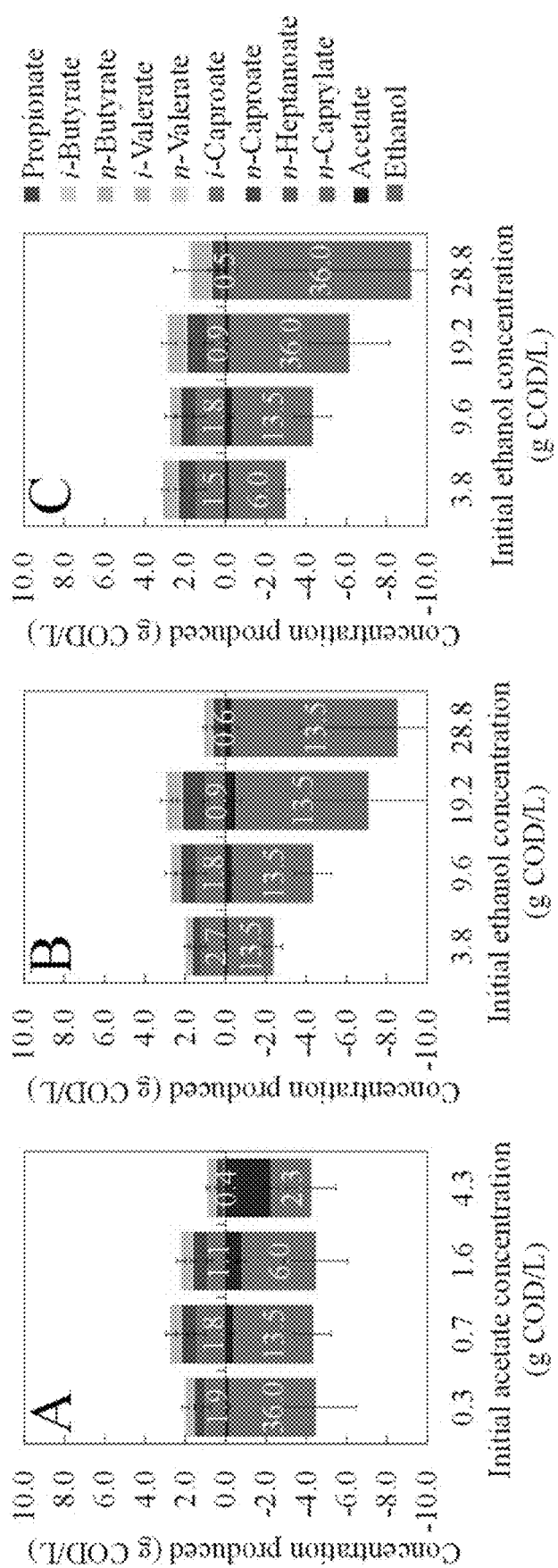

FIG. 11 shows substrate ratios and ethanol concentrations affected MCC product ratios and concentrations in batch reactor microbiomes. The concentrations of carboxylates that were either produced (positive values) and the ethanol and acetate that were consumed (negative values) are shown for three batch experiments with reactor microbiomes that we performed. In all experiments, ethanol and acetate were fed, and each concentration represents the average of triplicate biological batch bottles. The temperature of the bioreactors was controlled at 30° C. and the initial pH was set at approximately 5.4 with an experimental period of 12 d. The initial substrate ratio (ethanol to acetate) for each treatment is displayed in white font within the pink bar for the ethanol concentration consumed, while the product ratio (n-caprylate to n-caproate) for each treatment is displayed in white font in the center of the green bar for the n-caprylate concentration produced. More specifically: (A) the initial concentration of ethanol was fixed (9.6 g COD/L, 100 mM) and the initial concentration of acetate was varied. When the initial concentration of acetate was increased (which consequently decreased the initial substrate ratio of ethanol to acetate), the product ratio of n-caprylate to n-caproate decreased. Increased substrate ratios of ethanol to acetate led to increased n-caprylate product ratios; (B) the initial substrate ratio of ethanol to acetate was fixed (13.5 g COD/g COD [7.0 by weight]) and the substrate levels were varied. At this fixed substrate ratio, the lower substrate concentrations resulted in the higher product ratios of n-caprylate to n-caproate, as well as the higher concentrations of n-caprylate. At initial ethanol concentrations of 28.8 g COD/L (300 mM), considerable substrate inhibition of medium-chain carboxylate production was observed; and (C) the initial acetate concentration was fixed (~0.7 g COD/L, ~10 mM) and the initial concentrations of ethanol were varied. An initial concentration of ethanol of 28.8 g COD/L (300 mM) led to substrate inhibition of chain elongation, even with fixed acetate concentrations.

Figure 12:
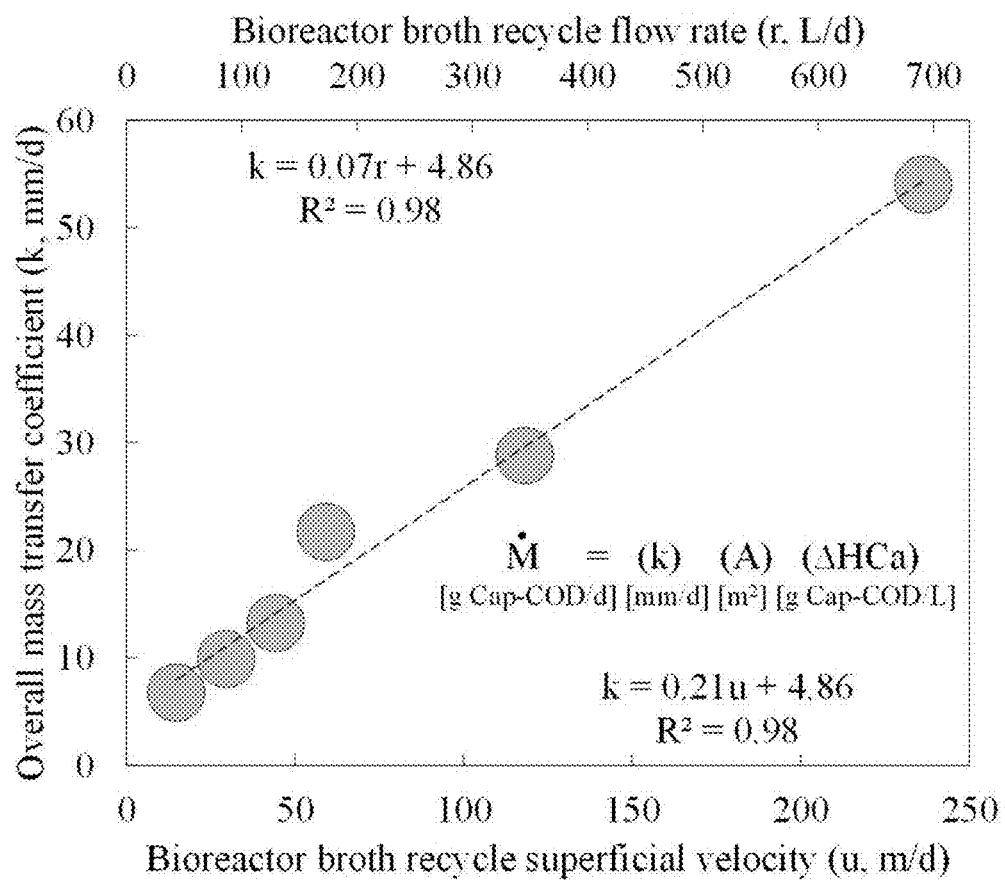

FIG. 12 shows an example where the overall mass transfer coefficient was directly proportional to the abiotic reactor broth recycle flow rate. During an abiotic n-caproate transfer experiment that used a similar pertraction system (same materials, but a different size of contactors) than this bioreactor experiment, we determined that the overall mass transfer coefficient (k) was directly proportional to the reactor broth recycle flow rate (r). Each of the contactors can be compared when corrected for the superficial velocity (u). Increasing the recycle flow rates of mineral oil solvent or the alkaline extraction solution did not affect mass transfer rates, indicating that mass transfer limitations were at the interface of the reactor broth and the hydrophobic membrane contactor. The overall mass transfer coefficient was linearly correlated to the reactor broth recycle flow rate through the highest flow rates that the pumps could provide (690 L/d). During the continuously fed bioreactor experiment, however, we maintained a constant recycle flow rate (r), mass transfer coefficient (k), and membrane surface area (A). With these fixed values fixed, improvements in MCC transfer and production rates could only be achieved by higher concentrations of undissociated medium-chain carboxylic acids (MCCAs) in the bioreactor broth. The data here shows that we could have increased the MCC transfer rates with the same membrane contactors if we had increased the bioreactor broth recycle flow (but we did not increase it).

Figure 13:
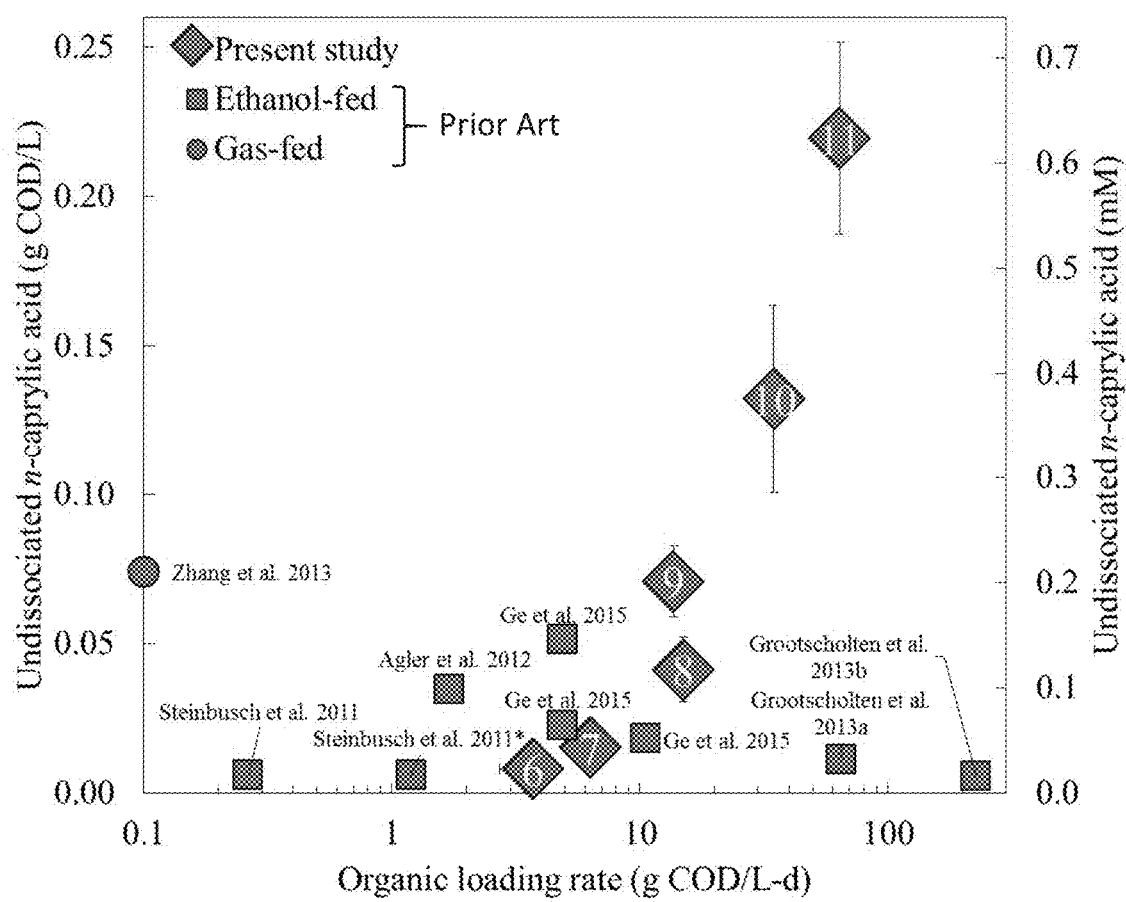

FIG. 13 shows undissociated n-caprylic acid concentrations from examples of bioreactors with ethanol as an electron donor, including Phase II. Results from previously published studies in which n-caprylate production was reported are shown. Also shown are results from this Example (large squares). Operating periods from Phase II of this Example are labeled with a white font. Maximum instantaneous values reported are indicated (*). Organic loading rates are presented on logarithmic scales. One study produced n-caprylate in a bioreactor in which gas composed of carbon dioxide and hydrogen was fed; they did not report OLRs, so this marker was placed at an OLR near the sum of the total carboxylate volumetric production rates. The highest concentration of undissociated n-caprylic acid concentrations during Period 11 of our Example likely led to product inhibition.

Figure 14:
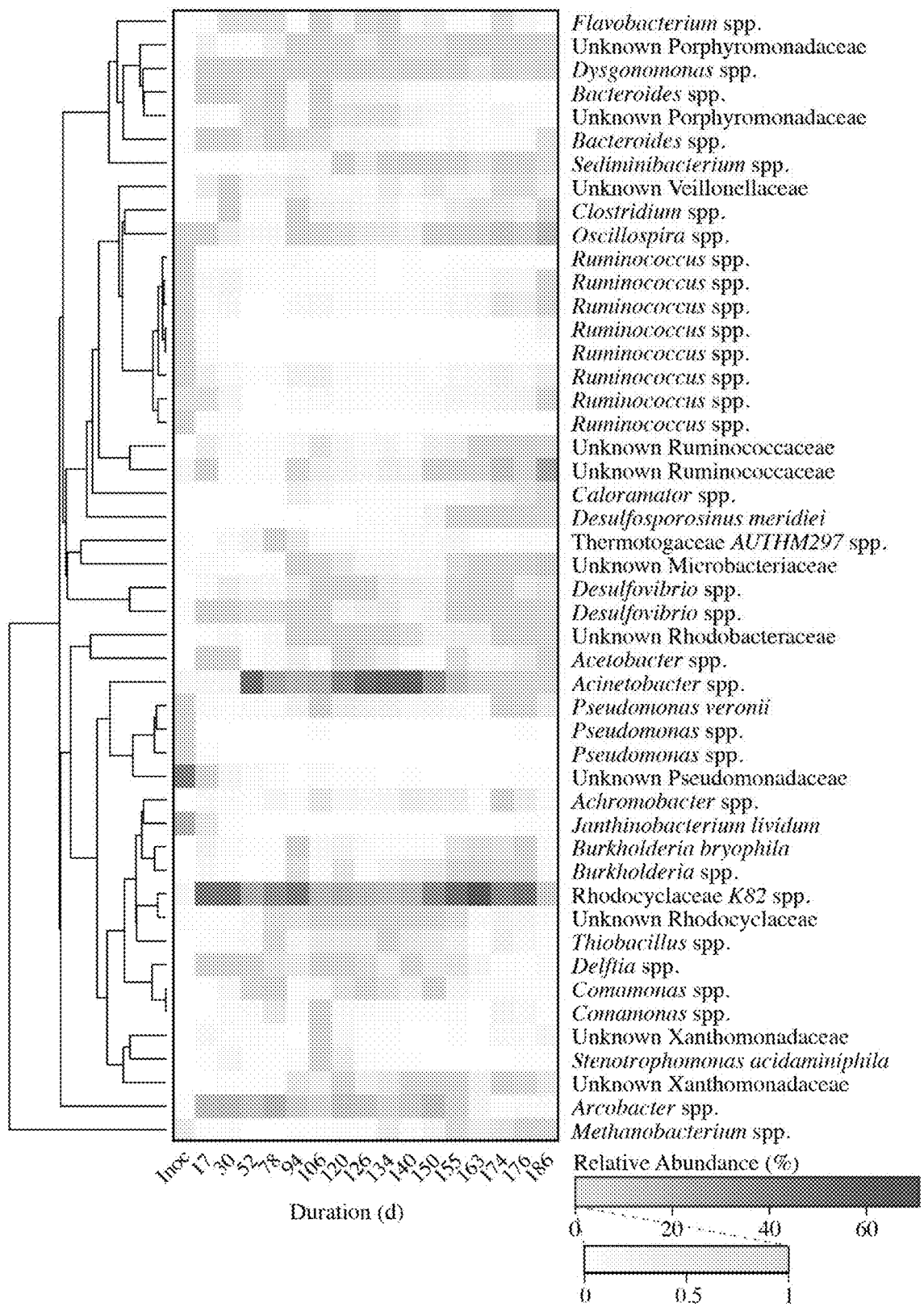

FIG. 14 shows 48 OTUs with a relative abundance that exceeded 1% of at least one microbiome sample during the entire operating period. Relative abundances of operational taxonomic units (OTUs) varied during the operating period. Dominant OTUs included Rhodocyclaceae K82 spp. and *Acinetobacter* spp., which comprised up to 70.8 and 55.5% of the relative abundance, respectively. Phylogenetic similarity is indicated.

Figure 15:
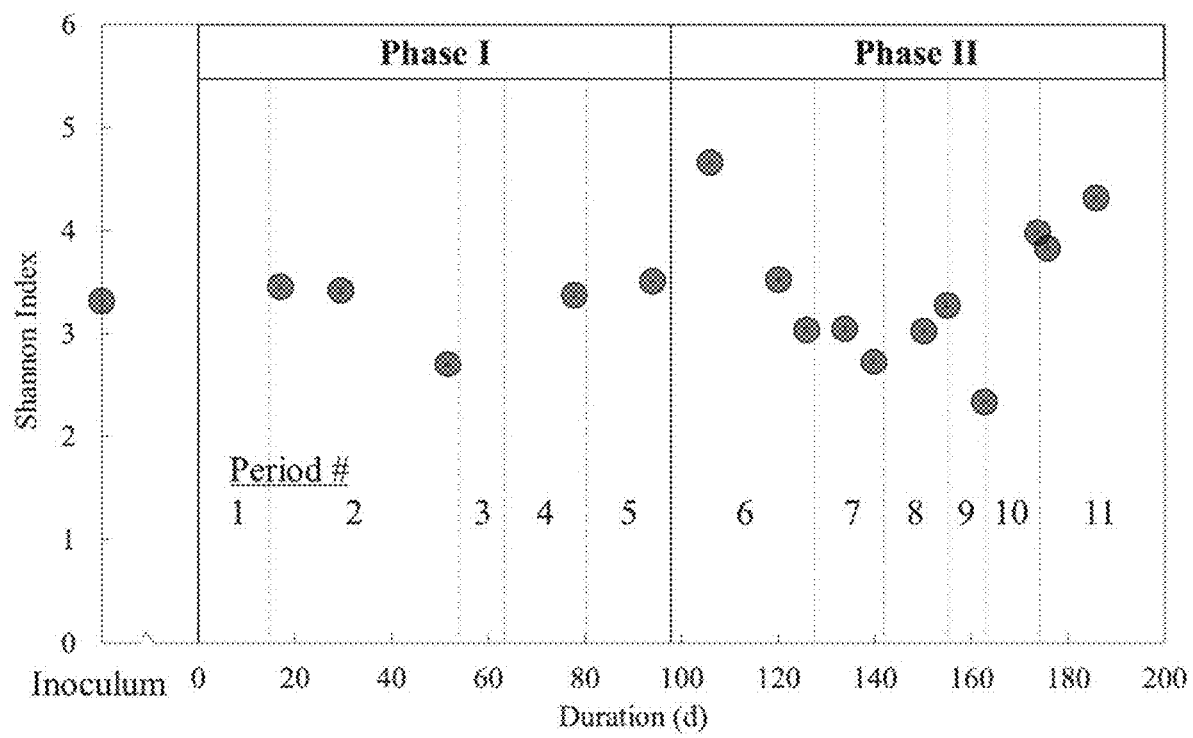

FIG. 15 shows alpha diversity of reactor microbiome sample during the operating period. The Shannon index was used to determine the evenness and richness for the 16 reactor microbiome samples that we collected, including the inoculum. Uncertainty is represented by 95% confidence intervals based on ten independent rarefactions.

Figure 16:
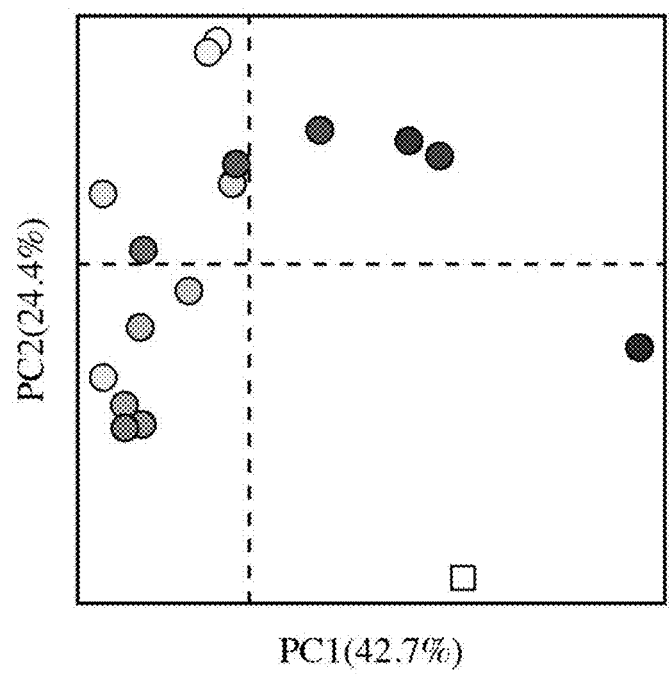

FIG. 16 shows beta diversity of reactor microbiome samples during an entire operating period. Principal coordinates analysis (PCoA) was used to determine the dissimilarity between microbiome samples taken based on the weighted UniFrac metric. The first two principal coordinate (PC) axes are shown. PC1 explains 43% of the overall phylogenetic variation, while PC2 explains 24%. The increasing blue color of the circles for the 16 bioreactor samples indicates the increasing length for the operating period when the sample was taken, including Day 17, 30, 52, 78, 94, 106, 120, 126, 134, 140, 150, 155, 163, 174, 176, and 186. The white square represents the inoculum.

Figure 17:
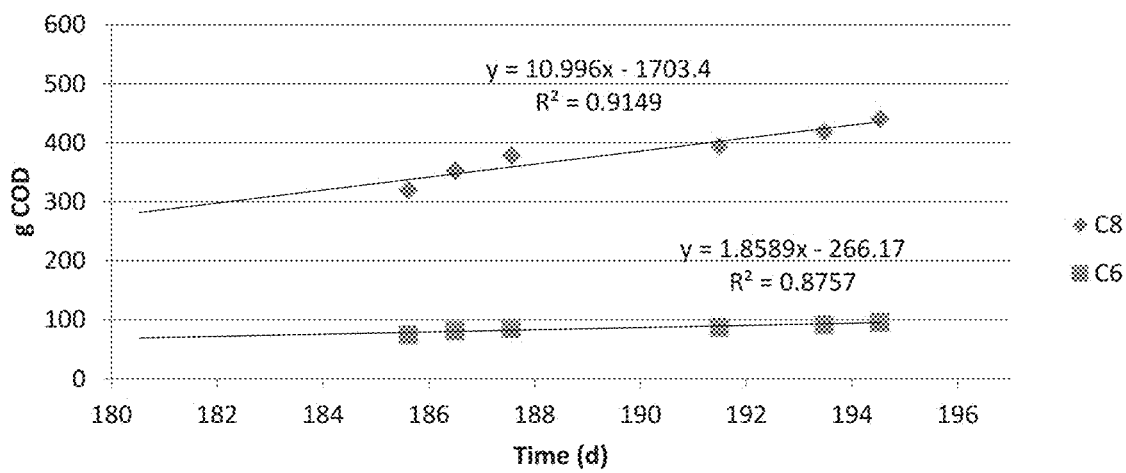

FIG. 17 shows accumulation of medium chain carboxylates (MCCs) in the stripping solution overtime at the fixed ethanol to acetate molar feed ratio of 10:1 (12.8:1 by weight). C8 is caprylate and C6 is caproate. This ratio gave the highest transfer and overall production rates of MCCs for the entire Example.

Figure 18:
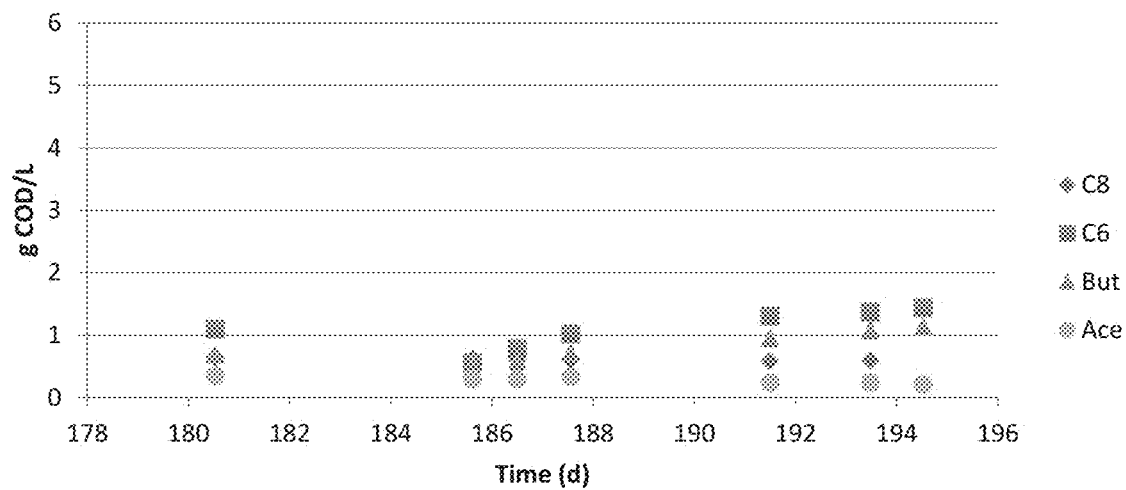

FIG. 18 shows the concentrations of various carboxylates (in g COD/L) of the reactor effluent over the course of the 10:1 molar feed ratio (12.8:1 by weight).

Figure 19:
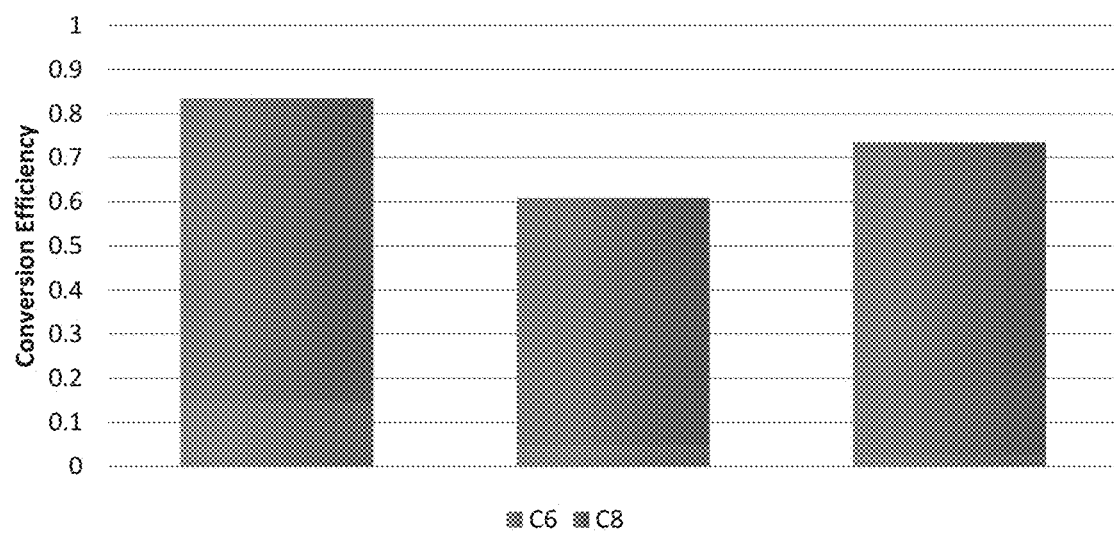

FIG. 19 compares the conversion efficiencies of the 10:1 molar ethanol to acetate feed ratio (12.8:1 by weight) in three experiments. Overall conversion of both caproate and caprylate is higher in the left replicant, however the ratio of caprylate to caproate is higher in the two right replicants. The hydraulic retention time (HRT) for each trial varies. The HRT of the left replicant was 1.32±0.10 days (a 95% confidence interval), whereas the other HRTs were 1.5 days and 3.3 days respectively. Error bars are not displayed in this figure, though can be found in FIG. 25. Order of data within the bars: Top (C8), bottom (C6)

Figure 20:
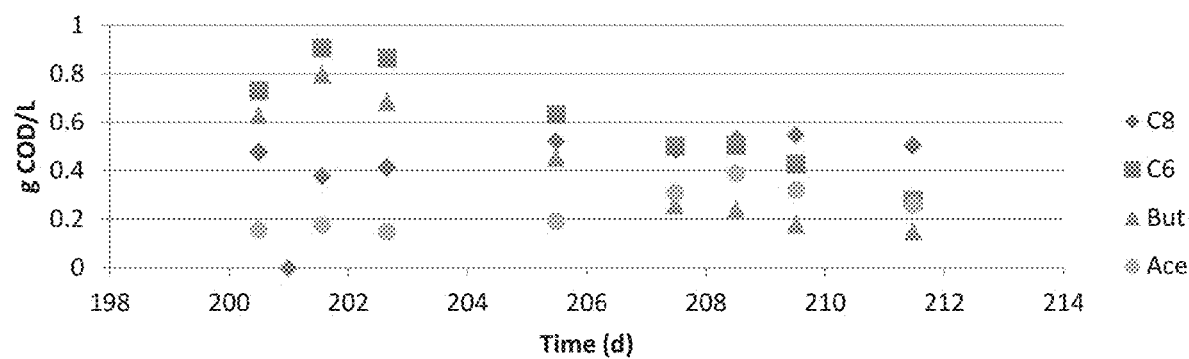

FIG. 20 shows effluent concentrations of different carboxylates over time from a 10:0, pure ethanol, feed.

Figure 21:
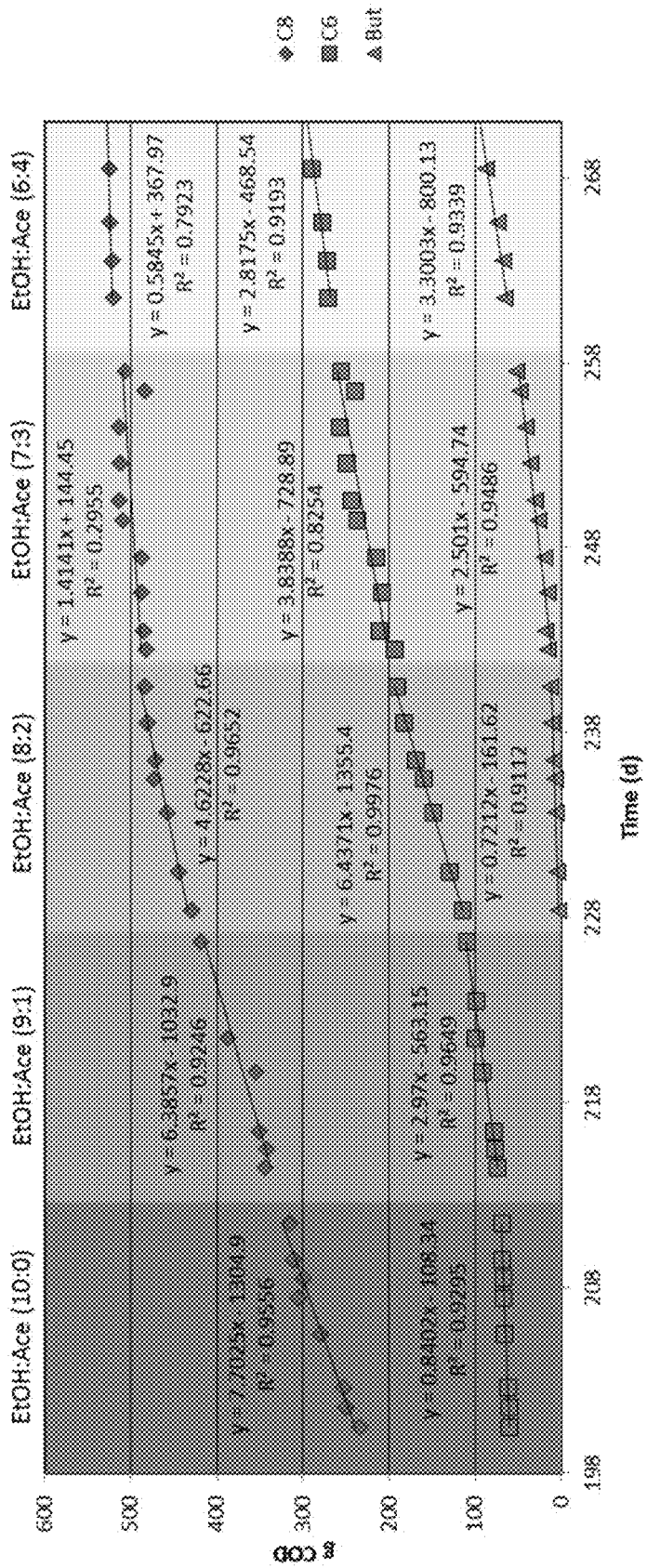

FIG. 21 shows total carboxylates found in the stripping solution over time for the different the ethanol to acetate ratios tested in the feed. Each color change represents the change in feed ratios in descending order, starting from 10:0 and going to the beginning of the 6:4 run. As can be seen clearly in figure, there are quite noticeable changes in slope (a function of the transfer rate) over time. Initially, at the ten to zero ethanol to acetate ratio, a majority of the carboxylates accumulating in the feed are caprylate (indicated by C8). As the ratios go down, so too does the transfer rate of caprylate. From the 8:2 ratio onwards, butyrate (But) started to be detected by the GC, and as the ratios decrease the transfer rate of butyrate goes up. The caproate (C6) slope initially increases and then decreases as the ratio of ethanol to acetate decreases further. By 6:4, acetate started to be found in the stripping solution in low concentrations (not plotted). At the time of this paper, only 4 data points for 6:4 have been run in the GC.

Figure 22:
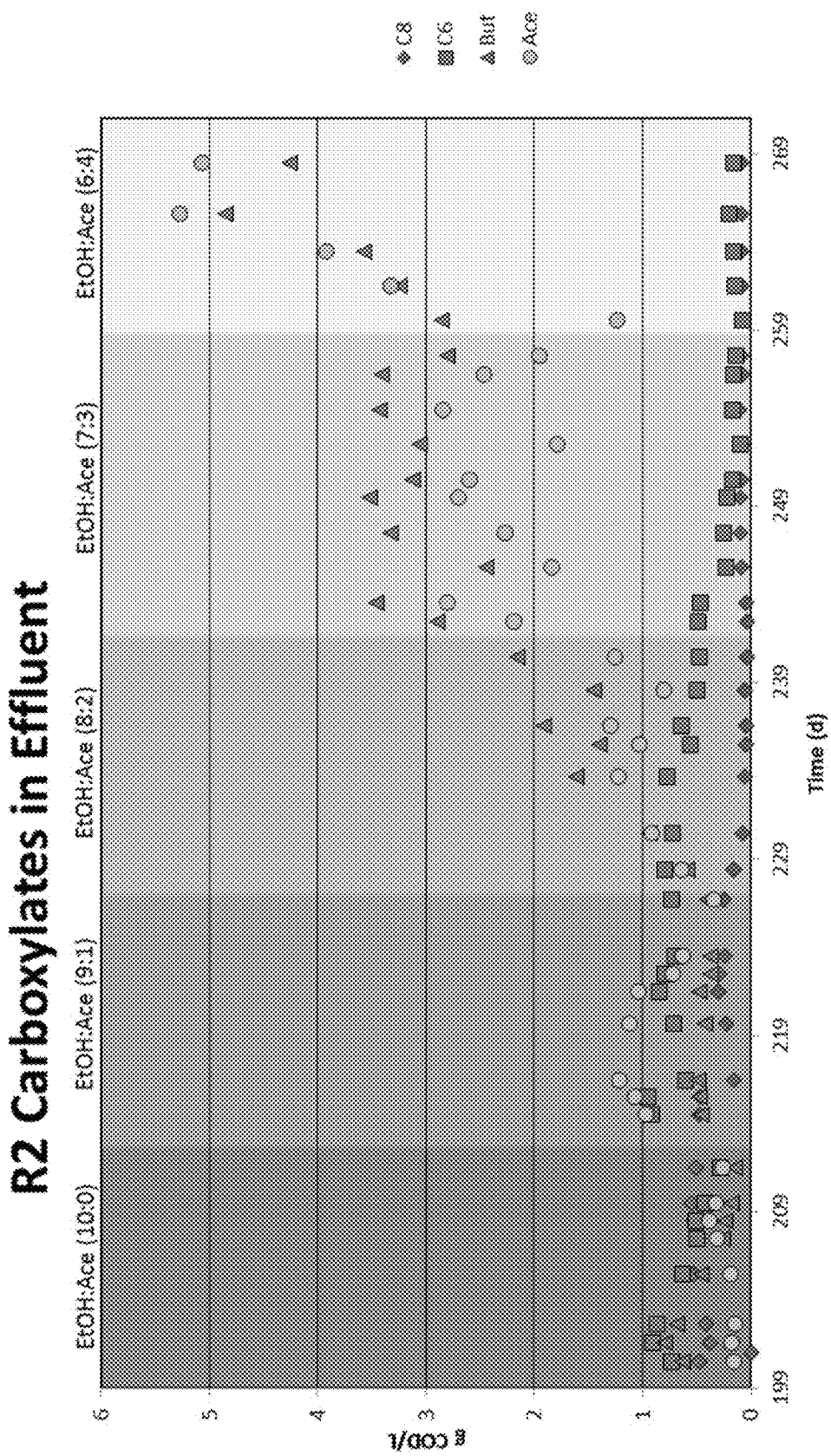

FIG. 22 shows concentration of carboxylates found in examples of effluent in gCOD/L. Each color change corresponds to a change in the influent molar ratio of ethanol to acetate. To find the effluent rates, the averages of each carboxylate were taken over the course for each respective feed ratio and divided by the hydraulic retention times of each phase. General trends in this figure show that as the ethanol to acetate feed ratio decreases, the concentration of the MCCs in the reactor goes down as the concentration of short chain carboxylates (butyrate and acetate) goes up.

Figure 23:
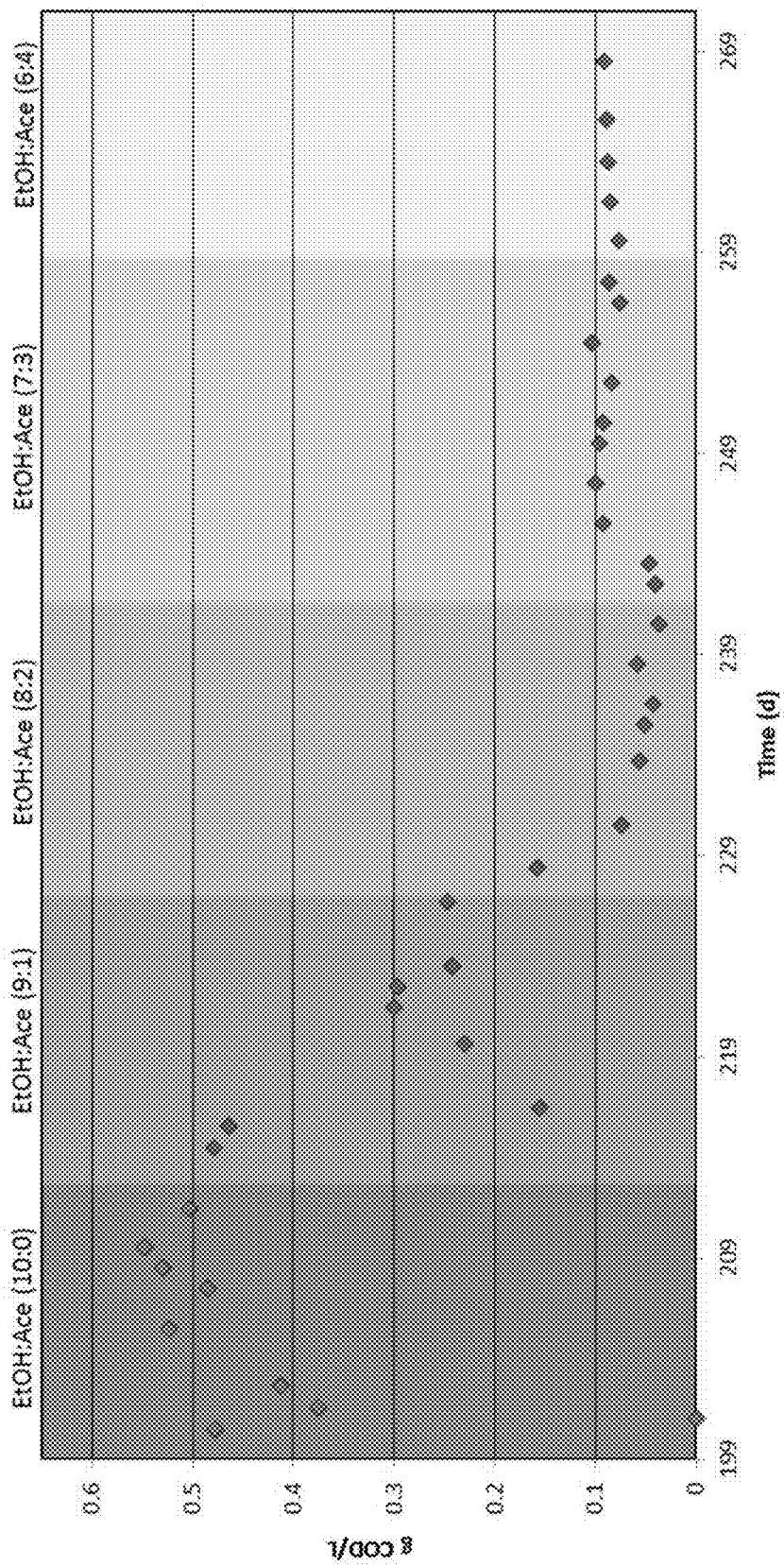

FIG. 23 shows using the same data as that found in FIG. 23, however caprylate is isolated and the y-axis is rescaled to clearly show the caprylate ratios in gCOD/L in the reactor broth.

Figure 24:
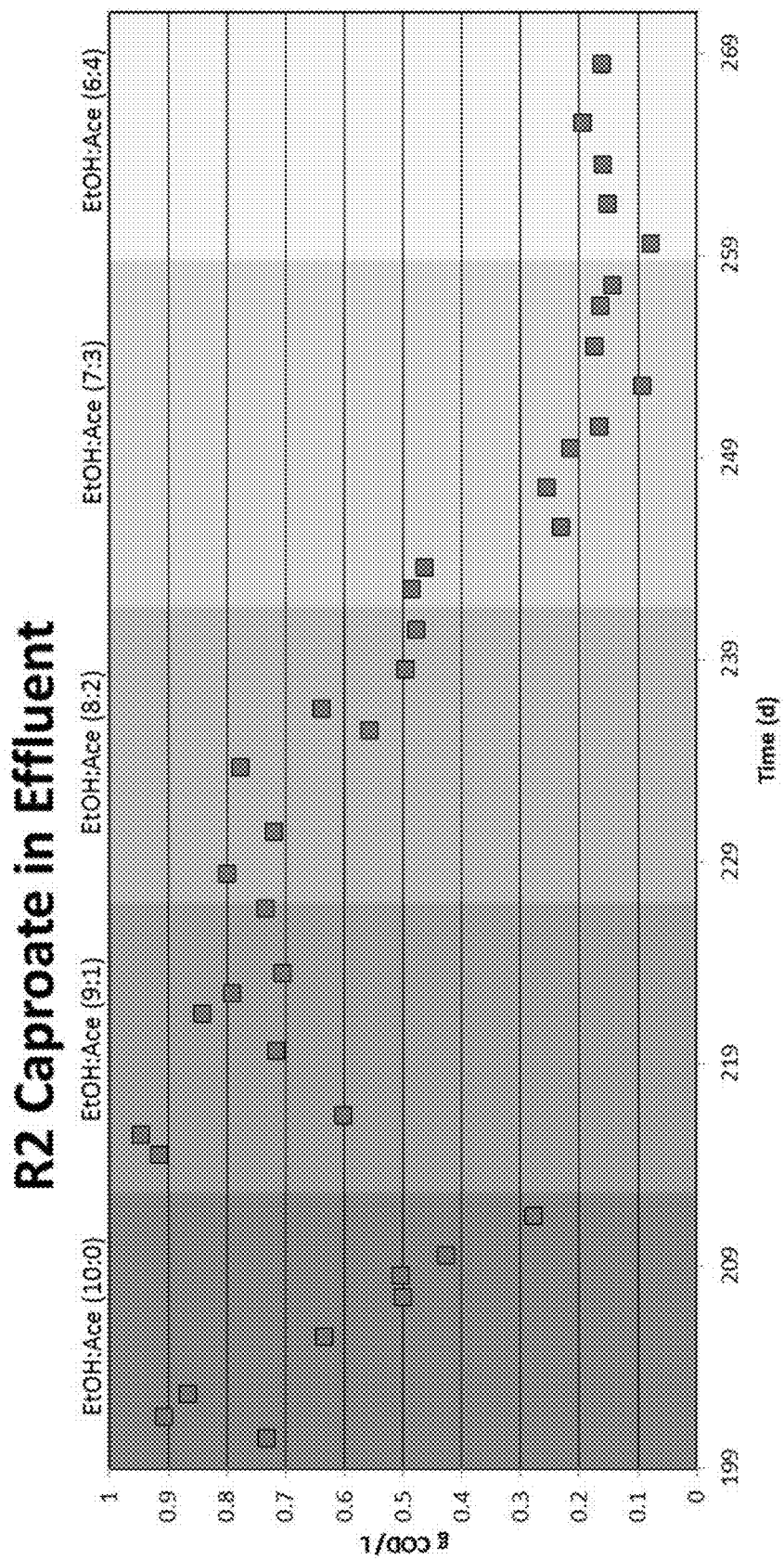

FIG. 24 shows using the same data as that found in FIG. 23, however caproate is isolated and the y-axis is rescaled to clearly show the caproate ratios in gCOD/L in the reactor broth. Of note is the decrease of caproate during the pure ethanol run (leftmost of the figure).

Figure 25:
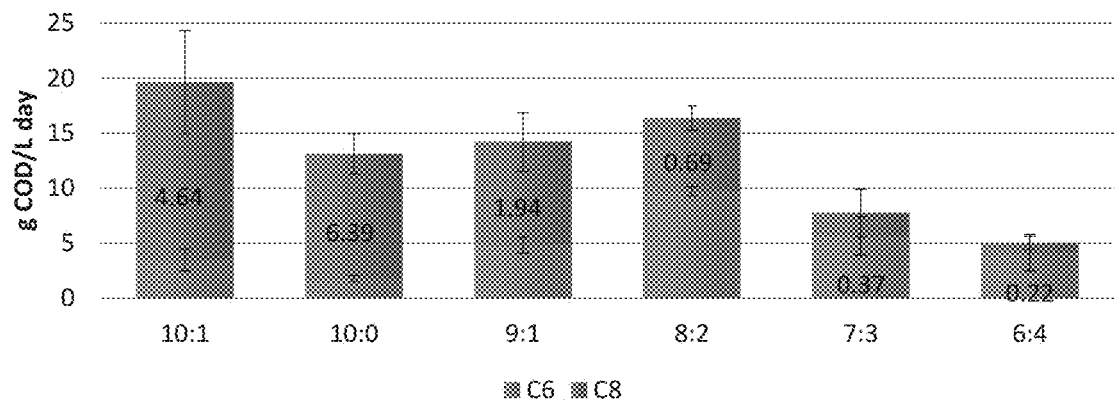

FIG. 25 shows productions rates of only the MCCs for different molar feed ratios. The error bars represent the 95% confidence intervals. The numbers in each of the bars are the ratios of caprylate production rates to caproate production rates. The organic loading rate for each period is approximately 25 gCOD/L-day. The overall production of MCCs was highest after the initial period at 8:2 ethanol to acetate, though the ratio of caprylate to caproate continues to decrease throughout the trials. Order of data within the bars: Top (C8), bottom (C6).

Figure 26:
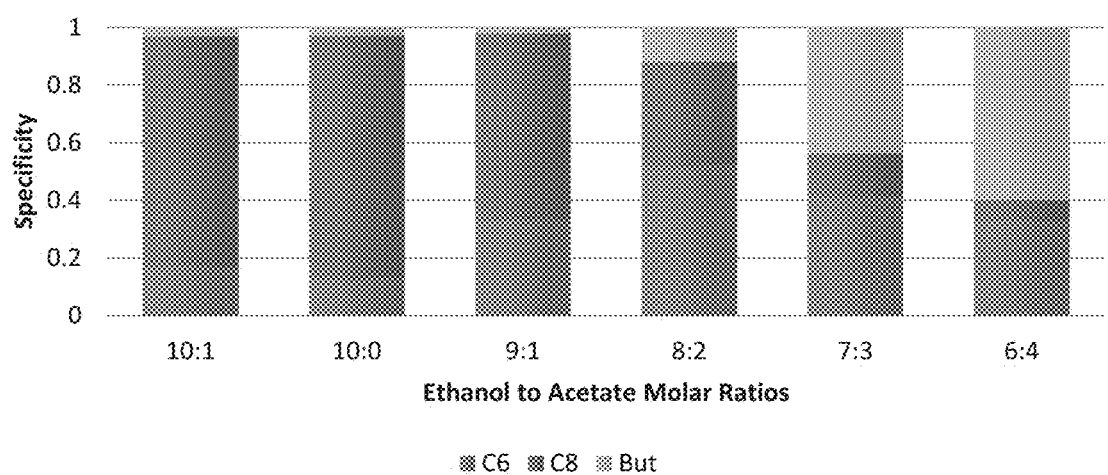

FIG. 26 shows specificities of each of the major carboxylates produced by the reactor. Absent is acetate and odd numbered carbon carboxylates, the latter of which was not found consistently in the stripping or effluent. The trend of increasing butyrate, decreasing caprylate, and increasing then decreasing caproate can be seen again. Order of data within the bars: Top (butyrate), middle (C8), bottom (C6).

Figure 27:
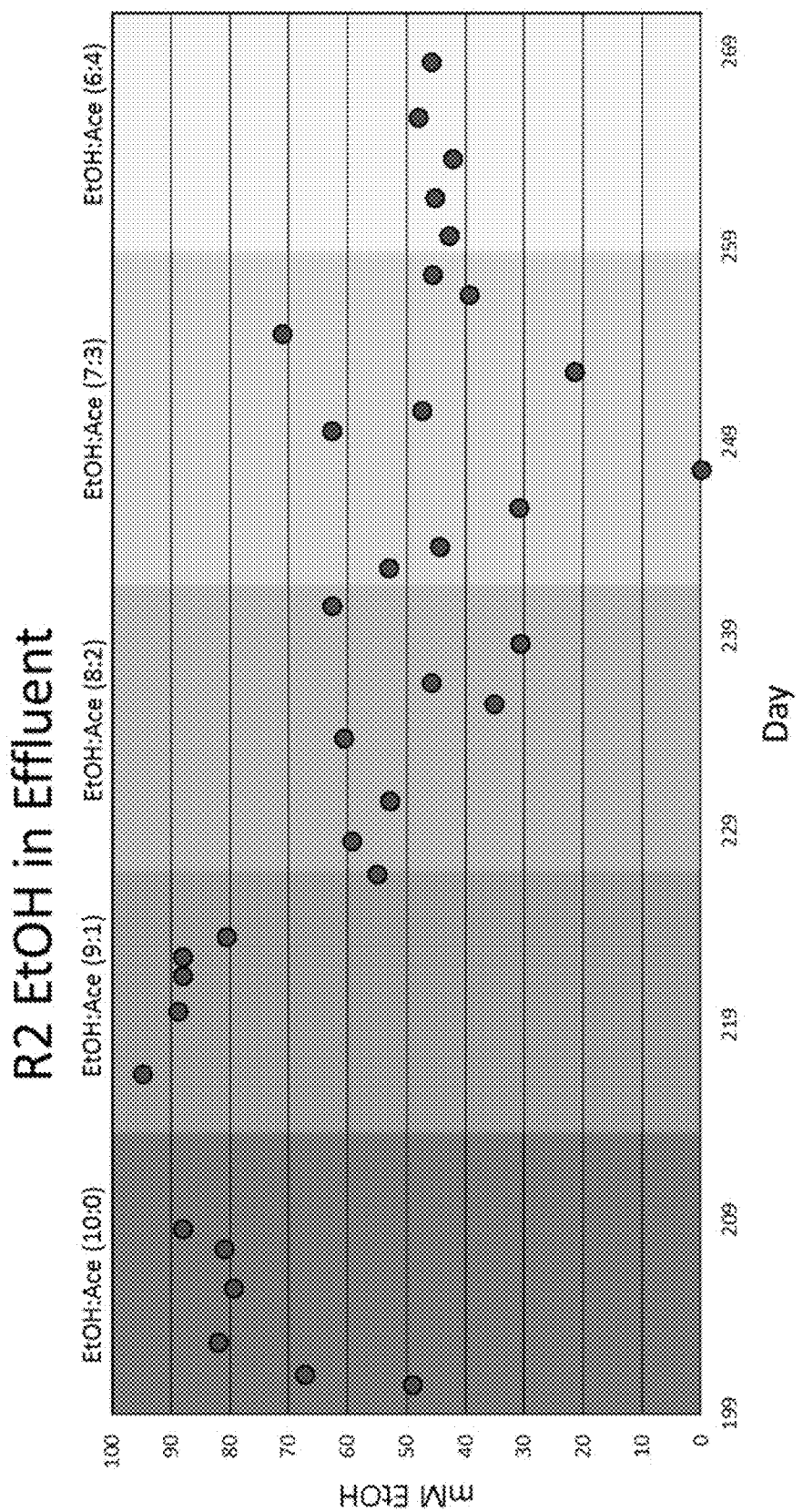

FIG. 27 shows concentration of ethanol in the reactor broth over time and influent molar ratios. It should be noted that this scale is in molar terms as opposed to gCOD/L. It should also be noted that there is a considerable gap between the last data point of the pure ethanol trial and the 9:1 trial. This is due to missing data that should be filled in at a later date. The overall trend shows a dramatic increase in ethanol concentration during the pure ethanol phase which then steadily decreases in subsequent periods of lower ethanol to acetate feed ratios.

Figure 28:
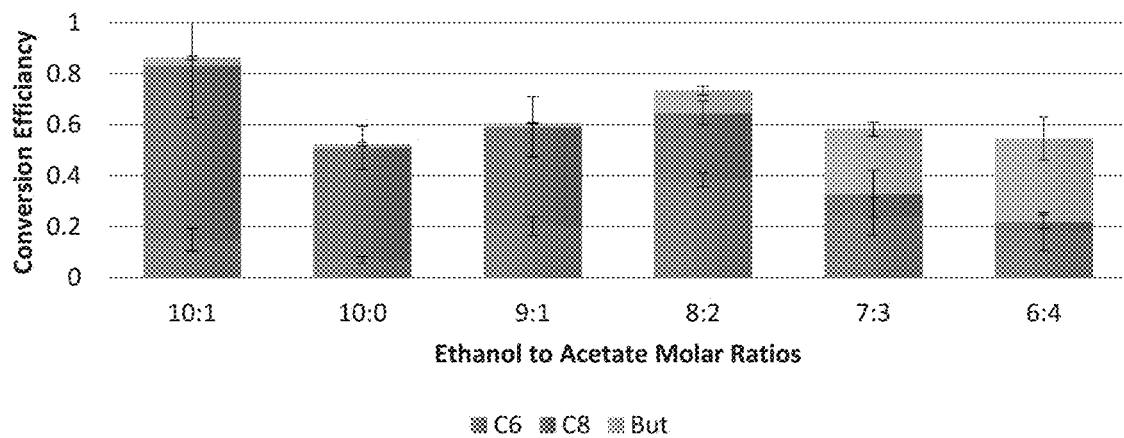

FIG. 28 shows conversion efficiencies of each of the major products of the bioreactor for the different trials. Conversion efficiency is the ratio of the production rate of each carboxylate over the organic loading rate of the feed. The error bars in the figure represent 95% confidence intervals. At higher ethanol to acetate ratios, caprylate conversion is larger than caproate and butyrate conversion. As the influent ratio decreases, the total conversion increases, but caprylate conversion goes down. Butyrate conversion goes up, and caproate production first increases and then decreases. Order of data within the bars: Top (butyrate), middle (C8), bottom (C6).

Figure 29:
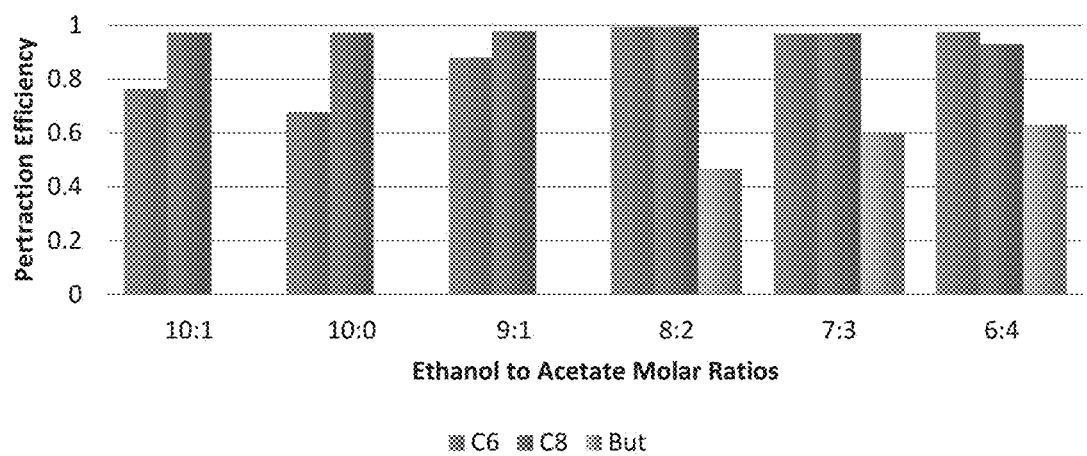

FIG. 29 shows the pertraction efficiencies of carboxylates at varying feed ratios and over time. The pertraction efficiency is the fraction of the total production rate that is accounted for by the transfer rate. In this sense it is a measure of the efficiency of the stripping system. The pertraction efficiency for caprylate remains over 95% for all but the last period. The high efficiency implies that the production rate is not limited by the mass transfer of MCCs into the stripping, especially for caprylate. The figure also shows that the pertraction efficiency of caproate and butyrate increases with lower ethanol to acetate feed ratios. Order of bars left to right: Left (C6), middle (C8), right (butyrate). Butyrate not produced in 10:1, 10:0 and 9:1 (these are molar ratios).

Figure 30:
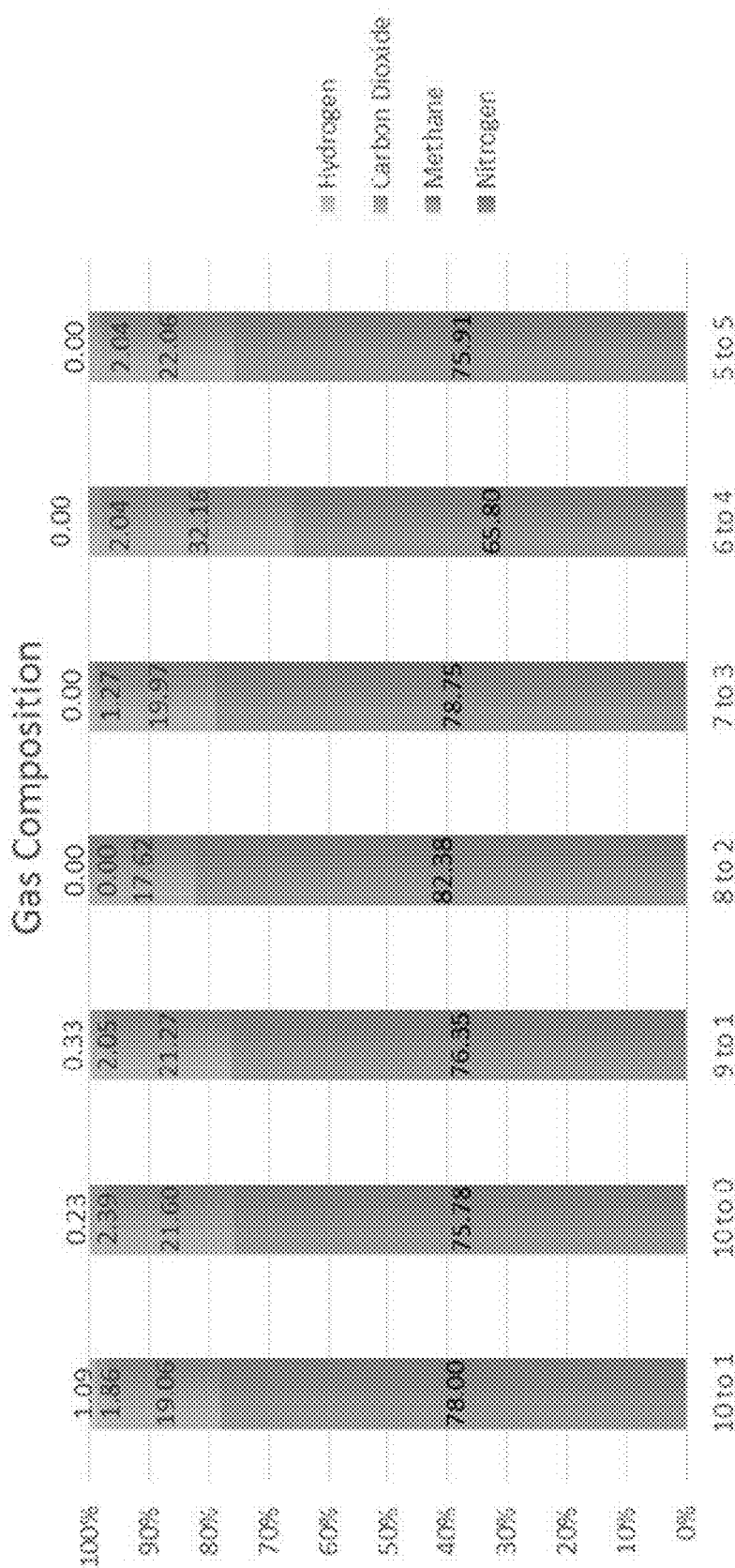

FIG. 30 shows varying gas compositions over the course of the experiment. The gas production rate was very low, the data is not included in this figure. The detection limit of the Gas GC for carbon dioxide, methane, and nitrogen was about 1%. The lower detection limit of hydrogen was about 0.2%. After the 9 to 1 ethanol to acetate ratio, hydrogen becomes undetectable. The numbers in the bars show the averages of the composition. Order of data within the bars: Top* (hydrogen), next$^+$($CO_2$), third (methane), bottom (nitrogen). * The Hydrogen 'bar' is not present in 8:2, 7:3, 6:4 and 5:5 (based on moles). $^+$ The $CO_2$ 'bar' is not present in 8:2 (based on moles).

Figure 31:
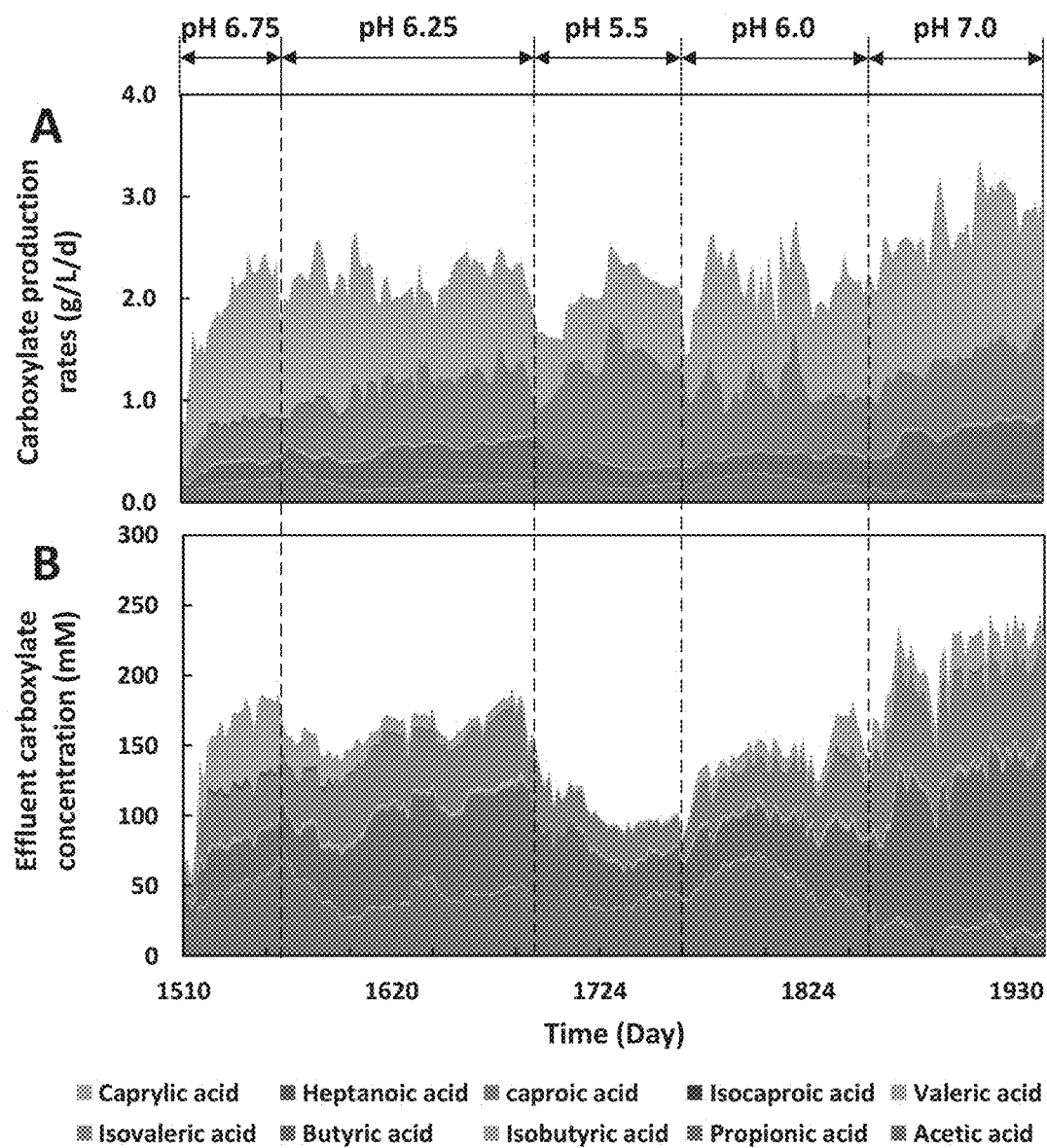

FIG. 31 shows production rate (A) and effluent concentration (B) of carboxylates in 5 phases with different bioreactor pH (6.75, 6.25, 5.5, 6.0 and 7.0).

Figure 32:
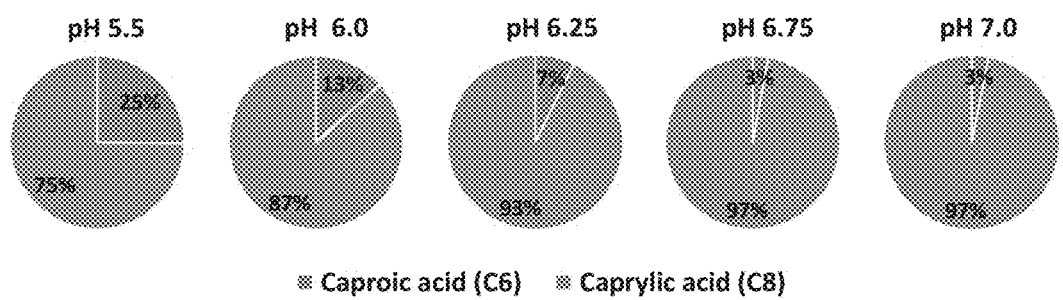

FIG. 32 shows molar percentage of caproic acid and caprylic acid in MCCAs oil.

Figure 33:
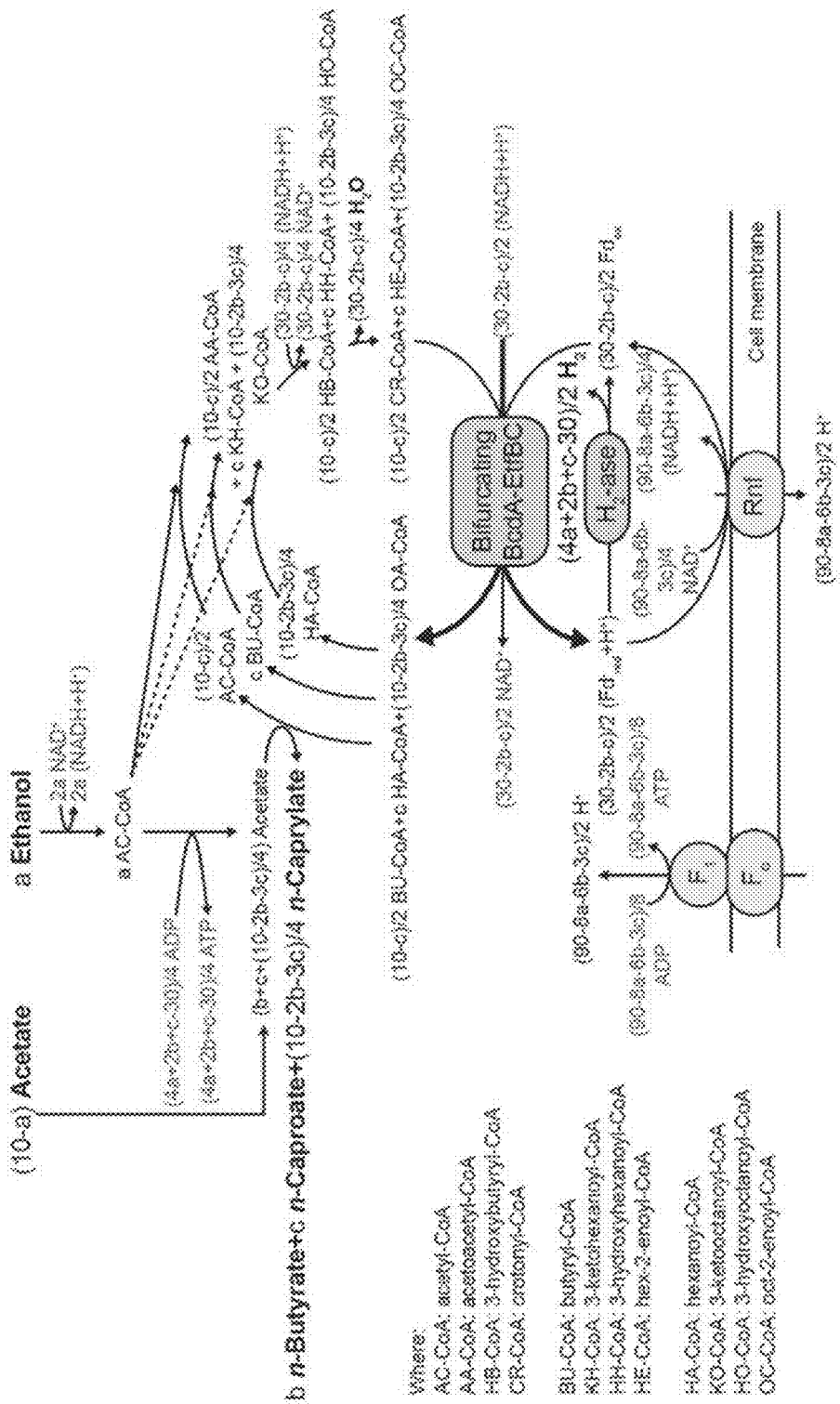

FIG. 33 shows generalized stoichiometric model for the fermentation of ethanol and acetate to n-butyrate, n-caproate, n-caprylate, and molecular hydrogen by *Clostridium kluyveri*. This model is the extended version of a previously developed model. The variable "a" represents moles of ethanol, "b" represents moles of n-butyrate, "c" represents moles of n-caproate. Redox factors are highlighted in blue; classical energy conservation in red; and more recently described mechanisms of energy conservation in yellow. $F_0/F_1$ is $H^+/Na^+$-pumping ATP synthase complex and Rnf is the ferrodoxin-NAD reductase complex.

Figure 34:
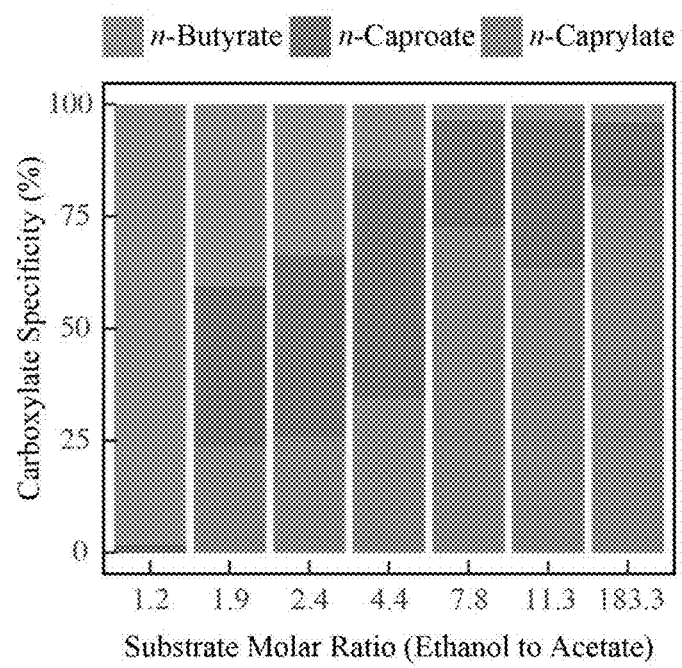

FIG. 34 shows COD specificity (gCOD carboxylate/g COD other carboxylate(s)) of carboxylate produced at each substrate molar ratio during the main periods of the Example (Periods 1 to 7) for n-butyrate, n-caproate, and n-caprylate.

Figure 35:
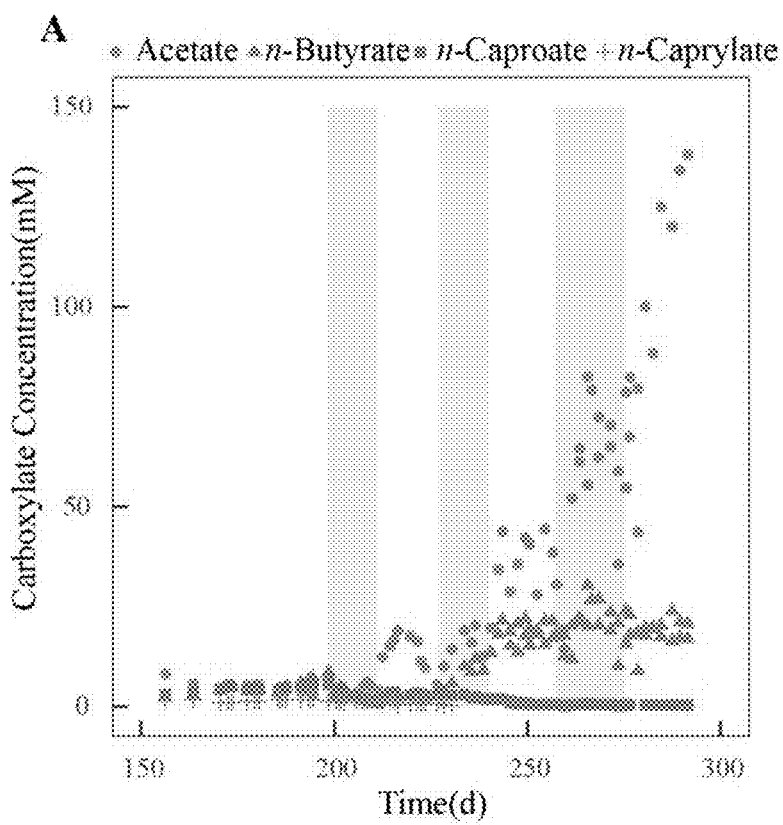
Figure 35:
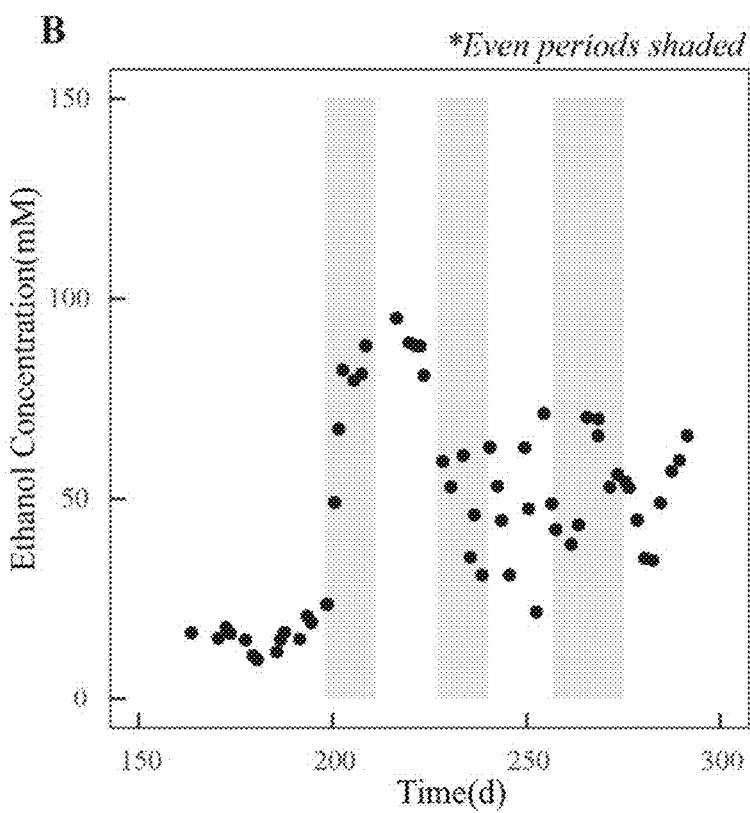

FIG. 35 shows effluent concentrations of carboxylates (A) and ethanol (B) during the operating period in the bioreactor. Shaded sections represent even periods (i.e., Period 2, Period 4, Period 6).

Figure 36:
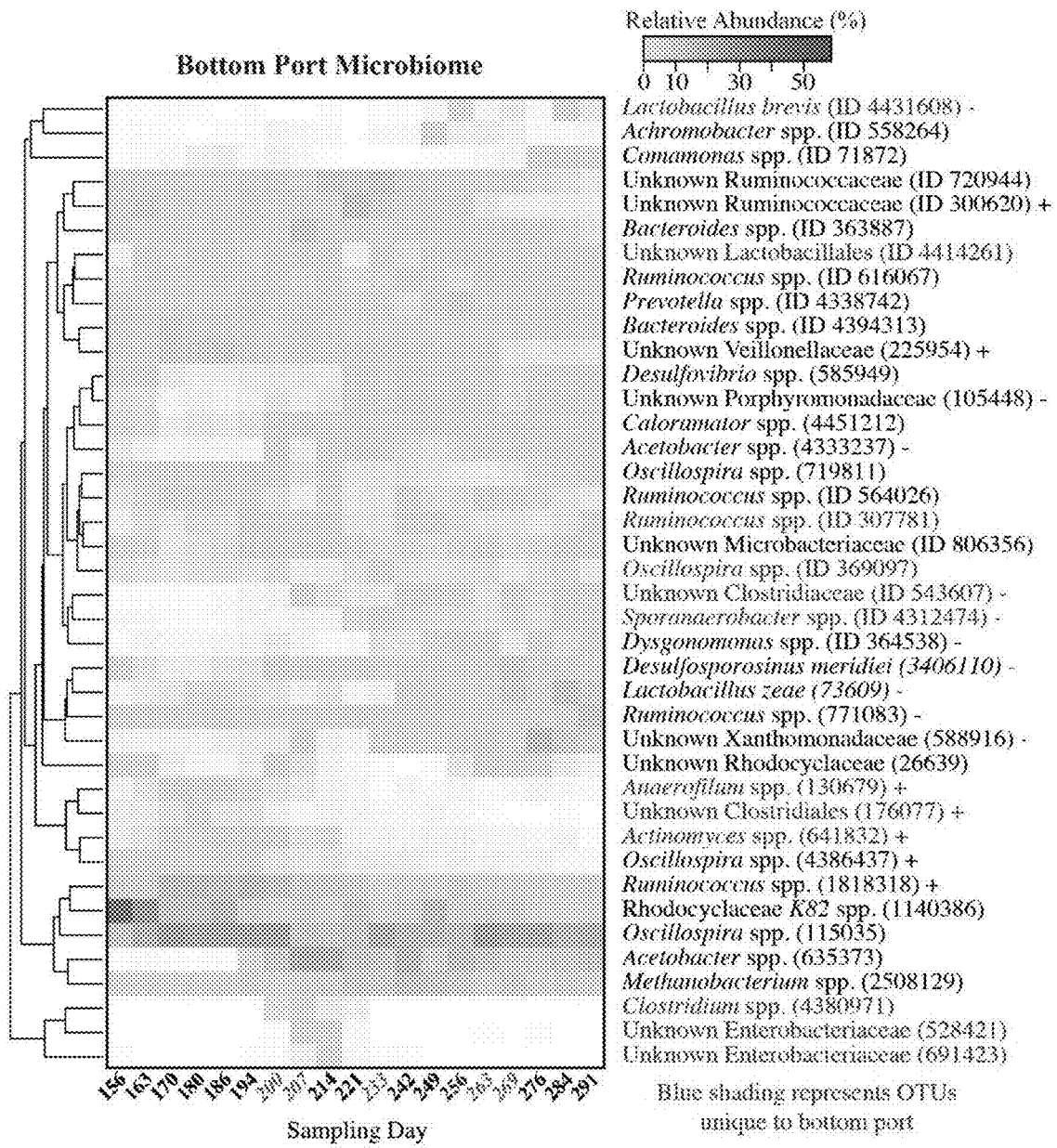

FIG. 36 shows a heat map of relative OTU abundances in biomass samples taken from the bottom port of the bioreactor during the main periods of the Example (Periods 1 to 7). Sampling day numbers are shaded grey to represent even periods (Periods 2, 4, and 6). Relative abundance fraction is represented by the color gradient shown. OTUs that reached over 1% relative abundance in any one sample are represented, resulting in 40 OTUs. OTUs are clustered hierarchically (average linkage) based on the Bray-Curtis dissimilarity index. Lowest level taxonomy names as well as OTU IDs are provided. Blue shading represents OTUs that are unique to bottom of the bioreactor (i.e., not found in the samples taken from the middle of the bioreactor). + or − symbols represents whether the relative abundance of the OTU was found to be significantly positively (+) or negatively (−) correlated with n-caprylate specificities based on Spearman's rank correlation coefficient (p<0.001).

Figure 37:
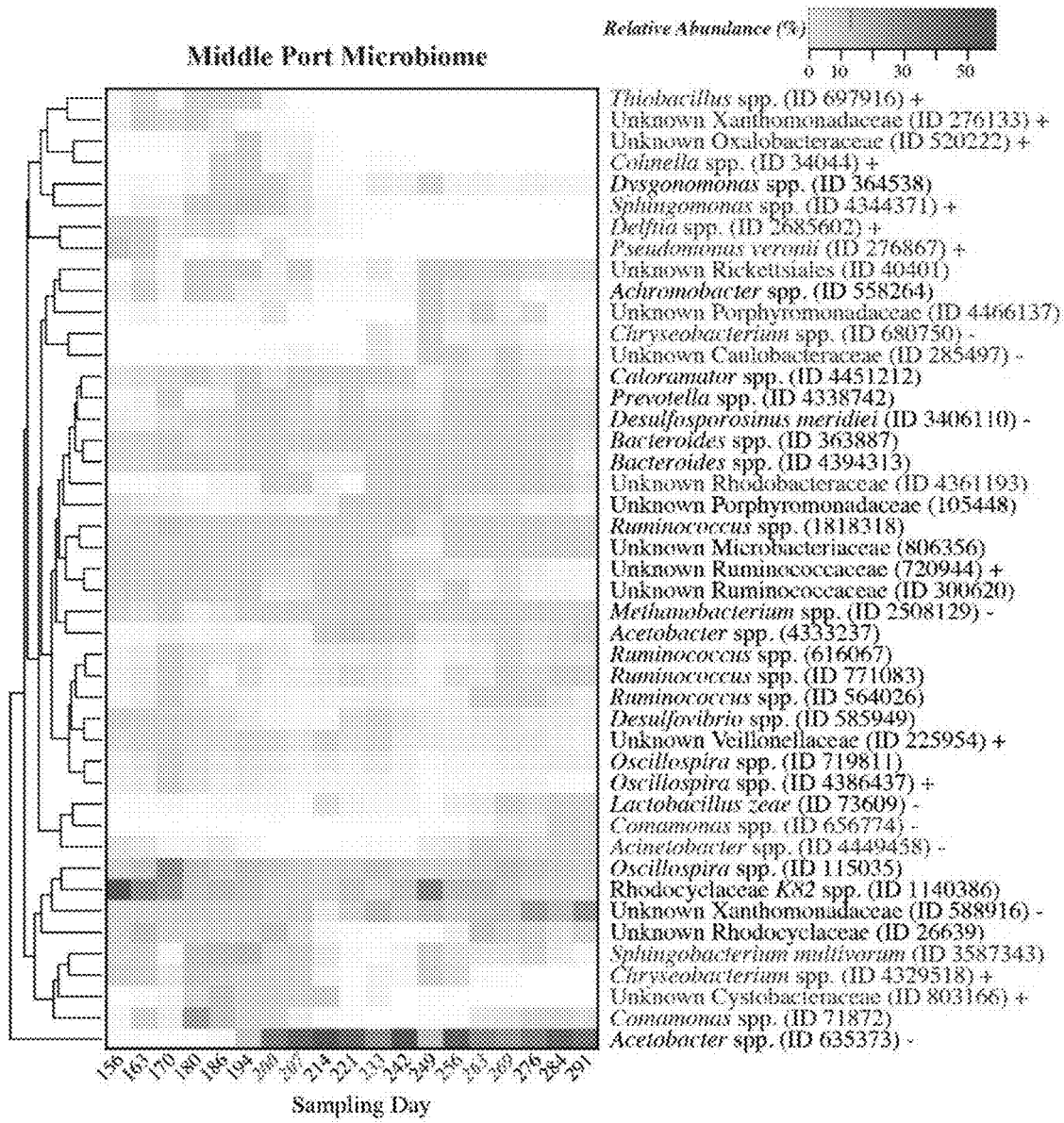

FIG. 37 shows a heat map of relative OTU abundances in biomass samples taken from the middle of the bioreactor during the main periods of the Example (Periods 1 to 7). Relative abundance fraction is represented by the color gradient shown. OTUs that reached over Sampling day numbers are shaded grey to represent even periods (Periods 2, 4, and 6). 1% relative abundance in any one sample are represented, resulting in 40 OTUs. OTUs are clustered hierarchically (average linkage) based on the Bray-Curtis dissimilarity index. Lowest level taxonomy names as well as OTU IDs are provided. Blue shading represents OTUs that are unique to middle of the bioreactor (i.e., not found in the samples taken from the bottom of the bioreactor). + or − symbols represent whether the relative abundance of the OTU was found to be significantly positively (+) or negatively (−) correlated with n-caprylate specificities based on Spearman's rank correlation coefficient (p<0.001).

Figure 38:
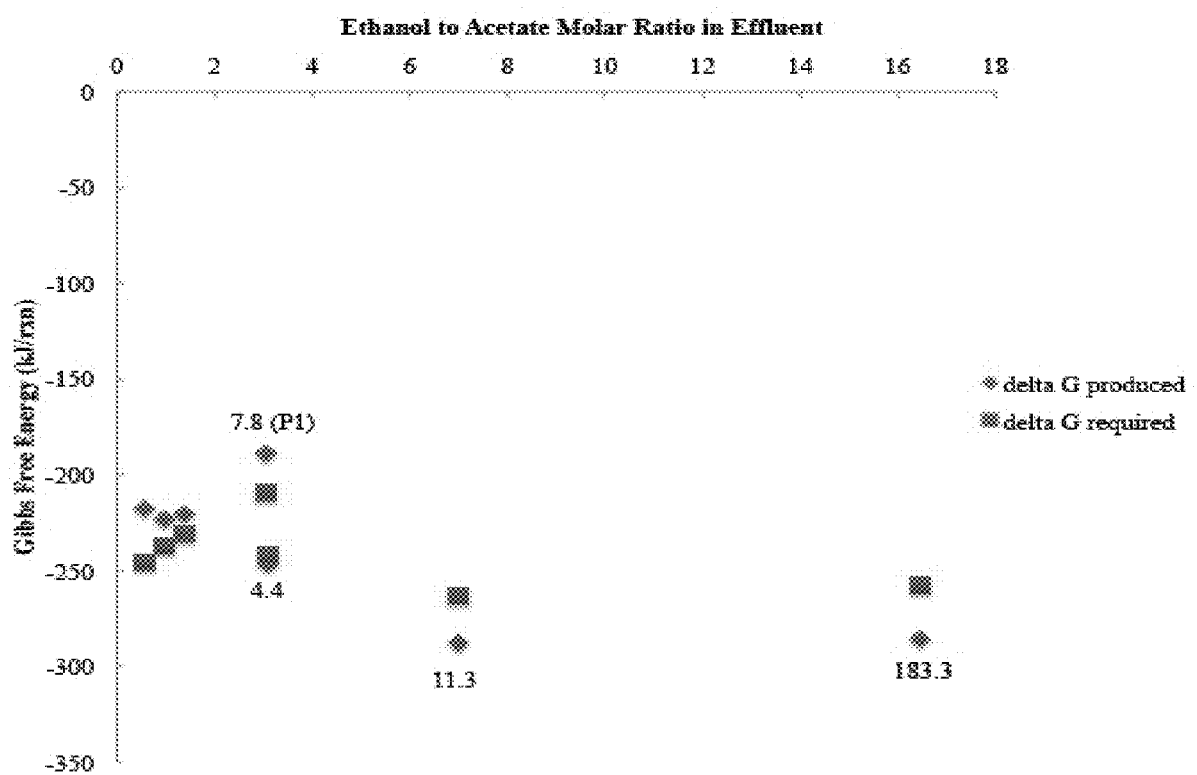

FIG. 38 shows Gibbs free energy of an example of a reaction vs. ethanol-to-acetate molar ratio measured in bioreactor. Gibbs free energy of the reaction based on the ethanol and carboxylate concentrations measured in the bioreactor is plotted as delta G produced. Delta G required is calculated based on the amount of ATP produced based on the stoichiometric model and assuming that −72 kJ is required per mole of ATP produced. Numbers on figure indicate the substrate molar ratios that were fed into the bioreactor, for the higher substrate molar ratios.

Figure 39:
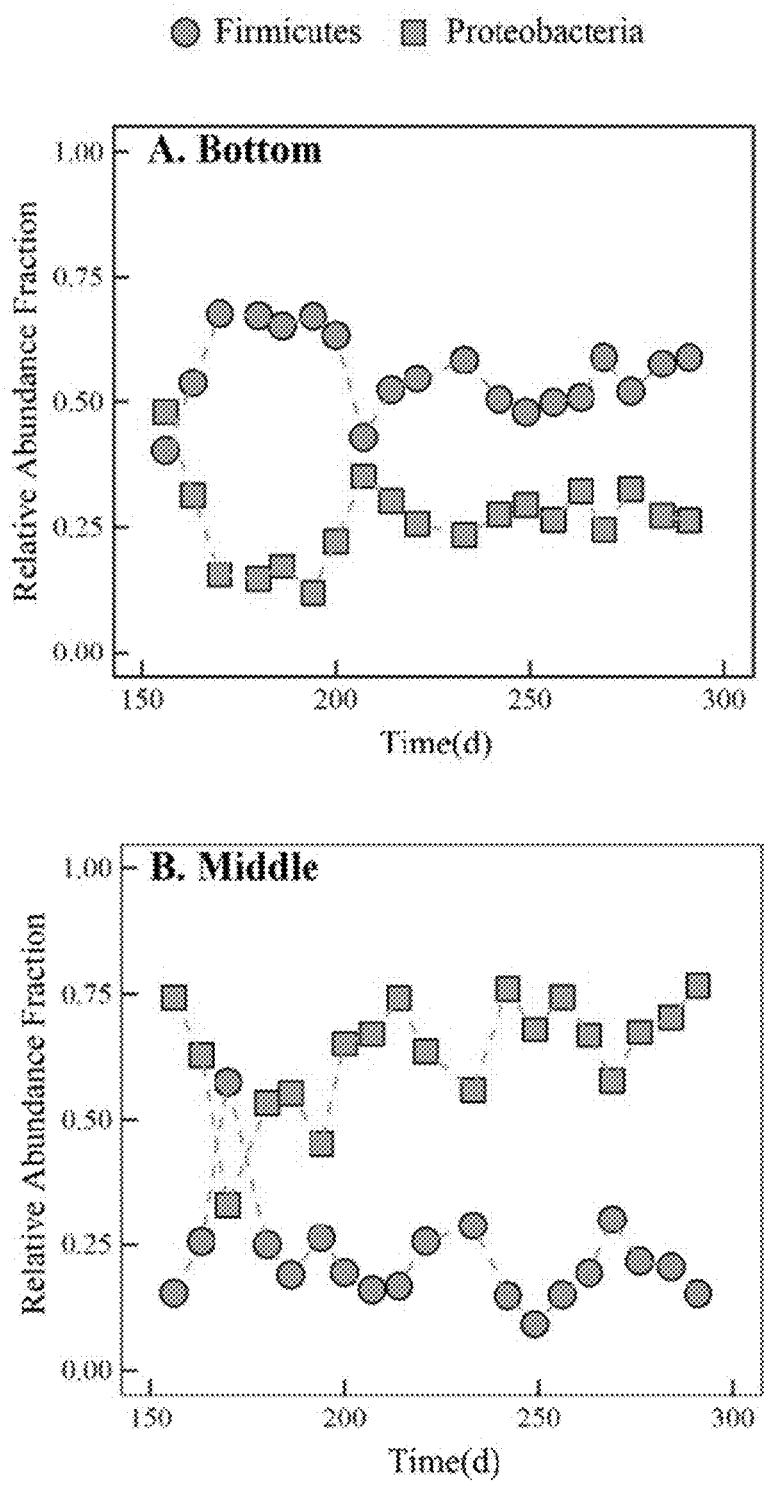

FIG. 39 shows the relative abundance of the phyla Firmicutes and Proteobacteria in the samples collected from the bottom (A) and middle (B) sampling ports of the bioreactor.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides methods for producing caprylic acid. The present disclosure also provides systems for producing caprylic acid.

Our previous work produced mainly C6, and when we considered if we could mainly produce C8 rather than C6, we did not consider it possible. The results presented herein were surprising, especially the greater amounts of C8 relative to C6 produced.

Caprylate is a carboxylate, and herein this term is used to include both the dissociated species (caprylate) and the undissociated species (caprylic acid). Caprylic acid and caprylate are also known as n-octanoic acid and n-octanoate.

Caprylate can have various counter cations. Examples of suitable cations include, but are not limited to, sodium ion, potassium ion, and the like. The present methods produce mainly caprylate, the other carboxylates are at low productivities. This technology uses microbiomes at, for example, ambient pressures, reducing capital costs by ensuring a simple bioreactor design.

An anaerobic upflow bioreactor was used to produce levels of n-caprylate at levels that have not been previously reported. For one example, this increase in the n-caprylate productivity to 19.4 g chemical oxygen demand (COD)/L-d with a product ratio of n-caprylate to n-caproate of 11 g COD/g COD. In another example, this ratio was 25 g COD/g COD at an earlier operating period though with a little lower productivity, resulting in a specificity of 96% when compared to all carboxylates. We accomplished this high n-caprylate productivity and specificity by: 1) feeding a substrate with ethanol as the sole carbon source or alternatively, a high ethanol-to-acetate ratio as the sole carbon source; 2) extracting the n-caprylate product from the bioreactor broth; and 3) acclimating an efficient chain-elongating microbiome. Because syngas fermentation effluent consists of a high ratio of ethanol to acetate, these syngas fermentation product of ethanol and alternatively high ratio of ethanol to acetate resulted in chain elongation to produce n-caprylate.

Biomass is not a component of the instant methods/systems, unlike other bioreactor and incubation systems. For example, ethanol is used as the carbon source or, alternatively, ethanol and acetate is used as the carbon substrate, where the ratio of ethanol:acetate is kept at a high level (e.g., at least at a 5:1 molar ratio).

We obtained the breakthrough of producing mainly caprylate due to a combination of operating conditions: 1) using ethanol as the sole substrate or in some instance using high substrate ratio of ethanol to acetate; 2) the presence of in-line product extraction that is selective for longer-chain carboxylates; and 3) the adaptation of an efficient microbiome. Our bioprocess is versatile and can be coupled to existing fermenters to displace ethanol distillation.

In an aspect, the present invention provides methods of producing caprylate/caprylic acid. The methods are based on reaction of a carbon substrate (e.g., ethanol or an ethanol/acetate mixture) with a microbiome that has been acclimated to produce caprylate/caprylic acid. The methods are also based on removal of a portion of or all of the caprylate/caprylic acid (referred to herein as extraction, pertraction, or stripping) during the acclimation phase and/or production phase. In an example, a method does not comprise passing an electric current through the reaction medium and/or electrical stimulation of the microbiome or one or more chain-elongation bacteria.

Figure 3:
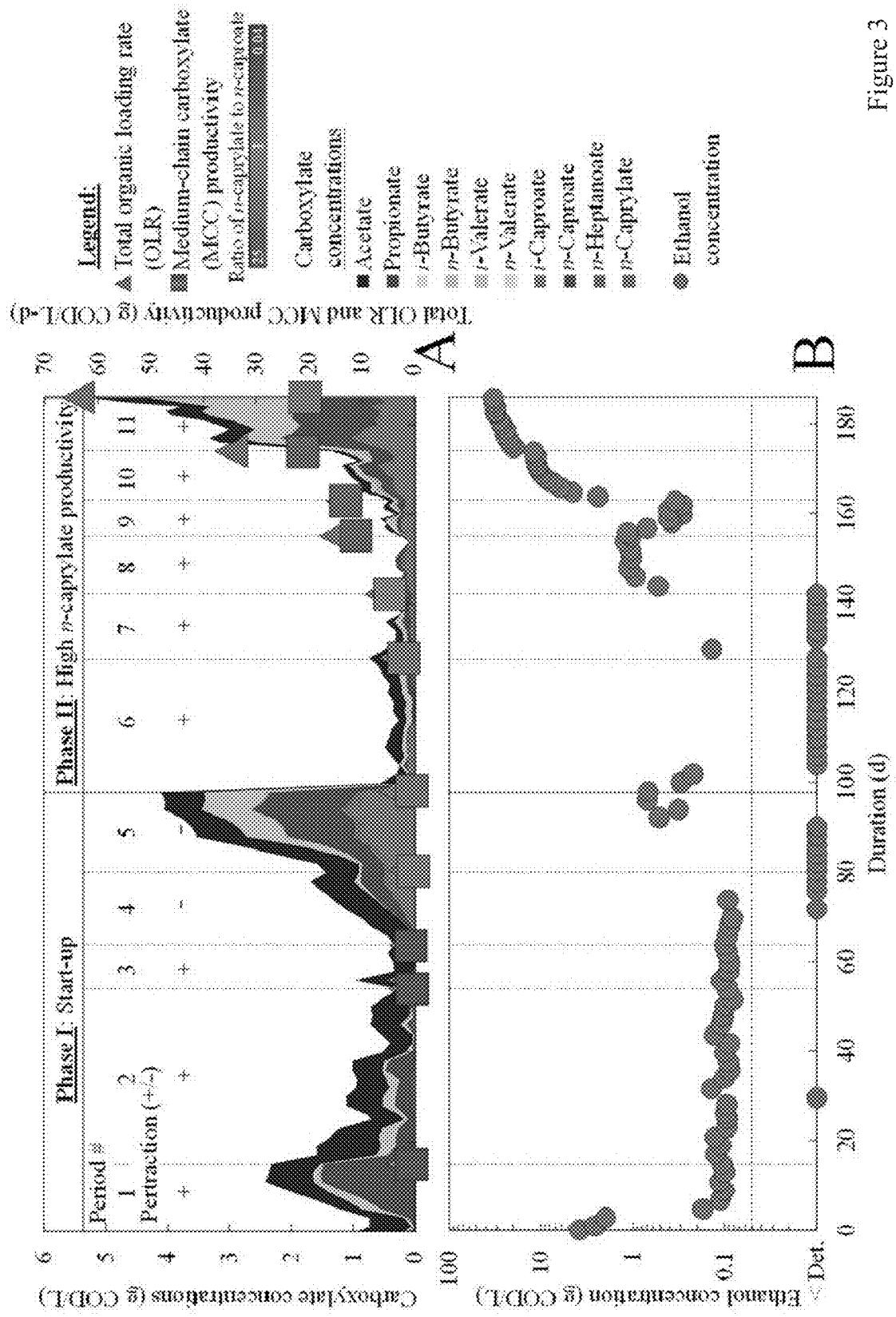
FIG. 3 shows examples of bioreactor broth concentrations, organic loading rates, and medium-chain carboxylate productivities. Concentrations carboxylates (A) and of ethanol (B) in the bioreactor broth were determined from samples collected every other day or daily. Average medium-chain carboxylate (MCC) productivities (A) and total organic loading rates (OLRs) (A) for each operating period are also shown. A color gradient was used to show the product ratio of n-caprylate (green) to n-caproate (purple) with blue representing a mixture of these two products. Operating phases, operating periods, and presence (+) or absence (−) of product recovery via in-line pertraction are indicated. Detection limits were 0.05 g COD/L (0.5 mM) for ethanol and ~0.02 g COD/L (~0.1 mM) for carboxylates.

In an example, a method for producing a product composition comprising caprylate(s) (e.g., n-caprylic acid, n-caprylate, or a combination thereof) comprises an acclimation phase (e.g., Phase I described herein), a production phase (e.g., Phase II described herein), and, optionally, one or more selection periods (e.g., period 5 in FIG. 3). For example, a method comprises: providing a reaction medium comprising one or more chain-elongating bacteria species, which may be present as all of or a portion of a microbiome, having a pH of 5-8 (e.g., 5-7.5, 5-7, 5-6, 5-5.55, 5.1-5.2, or 5.5); adding substrate comprising ethanol or a mixture of ethanol and acetate (e.g., an ethanol and acetate mixture having an ethanol:acetate molar ratio of 5:1 or greater); holding (e.g., at a temperature of 25 to 38° C.) the reaction medium during an acclimation phase (e.g., for at least 1 day) until the reaction mixture produces a desired about of n-caprylic acid or n-caprylate (an efficient chain elongation microbiome is acclimated); continuously removing at least a portion or all of the caprylic acid formed in the reaction medium during the acclimation phase, where the reaction medium is maintained at a pH of 5-8 (e.g., 5-7.5, 5-7, 5-6, 5-5.55, 5.1-5.2, or 5.5) during the holding and, optionally, continuously removing, where after the acclimation phase the reaction mixture produces a composition comprising, for example, at least 0.01% by weight, or 0.05% by weight or 0.1% by weight caprylate(s) (e.g., caprylic acid) in the reaction medium based on the total weight of the reaction medium, and continuously removing during a production phase at least a portion or all of the n-caprylic acid or n-caprylate formed in the reaction medium to form the product composition.

A method can used an acclimated microbiome or one or more chain-elongating bacteria species. For example, a method comprises: providing a reaction medium comprising an acclimated microbiome or one or more chain-elongation bacteria; holding the reaction medium at a desired temperature (e.g., at a temperature of 25 to 38° C.) and maintaining the reaction medium a pH of 5-8 (e.g., 5-7.5, 5-7, 5-6, 5-5.55, 5.1-5.2, or 5.5), and continuously removing during a production phase at least a portion or all of the n-caprylic acid or n-caprylate formed in the reaction medium to form the product composition.

Figure 5:
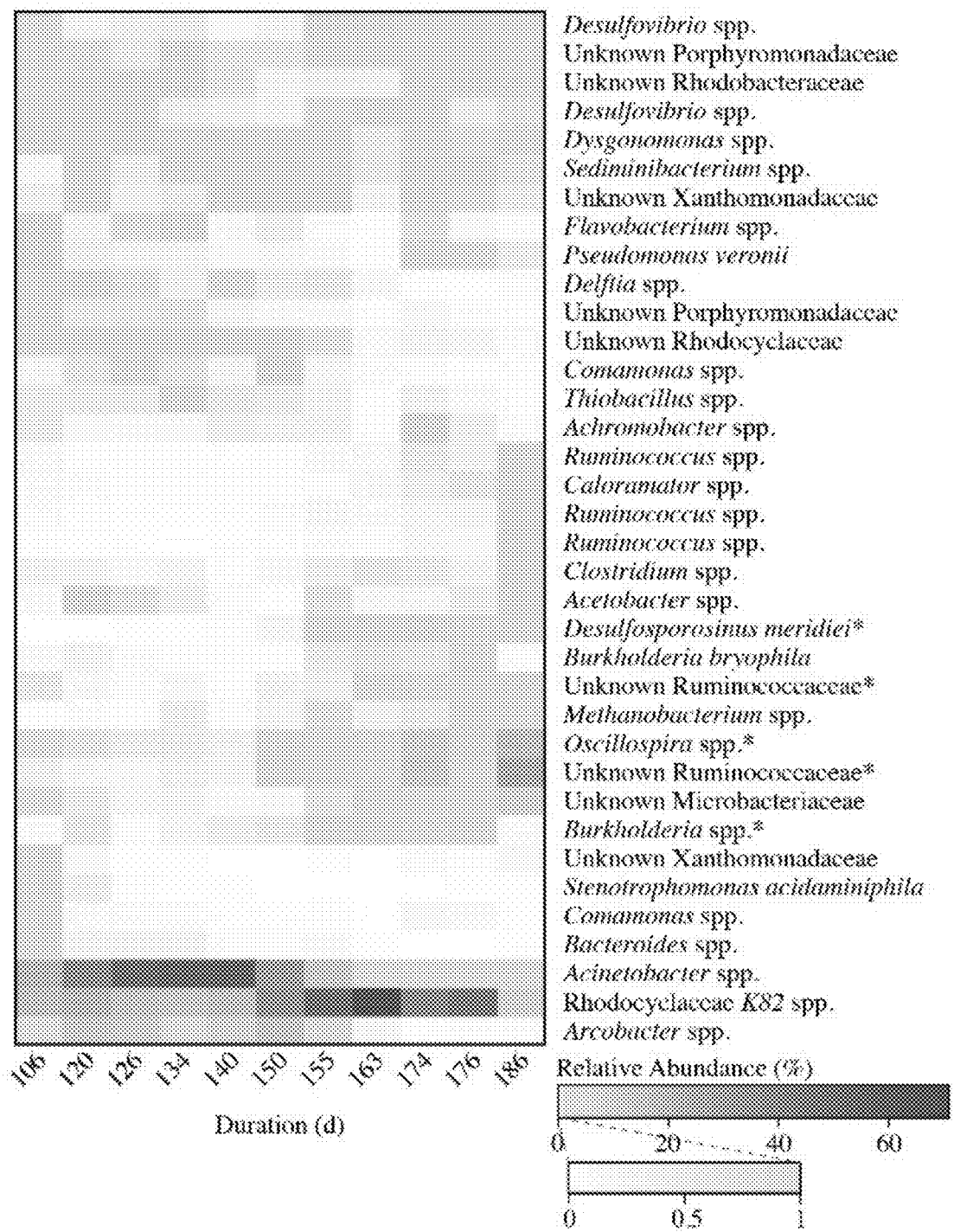
FIG. 5 shows a heat map of relative abundances for 36 OTUs in 11 reactor microbiome samples during the high n-caprylate productivity of Phase II. During Phase II, each of the 36 operational taxonomic units (OTUs) listed comprised at least one percent of the relative abundance for one or more of the microbiome samples collected. OTUs were clustered hierarchically (average linkage) based on the Bray-Curtis dissimilarity index. OTUs were grouped together based on both the average relative abundance and abundance profile. This resulted in the localization of OTUs with lower abundances in the top half, and OTUs with higher abundances in the bottom half of the heat map. An *Acinetobacter* spp. increased in dominance up to 55.5% of the relative abundance. Subsequently, a Rhodocyclaceae K82 spp. became dominant, comprising up to 70.8% of the relative abundance. Relative abundances of five OTUs (asterisks) were correlated ($p<0.05$) with n-caprylate productivities.

A reaction mixture (which is also referred to herein as a broth) comprises one or more species of chain-elongating bacteria. The chain-elongating bacteria can be present in the form of a microbiome. Various microbiomes or purified microbiomes can be used. Microbiomes can be naturally occurring or engineered. For example, suitable microbiomes are obtained from anaerobic environments such as, for example, anaerobic digester sludge, soil, aqueous sediments, the gut of animals, and the like. A microbiome can include a diverse microbial community. It can be an open culture in which bacteria can enter with the substrate and for which sterilization is not needed. A microbiome comprises one or more chain-elongating bacteria species. Without intending to be bound by any particular theory, it is considered that a chain-elongating bacterium forms a product compound (e.g., a caprylate product) by a reverse β-oxidation pathway by adding two carbons during each cycle. The microbiome can comprise an even community or an uneven community. In an example, a microbiome comprises 1-50 different chain-elongating bacteria species, including all integer numbers of chain-elongating bacteria species and ranges therebetween. Bacteria in the microbiome can be identified by gene sequencing. For example, the most abundant bacteria (48 operating taxonomic units, which is a quantifiable number to describe particular species of bacteria) in a microbiome are identified after 16S rRNA gene sequencing (FIG. 5 and FIG. 14 in the Example 1). In an example, a microbiome comprises 48 operating taxonomic units (bacteria species) described in FIG. 5 or FIG. 14 in Example 1. Microbiomes can produce various liquid and/or gaseous product compounds such as, for example, carboxylic acids, alcohols, aldehydes, hydrogen, carbon dioxide, methane, and the like. Examples of chain-elongating bacteria and microbiomes are provided herein. Examples of chain-elongating bacteria and microbiomes are known in the art. Examples of chain-elongating bacteria and microbiomes are commercially available.

A microbiome can comprise additional components. For example, a microbiome further comprises one or more components that facilitate growth and/or stability of a microbiome. Suitable components are known in the art. In an example, for growth, a microbiome comprises one or more trace elements including, for example, metals, nutrients, vitamins, or a combination thereof.

It is desirable to control the pH of the reaction mixture. In various examples, the pH of the reaction mixture is maintained (e.g., during the acclimation phase and production phase, and, if carried out, during one or all of the selection periods) at a pH of 3.0 to 8.0 (e.g., 5-7.5, 5-7, 5-6, 5-5.55, 5.1-5.2, or 5.5), including all 0.1 pH units and ranges therebetween.

It can be desirable to control the temperature of the reaction mixture. In various examples, the temperature of the reaction mixture is maintained (e.g., during the acclimation phase and production phase, and, if carried out, during one or all of the selection periods) at 15° C. to 45° C. (e.g., 25 to 38° C. or 30° C.), including all 0.1 C values and ranges therebetween.

The reaction mixture can be present in various environments. For example, the reaction mixture is present in an inert environment (e.g., under an inert gas such as, for example, nitrogen). The reaction mixture can be present in an anaerobic environment. The reaction can be run under ambient pressure (no pressurization is required) or under a pressurized environment. In an example, the reaction mixture is under a pressure of 0.7-1.3 atmospheres.

A reaction mixture comprises substrate. The substrate serves as a carbon source. Examples of substrate include ethanol and ethanol/acetate mixtures. Various amounts of substrates can be used. In the case where the substrate is an ethanol/acetate mixture, it may be desirable that the mixture has an ethanol to acetate molar ratio of greater than 1 to 1 or greater, 2 to 1 or greater, 4.5 to 1 or greater, 5 to 1 or greater, 5.5 to 1 or greater, 6 to 1 or greater, 10 to 1 or greater, 25 to 1 or greater, 50 to 1 or greater, or 100 to 1 or greater. In the case where the substrate is an ethanol/acetate mixture, the mixture has an ethanol to acetate molar ratio of 1:1 to 100:1, 4.5:1 to 25:1, 4.5:1 to 50:1, or 4.5 to 100:1.

Additional substrate can be added to the reaction mixture (e.g., during the acclimation phase and production phase, and, if carried out, during one or all of the selection periods). In various examples, additional substrate is added periodically added, continuously added, or a combination thereof during one of more of the phases and/or periods. It is desirable not to overfeed (feed more than the rate of chain elongation, which is equal to the extraction rate) the microbiome during one or more or all of the phases and/or periods.

A method comprises an acclimation phase (also referred to herein as a period) during which certain bacteria outgrow others to achieve an acclimated microbiome. During the acclimation phase an efficient chain elongation microbiome is produced. By "efficient chain elongation microbiome" it is meant that a microbiome produces the longest possible medium-chain carboxylate that is possible under the environmental conditions at desirable production rates. During the acclimation phase, the amount of one or more chain-elongating bacteria species are increased relative to one or more other bacteria in the reaction mixture. During the acclimation phase, a portion of or all of the caprylate product is removed (e.g., by in-line, continuous extraction as described herein) from the reaction mixture. It is desirable to maintain the caprylate product concentration at a level that is not toxic to one or more constituents of the microbiome. Too high concentrations of undissociated carboxylic acids (caprylate product(s)) can inhibit production of caprylate product(s). Accordingly, it is desirable to maintain the amount of undissociated caprylate(s) in the reaction mixture at a level that does not inhibit production of caprylate product(s).

In an example, after an acclimation phase a reaction mixture (e.g., microbiome) comprises one or more species of bacteria selected from *Ruminococcus* spp. (1818318)+, Rhodocyclaceae K82 spp. (1140386), *Oscillospira* spp. (115035), *Acetobacter* spp. (635373), and unknown Bacteroidaes, and combinations thereof. In an example, after an acclimation phase a reaction mixture (e.g., microbiome) comprises (e.g., predominantly comprises) one or more species of bacteria from the Firmicutes and/or Proteobacteria phyla. The one or more species of bacteria may present at the same or different amounts in the reaction mixture.

During the acclimation phase, the reaction mixture is held at a desired temperature (e.g., 15° C. to 45° C., 25 to 38° C., or 30° C.) until the reaction mixture provides a desired level of caprylate product. In various examples, the reaction mixture is held at a desired temperature (e.g., 15° C. to 45° C., 25 to 38° C., or 30° C.) (e.g., at a temperature of 25 to 38 (30° C.)) for at least 1 day, at least 10 days, at least 25 days, at least 50 days, at least 100 days, at least 200 days, or at least 400 days.

After an acclimation phase, the reaction mixture produces a desirable amount of (e.g., predominantly) caprylate product(s). In an example, after the acclimation phase, the reaction mixture produces caprylate product(s) so that the concentration of at least 0.01% by weight, at least 0.05% by weight, or 0.1% by weight, or 0.5% by weight caprylate product(s) in the reaction medium based on the total weight of the reaction medium. In another example, after the acclimation phase, the reaction mixture produces caprylate product(s) so that the concentration of at least 0.1 g/L or g COD/L, at least 0.5 g/L or g COD/L, or 1 g/L or g COD/L caprylate product(s) in the reaction medium based on the total weight of the reaction medium.

A method can comprise one or more selection periods. During a selection period the amount of caprylate in the reaction mixture is allowed to increase (e.g., built up) such that microbiome constituents that cannot tolerate the increased amount of caprylate do not survive and microbiome constituents that tolerate the increased amount of caprylate (do not die) are increased in the microbiome. The resulting microbiome exhibits desirable production of caprylate. Typically, the microbiome after a selection period exhibits increased production of caprylate(s) relative to that exhibited by the microbiome prior to the selection period. For example, a selection period comprises decreasing or stopping removal of caprylate from the reaction mixture (e.g., by decreasing or stopping extraction of caprylate from the reaction mixture). In an example, a selection period comprises decreasing or stopping removal of caprylate from the reaction mixture (e.g., by decreasing or stopping extraction of caprylate from the reaction mixture) for, for example, 0.5 hours to 720 days, including all 0.1 hour values and ranges therebetween. In various examples, a selection period comprises decreasing or stopping removal of caprylate from the reaction mixture (e.g., by decreasing or stopping extraction of caprylate from the reaction mixture) for 0.5 hours to 24 hours, 0.5 hours to 120 hours, or 0.5 hours to 240 hours. In other examples, the selection period can be longer than 30 days. In various examples, a selection period is carried out until the concentration of caprylate(s) (e.g., undissociated caprylate (caprylic acid)) is 0.01% or greater, 0.005% or greater, or 0.01% or greater by weight based on based on the total weight of the reaction medium. In various examples, a selection period is carried out until the concentration of caprylate(s) (e.g., undissociated caprylate (caprylic acid)) is 0.1 g COD/L or greater, 0.05 g COD/L or greater, or 0.1 gCOD/L or greater. Selection period(s) can be carried out as part of an acclimation phase and/or subsequent to an acclimation phase and/or as part of a production phase and/or subsequent to a production phase.

A method can comprise a production phase (also referred to herein as a period). During a production phase caprylate products are formed in the reaction medium. In various examples, during a production phase the n-caprylate productivity is at least 15 or at least 20 g chemical oxygen demand (COD)/L-d and/or the product ratio of n-caprylate to n-caproate of at least 10, at least 15, at least 20, or at least 25 g COD/g COD.

A product composition is formed by removal (e.g., by liquid extraction) of product compounds from the reaction mixture. Examples of liquid extraction are provided herein. A product composition comprises one or more caprylate. In an example, a product composition comprises greater than 50% by weight caprylate(s) e.g., n-caprylic acid, n-caprylate or a combination thereof) based on the total weight of all the product compounds (e.g., caprylate(s) and caproate(s)) in the product composition. In various other examples, a product composition comprises greater than 55% by weight, greater than 60% by weight, greater than 65%, greater than 70%, greater than 80% by weight, greater than 90% by weight, greater than 95% by weight, or greater than 99% by weight caprylate(s) (e.g., n-caprylic acid, n-caprylate or a combination thereof) based on the weight of all of the product compounds (e.g., caprylate(s) and caproate(s)) in the product composition. In an example, a product composition comprises 50-100% by weight caprylate(s) (e.g., n-caprylic acid, n-caprylate or a combination thereof) based on the weight of all of the product compounds in the product composition. The product composition can further comprise a solvent or mixture of solvents. For example, the solvent(s) are those used to extract the product compounds from the reaction mixture.

In various examples, a product composition comprises less than 20%, less than 10%, less than 5%, or less than 1% by weight caproate products (e.g., caproic acid, caproate, or combinations thereof) based on the weight of all of the product compounds in the product composition. In various examples, a product composition has a caprylate(s): caproate(s) weight ratio of 3:1 or greater, 4:1 or greater, 5:1 or greater, 10:1 or greater, or 20:1 or greater. In an example, a product composition comprises no detectable caproate products. Caproate products can be detected by methods known in the art. For example, caproate products are detected by gravimetric methods, spectroscopic methods (e.g., nuclear magnetic resonance (NMR) spectroscopic methods), or mass spectrometry methods (e.g., gas or liquid chromatography/mass spectrometry methods).

The steps of the methods described in the various embodiments and examples disclosed herein are sufficient to carry out the methods of the present disclosure. Thus, in an example, a method consists essentially of a combination of steps of one or more of the methods disclosed herein. In another example, a method consists of such steps.

In an aspect, the present invention provides systems for producing caprylic acid. The systems comprise a continuous extraction system (e.g., an in-line continuous extraction system). Examples of systems include, but are not limited to, anaerobic upflow bioreactors comprising a continuous extraction system (e.g., an in-line continuous extraction system). The systems can carry out a method of the present disclosure. Examples of systems are provided herein.

A system for forming a product composition comprising caprylate products comprises: a substrate (feed) source; a bioreactor in fluid communication with the substrate source, where the bioreactor includes an upflow anaerobic filter; and an in-line extraction system (also referred to herein as a pertraction system) in fluid communication with the bioreactor, where the in-line pertraction system includes: a forward membrane contactor, a backward membrane contactor; and an alkaline extraction solution source, where the in-line extraction (pertraction) system is configured to continuously recover hydrophobic, undissociated medium chain carboxylic acids from a bioreactor reaction medium from the bioreactor through the forward membrane contactor, and wherein the medium chain carboxylic acids are configured to be transferred across the backward membrane contactor to an alkaline extractor solution from the alkaline extraction solution source. For example, the in-line extraction (pertraction) system is configured for liquid-liquid extraction.

In an example, a system further comprises: a pH sensor connected to the bioreactor; and a controller in electronic communication with the pH sensor, where the controller is configured to maintain the bioreactor reaction medium at a particular pH. In an example, a system further comprising an acid addition pump in fluid communication with the bioreactor and in electronic communication with the controller. In an example, the bioreactor includes an inverted funnel configured to collect biogas. In an example, the in-line pertraction system includes a peristaltic pump.

The following examples are presented to illustrate the present disclosure. They are not intended to limiting in any matter.

Example 1

This example provides a description of methods and systems of the present disclosure.

The operating conditions of an anaerobic upflow bioreactor was optimized during a period of 185 days to accomplish the goal of producing desirable amounts of n-caprylate. We considerably increased the n-caprylate productivity to 19.4 g chemical oxygen demand (COD)/L-d with a product ratio of n-caprylate to n-caproate of 11 g COD/g COD. This ratio was even 25 g COD/g COD at an earlier operating period with a lower productivity, resulting in a specificity of 96% when compared to all carboxylates. We accomplished this high n-caprylate productivity and specificity by: 1) feeding a substrate with ethanol as the sole carbon source or alternatively, a high ethanol-to-acetate ratio as the sole carbon source; 2) extracting the n-caprylate product from the bioreactor broth; and 3) acclimating an efficient chain-elongating microbiome. Because syngas fermentation effluent consists of a high ratio of ethanol to acetate, these syngas fermentation products were coupled with chain elongation to increase n-caprylate product value.

Until now, mainly n-caproate has been produced with chain elongation. We show here, for the first time, that n-caprylate at high specificities can be produced as well. One of the requirements is a high substrate ratio of ethanol to acetate, which is a characteristic of syngas fermentation effluent, opening up a new resource-recovery path toward the production of sustainable and extractable fuels and chemicals. For this Example, ethanol as the electron donor was likely first produced from these gases by the microbiome.

Since the highest n-caprylate productivity was achieved with a synthetic, dilute ethanol and acetate substrate solution, the question is where this particular substrate would come from in a sustainable society. Fortunately, waste-derived syngas-fermentation effluent provides an emerging source of dilute ethanol and acetate for the sustainable production of MCCs. The syngas platform converts diverse feedstocks, including forestry residues and other relatively dry biomass wastes, into carbon monoxide- and hydrogen-rich producer gas, which we refer to here as syngas, via thermochemical processes. In addition, certain industrial off-gasses, such as those from steel mills, serve as vast sources of carbon monoxide and hydrogen gases as well. The emerging field of syngas fermentation with anaerobic carboxytrophic clostridia has been successful in converting these carbon monoxide-rich gases into dilute streams of ethanol and acetate. Others had already reported high ethanol productivities of up to 10 g/L-h (500 g COD/L-d) and ethanol-to-acetate ratios of up to 30 (based on COD). As a result, industrial-scale fermenters at steel plants are being designed and built to convert syngas into ethanol via microbial fermentation.

Subsequent conversion of the dilute ethanol and acetate from syngas fermentation with chain elongation would be advantageous for several reasons: 1) the value for C8 molecules is considerably higher than for C2 molecules on a weight basis; 2) conventional product recovery using energy-intensive distillation can be cost-prohibitive for recovery of dilute ethanol, while hydrophobic MCC products can be extracted at a lower expenditure of energy; and 3) without chain elongation, acetate reject from distillation would need to be treated in a wastewater treatment plant. Since both syngas fermentation and chain elongation are anaerobic bioprocesses, they are complementary with similar temperature and pH optimums and with growth nutrients that can be shared.

Here, we provided synthetic syngas-fermentation effluent with dilute ethanol and acetate at a high substrate ratio of 15 (based on COD) to a continuously fed bioreactor with a microbiome at a pH value of 5.5 and with in-line product extraction. In addition, we performed batch experiments to understand the effect of varying substrate concentrations and ratios on microbiome performance. We achieved a high product ratio of n-caprylate to n-caproate by optimizing the operating conditions of a bioreactor with in-line product recovery. Our results show that we can mainly produce n-caprylate from syngas-fermentation effluent with very little n-caproate as a co-product.

Experimental. Continuously fed bioreactor system. An upflow anaerobic filter was used with constant bioreactor broth recycling through an in-line membrane liquid-liquid extraction (i.e. pertraction) system (FIG. 8). The bioreactor was a vertically oriented cylinder, which was made of Plexiglas®, with an inner diameter of 6 cm. The total volume was 0.90 L, but Kaldnes K1 packing material (Evolution Aqua, Wigan, United Kingdom) was added, resulting in a working volume of 0.70 L. The bioreactor was wrapped with tubing in which hot water from a heating bath (VWR Scientific Model 1104, Radnor, Pa., USA) was recirculated for temperature control, resulting in a constant temperature of 30±1° C. inside the bioreactor. A pH probe (Mettler 405-DPAS SC K85, Columbus, Ohio, USA) was mounted at the top of the bioreactor. Automated pH control of the bioreactor broth was maintained with a controller (Eutech Instruments alpha-pH800, Vernon Hills, Ill., USA) and a corresponding acid addition pump (Mityflex 913, Bradenton, Fla., USA). Hydrochloric acid (0.5 M) was added to the well-mixed feed and recycle inlet at the base of the bioreactor. Fresh media containing ethanol and acetate was continuously fed from a refrigerated vessel (4° C.) into the base of the bioreactor using a peristaltic feed pump (Cole Parmer L/S Digital Economy Drive, Vernon Hills, Ill., USA) at average rates of ~0.18 or 0.44 L/d (hydraulic retention time [HRT]=3.9 or 1.6 d, respectively). The effluent continuously exited the bioreactor via an overflow line connected to the top of the bioreactor. The exit of the overflow line was submerged within a secondary effluent reservoir. An inverted funnel was used to collect the biogas within the bioreactor and was connected to a flow meter (Ritter MGC-1, Bochum, Germany). In addition, a gas-sample septum and a bubbler were placed in the gas collection system. A sampling port for biomass samples was placed halfway up the vertically oriented bioreactor.

Pertraction system. Product extraction was accomplished with a pertraction system similar to those used in previous reports. A forward and a backward membrane contactor (1.4 $m^2$ each, Membrana Liqui-Cel 2.5×8, X50 membrane, Charlotte, N.C., USA) were used for the bioreactor setup (FIG. 8). A hydrophobic solvent was circulated continuously in the lumen of the hydrophobic hollow-fiber membrane modules as a selective barrier to extract primarily MCCs instead of SCC; the solvent consisted of mineral oil with 30 g/L tri-n-octylphosphine oxide (TOPO) (Sigma Aldrich, St. Louis, Mo., USA). The stirred alkaline extraction solution was initially buffered with 0.3 M sodium borate and was maintained at pH 9 with automated addition of 5 M sodium hydroxide using a controller (Eutech Instruments alpha-pH800, Vernon Hills, Ill., USA) and a corresponding base pump (Mityflex 913, Bradenton, Fla., USA). A constant bioreactor broth recycle flow of 130 L/d was maintained using a peristaltic pump (ColeParmer 7553-30, Vernon Hills, Ill., USA). To prevent fouling or solids accumulation in the forward membrane contactor, bioreactor broth was drawn from the top of the anaerobic filter and was then pumped through a custom-built, 1.6-mm stainless-steel strainer (Danco 88886, Shorewood, Ill., USA), a 65-µm filter (McMaster-Carr 44205K21, Elmhurst, Ill., USA), and a subsequent 5-µm filter (Pentek GS-6 SED/5, Upper Saddle River, N.J., USA). Peristaltic pumps (ColeParmer 7553-30, Vernon Hills, Ill., USA) provided continuous recycle flows of 7 and 43 L/d for the mineral oil solvent and alkaline extraction solution, respectively.

For abiotic pertraction experiments an aqueous solution of procured synthetic n-caproate was continuously fed to the abiotic upflow anaerobic filter after adjusting the pH to 5.5. The flow rate of the bioreactor broth recycle was varied to determine the effects of flow rate on mass transfer (but all other flow rates were held constant, including the mineral oil solvent, the alkaline extraction solution, and the aqueous n-caproate feed solution). For the abiotic experiment we used a larger forward and backward membrane contactors than for the bioreactor experiment, but with identical hydrophobic hollow-fiber membranes (8.1 $m^2$ each, Membrana Liqui-Cel 4×13, X50 membrane, Charlotte, N.C., USA). We corrected for the difference in superficial velocity.

Periods for the bioreactor study. This bioreactor was divided into two phases: I) a start-up phase with continuous feeding (with the product extraction system on or off); and II) a high n-caprylate productivity phase (with continuous feeding and the product extraction system on). Each phase was then divided into several distinct operating periods. From period to period, several operating parameters were varied, including the: organic loading rate (OLR); HRT; bioreactor pH; and operation with or without product extraction (Table 1). Each operating period was operated for at least five HRT periods, and average bioreactor loading rates and concentrations were reported.

Table 1. Operating conditions and average bioreactor broth concentrations. Average substrate and product concentrations in the bioreactor broth are reported for each operating period with their corresponding operating conditions. Detection limits were approximately 0.05 g COD/L (0.5 mM) for ethanol and approximately 0.02 g COD/L (~0.1 mM) for other carboxylates. B.D.: below detection. Uncertainty is represented by 95% confidence intervals.

periods at an average HRT of 1.5±0.1 d). Further increases in the OLR were made on Day 163 (Period 10; Phase II; Days 163-174) to 34.7 g COD/L-d and on Day 174 (Period 11; Phase II; Days 174-186) to 63.8 g COD/L-d (Table 2).

Table 2. Operating conditions and average loading rates and carboxylate productivities. Average productivities of medium-chain carboxylates (MCCs) (e.g. n-caprylate, n-caproate) and short-chain carboxylates (SCCs) are

TABLE 1

| | | Operating conditions | | | Average bioreactor broth concentrations | | | | | |
|---|---|---|---|---|---|---|---|---|---|---|
| Phase # | Period # | Pertraction +/- | Start-End d | Bioreactor pH | [Ethanol] | [n-Caprylate] | [n-Caproate] | [n-Butyrate] | [Acetate] | [Other SCC] |
| | | | | | | | g COD/L | | | |
| I | 1 | + | 0-15 | 5.8 ± 0.6 | 1.01 ± 1.11 | B.D. | 0.80 ± 0.50 | 0.13 ± 0.08 | 0.64 ± 0.12 | 0.03 ± 0.03 |
| | 2 | + | 15-54 | 5.6 ± 0.2 | 0.10 ± 0.01 | B.D. | 0.19 ± 0.07 | 0.11 ± 0.05 | 0.57 ± 0.09 | 0.02 ± 0.01 |
| | 3 | + | 54-64 | 5.4 ± 0.1 | 0.10 ± 0.01 | 0.05 ± 0.12 | 0.03 ± 0.09 | 0.01 ± 0.01 | 0.39 ± 0.10 | 0.01 ± 0.03 |
| | 4 | − | 64-80 | 5.5 ± 0.1 | 0.04 ± 0.04 | 0.21 ± 0.14 | 0.23 ± 0.12 | 0.03 ± 0.03 | 0.61 ± 0.08 | 0.05 ± 0.03 |
| | 5 | − | 80-98 | 5.3 ± 0.1 | 0.25 ± 0.24 | 0.76 ± 0.16 | 1.03 ± 0.33 | 0.60 ± 0.24 | 0.75 ± 0.10 | 0.15 ± 0.03 |
| II | 6 | + | 98-128 | 5.2 ± 0.1 | 0.03 ± 0.05 | 0.03 ± 0.02 | 0.07 ± 0.02 | 0.08 ± 0.02 | 0.22 ± 0.05 | 0.01 ± 0.01 |
| | 7 | + | 128-142 | 5.1 ± 0.1 | 0.02 ± 0.05 | 0.04 ± 0.02 | 0.09 ± 0.02 | 0.07 ± 0.02 | 0.13 ± 0.06 | 0.03 ± 0.02 |
| | 8 | + | 142-155 | 5.0 ± 0.1 | 0.99 ± 0.20 | 0.09 ± 0.02 | 0.06 ± 0.04 | 0.00 ± 0.00 | 0.01 ± 0.02 | 0.06 ± 0.03 |
| | 9 | + | 155-163 | 5.1 ± 0.1 | 0.49 ± 0.24 | 0.18 ± 0.03 | 0.08 ± 0.03 | 0.05 ± 0.05 | 0.09 ± 0.04 | 0.05 ± 0.03 |
| | 10 | + | 163-174 | 5.1 ± 0.1 | 8.67 ± 2.12 | 0.34 ± 0.08 | 0.28 ± 0.06 | 0.11 ± 0.03 | 0.13 ± 0.02 | 0.09 ± 0.06 |
| | 11 | + | 174-186 | 5.2 ± 0.1 | 27.33 ± 3.01 | 0.69 ± 0.10 | 1.12 ± 0.11 | 1.09 ± 0.38 | 0.57 ± 0.12 | 0.04 ± 0.02 |

During Period 1 in Phase I (Days 0-15), pre-washed inoculum was added to the upflow anaerobic filter after which a continuous feeding strategy was initiated. The substrate ratio of ethanol to acetate was 6 (g COD/g COD), the HRT was 4.2 days, and the total OLR was 2.1 g COD/L-d (Table 2). The bioreactor was re-inoculated on Day 15 of Period 2 in Phase I (Days 15-54) with pre-washed inoculum, and then again on Day 54 of Period 3 of Phase I (Days 54-64) with non-washed inoculum. This last inoculation carried some carboxylates from the inoculation bioreactor. During Period 4 of Phase I (Days 64-80), the product extraction was turned off. This action was taken to encourage an increase in concentrations of undissociated medium-chain carboxylic acids (MCCAs), such as undissociated n-caproic acid and n-caprylic acid, in the bioreactor broth. On Day 80 of Period 5 in Phase I (Days 80-98), we increased the substrate ratio of ethanol to acetate from 6 to 15 g COD/g COD. In addition, we increased the OLR from 1.8 to 3.8 g COD/L-d (Table 2). Day 98 represented the start of Phase II (Period 6; Days 98-128), by switching on the product extraction system. Next, we increased the OLRs in a stepwise fashion during 4 out of the next 5 periods in Phase II. In Period 7 (Days 128-142) and 8 (Days 142-155), the OLR was increased from 3.7 to 6.3 and to 15.0 COD/L-d without changing the HRT. On day 155 of Period 9 in Phase II (Days 155-163), we shortened the HRT from 3.3 to 1.6 days by increasing the flow rate of the growth medium. However, we maintained a similar OLR by reducing the ethanol and acetate concentrations. By increasing the flow rate on Day 155, the average yeast-extract loading rate increased from 0.4±0.1 g COD/L-d (for the first eight periods at an average HRT of 3.9±0.1 d) to 1.1±0.1 g COD/L-d (for the last three reported for each operating period with their corresponding operating conditions. These total productivities were calculated as the sum of average bioreactor effluent production rates plus average transfer rates via pertraction for each operating period, normalized to the bioreactor working volume. Acetate was continuously fed to the bioreactor, so negative production rates indicate net consumption of acetate. Uncertainty is represented by 95% confidence intervals. Total organic loading rates (OLRs) include loading from ethanol, acetate, and yeast extract. For most of the experiment, to vary the ethanol and total organic loading rates, the concentrations of ethanol and acetate in the basal medium were changed (instead of the HRT). The substrate ratio of ethanol to acetate was approximately 6 g COD/g COD until it was increased to 15 g COD/g COD on Day 80 of Phase I, Period 5. For each operating period, the concentrations of ethanol and total organics (g COD/L) in the continuously fed basal medium can be calculated by multiplying the reported average ethanol and total organic loading rates (g COD/L-d) by the corresponding average HRT (d). The yeast extract concentration in the media was consistently 1.6 g COD/L (1.25 g/L), and the corresponding yeast extract loading rate was approximately 0.4±0.1 g COD/L-d throughout the first 8 operating periods (HRT=3.9±0.1 d). In Period 9, the feed flow rate was increased, which decreased the HRT, and the yeast extract loading rate was consequently increased to 1.1±0.1 g COD/L-d (HRT=1.5±0.1 d). No considerable changes were observed in the n-caprylate or the total MCC productivities between Period 8 and Period 9. Uncertainty is represented by 95% confidence intervals.

TABLE 2

| | Operating conditions | | | Loading rates | | Average carboxylate productvities | | | | |
|---|---|---|---|---|---|---|---|---|---|---|
| Phase # | Period # | Pertraction +/- | HRT d | Total OLR | Ethanol | n-Caprylate | n-Caproate | n-Butyrate | Net Acetate | Other SCC |
| | | | | g COD/L-d | | | | g COD/L-d | | |
| I | 1 | + | 4.2 ± 0.6 | 2.1 ± 0.6 | 1.4 ± 0.4 | 0.0 ± 0.0 | 0.5 ± 0.3 | 0.0 ± 0.0 | −0.1 ± 0.0 | 0.0 ± 0.0 |
| | 2 | + | 4.8 ± 0.6 | 1.8 ± 0.1 | 1.2 ± 0.1 | 0.0 ± 0.0 | 0.3 ± 0.1 | 0.3 ± 0.2 | −0.1 ± 0.0 | 0.3 ± 0.1 |

TABLE 2-continued

| Phase # | Period # | Operating conditions Pertraction +/− | HRT d | Loading rates Total OLR g COD/L-d | Ethanol | Average carboxylate productvities n-Caprylate | n-Caproate | n-Butyrate g COD/L-d | Net Acetate | Other SCC |
|---|---|---|---|---|---|---|---|---|---|---|
|  | 3 | + | 3.8 ± 0.3 | 1.7 ± 0.4 | 1.2 ± 0.2 | 0.0 ± 0.0 | 0.6 ± 0.3 | 0.0 ± 0.0 | −0.1 ± 0.0 | 0.0 ± 0.0 |
|  | 4 | − | 4.5 ± 0.9 | 1.8 ± 0.3 | 1.2 ± 0.2 | 0.0 ± 0.0 | 0.1 ± 0.0 | 0.0 ± 0.0 | −0.1 ± 0.0 | 0.0 ± 0.0 |
|  | 5 | − | 4.4 ± 0.2 | 3.8 ± 0.4 | 3.2 ± 0.3 | 0.2 ± 0.0 | 0.2 ± 0.1 | 0.1 ± 0.1 | 0.0 ± 0.0 | 0.0 ± 0.0 |
| II | 6 | + | 3.7 ± 0.2 | 3.7 ± 0.4 | 3.1 ± 0.3 | 0.8 ± 0.1 | 1.2 ± 0.2 | 0.3 ± 0.1 | −0.2 ± 0.0 | 0.0 ± 0.0 |
|  | 7 | + | 3.8 ± 0.4 | 6.3 ± 0.4 | 5.6 ± 0.4 | 2.3 ± 0.4 | 2.2 ± 0.2 | 0.0 ± 0.0 | −0.3 ± 0.0 | 0.1 ± 0.1 |
|  | 8 | + | 3.3 ± 0.3 | 15.0 ± 2.9 | 13.7 ± 2.6 | 10.6 ± 0.3 | 0.4 ± 0.1 | 0.0 ± 0.0 | −0.9 ± 0.2 | 0.0 ± 0.0 |
|  | 9 | + | 1.6 ± 0.1 | 13.7 ± 1.8 | 12.2 ± 1.6 | 11.2 ± 1.5 | 1.7 ± 0.3 | 0.0 ± 0.0 | −0.8 ± 0.1 | 0.3 ± 0.2 |
|  | 10 | + | 1.5 ± 0.1 | 34.7 ± 2.7 | 31.8 ± 2.5 | 19.4 ± 1.1 | 1.7 ± 0.3 | 0.1 ± 0.0 | −2.0 ± 0.2 | 0.1 ± 0.0 |
|  | 11 | + | 1.5 ± 0.0 | 63.8 ± 6.7 | 59.1 ± 6.2 | 13.2 ± 0.8 | 7.5 ± 0.3 | 0.7 ± 0.2 | −3.6 ± 0.4 | 0.0 ± 0.0 |

Growth medium and inoculum. The modified basal medium was described previously, and it contained nutrients, yeast extract (1.25 g/L, 1.6 g COD/L), and sodium carbonate (0.032 g/L), but no gaseous carbon dioxide. Ethanol and acetate were added to the basal medium at a fixed substrate ratio of 6 g COD/g COD (4 mol/mol) until Day 79, and was then increased to 15 g COD/g COD (10 mol/mol) on Day 80 (Period 5). For each operating period, the substrate concentrations of ethanol and acetate were varied to achieve desired loading rates (Table 2). The medium pH was adjusted with 5 M sodium hydroxide to achieve an appropriate pH in the bioreactor (Table 1). The inoculum was derived from a well-characterized reactor microbiome that was fed ethanol-rich yeast fermentation beer. This reactor microbiome had been fed semi-continuously (once every two days) throughout an operating period of more than three years at the time of inoculation. For pre-washed inoculation, the inoculum was triple-washed in basal media, and ~100 mL of this inoculum was added to the continuously fed bioreactor. For the non-washed inoculation, 100 mL of inoculum was added.

Batch reactor microbiome experiments. Batch reactor microbiome experiments were conducted in 160-mL glass serum bottles to which 80 mL of basal medium was added. The initial concentrations and substrate ratios of ethanol and acetate in the basal medium were varied. MES buffer was also added to this media at concentrations that were equimolar to the initial ethanol concentrations, and the initial pH was adjusted to 5.4 with 5 M sodium hydroxide. Inoculum was prepared as described previously, and ~4 mL of pre-washed inoculum was added to 80 mL volume (5% inoculum, v/v). The batch reactor microbiomes were then: sparged with nitrogen gas; capped with butyl rubber stoppers; sealed and crimped with aluminum caps; inverted; and incubated without shaking at 30° C. These serum bottles were then mixed well and sampled after 12 days, and liquid samples (pH 5.4±0.1) were collected in 2-mL Eppendorf tubes for determination of the concentrations of ethanol and carboxylates. Each treatment was conducted in triplicate batch bottles, and all data reported reflect the average values from these triplicates.

Calculations. We use g COD for our results instead of g product to compare results and to ascertain the balance between substrate and product. The conversion factors for 1 g COD to g product are: 0.48 (ethanol); 0.92 (acetate); 0.65 (propionate); 0.54 (n-butyrate); 0.49 (n-valerate); 0.45 (n-caproate); 0.42 (n-heptanoate); and 0.41 (n-caprylate). Carboxylate productivities were calculated as average values for each operating period. Herein, the average bioreactor effluent production rate (g COD/d) plus the average transfer rate via product extraction (g COD/d) were summed to yield the total production rate (g COD/d). Effluent production rates were calculated as the average bioreactor broth concentration divided by the average HRT for each period. Average transfer rates were calculated by first plotting the increasing amounts of individual carboxylates in the alkaline extraction solution against time. Least squares methods were then used to determine the slope and the sample standard deviation (LINEST function, Microsoft Excel). We divided the production rates by the working bioreactor volume to determine the total productivities (g COD/L-d). All concentrations, rates, and yields were converted to a g COD basis. Feed flow rates were determined volumetrically; effluent rates were determined gravimetrically. Uncertainty was represented by 95% confidence intervals: the standard error was first calculated as the quotient of the sample standard deviation divided by the square root of the number of samples; then, the standard error was multiplied by a t-value corresponding to the degrees of freedom (based on the number of samples). Uncertainty was propagated through calculations, and 95% confidence intervals were included with reported data (e.g. productivities).

Liquid and gas analysis. Liquid samples (1.5 mL) were collected from the continuously fed bioreactor and the alkaline extraction solution every other day or daily. Bioreactor broth samples were collected from the broth recycle line between the 5-μm filter and the forward membrane contactor. Alkaline extraction solution samples were collected from the well-mixed reservoir (~3 L). Concentrations of carboxylates and ethanol were determined with separate gas chromatography (GC) systems. The concentrations of methane, carbon dioxide, and hydrogen gases (>2000 ppm) were measured using a GC system. Furthermore, the concentration of hydrogen gas (<2000 ppm) was determined using a reduction gas detector (RGD) (Trace Analytical RGD, Menlo Park, Calif., USA). The RGD inlet was connected to a packed column (Restek, ShinCarbon ST 80/100, Bellefonte, Pa., USA) for peak separation, which was installed in a GC system (Gow Mac 580, Bethlehem, Pa., USA).

Biomass samples, DNA extraction, PCR, sequencing, and microbial community analysis. Biomass samples were taken from the bioreactor broth at 16 time points throughout the experimental period, as well as one sample from the inoculum. The bioreactor broth was thoroughly mixed by quickly withdrawing and refilling a 60 mL syringe ten times. During this sampling, settled flocculent biomass was resuspended. The sample was collected in 2-mL Eppendorf tubes. These 2-mL samples were then centrifuged at 16,873×g for 4 min and the supernatants were discarded. Concentrations of wet solids in these pelleted biomass samples ranged from 23 to 76 mg/L. These pelleted biomass samples were stored at −80° C. until further processing.

Genomic DNA was extracted using the PowerSoil DNA isolation kit (MO BIO Laboratories Inc., Carlsbad, Calif.). Modifications to the protocol include utilization of custom bead tubes containing a mixture of 300 mg of 0.1-mm diameter and 100 mg of 0.5-mm diameter silica/zirconia beads, and physical cell lysis with bead-beating at 3450 oscillations/min for 45 s. The DNA amplification protocol was described previously with the following exceptions: 1) Mag-Bind RxnPure Plus magnetic beads solution (Omega Biotek, Norcross, Ga., USA) were used instead of Mag-Bind E-Z Pure; 2) only 20 ng DNA per sample were pooled instead of 100 ng. QIITA (qiita.microbio.me) was used for initial processing of the sequencing data. The sortmerna method was used to bin sequences into operational taxonomic units (OTUs) at 97% identity. Taxonomy was assigned for representative sequences selected for each OTU using the Greengenes v13.8 database from August 2013. The remaining analyses were performed in QIIME v1.9. Singleton OTUs were removed from the dataset.

Community analysis, including beta diversity and unconstrained ordination, was performed as described previously with the following exceptions: 1) the alpha diversity was calculated using the Shannon diversity index rather than Chao1; 2) the Pearson correlation coefficient was calculated for samples from Phase III with the functions cor and cor.test in the R stats package. At a significance level of $p<0.05$ and $n=11$, the relative abundance of an OTU would be positively correlated with n-caproate productivity if the Pearson r was greater than 0.602. Heat maps were created to represent OTU relative abundances via the gplots package in R.

Figure 1:
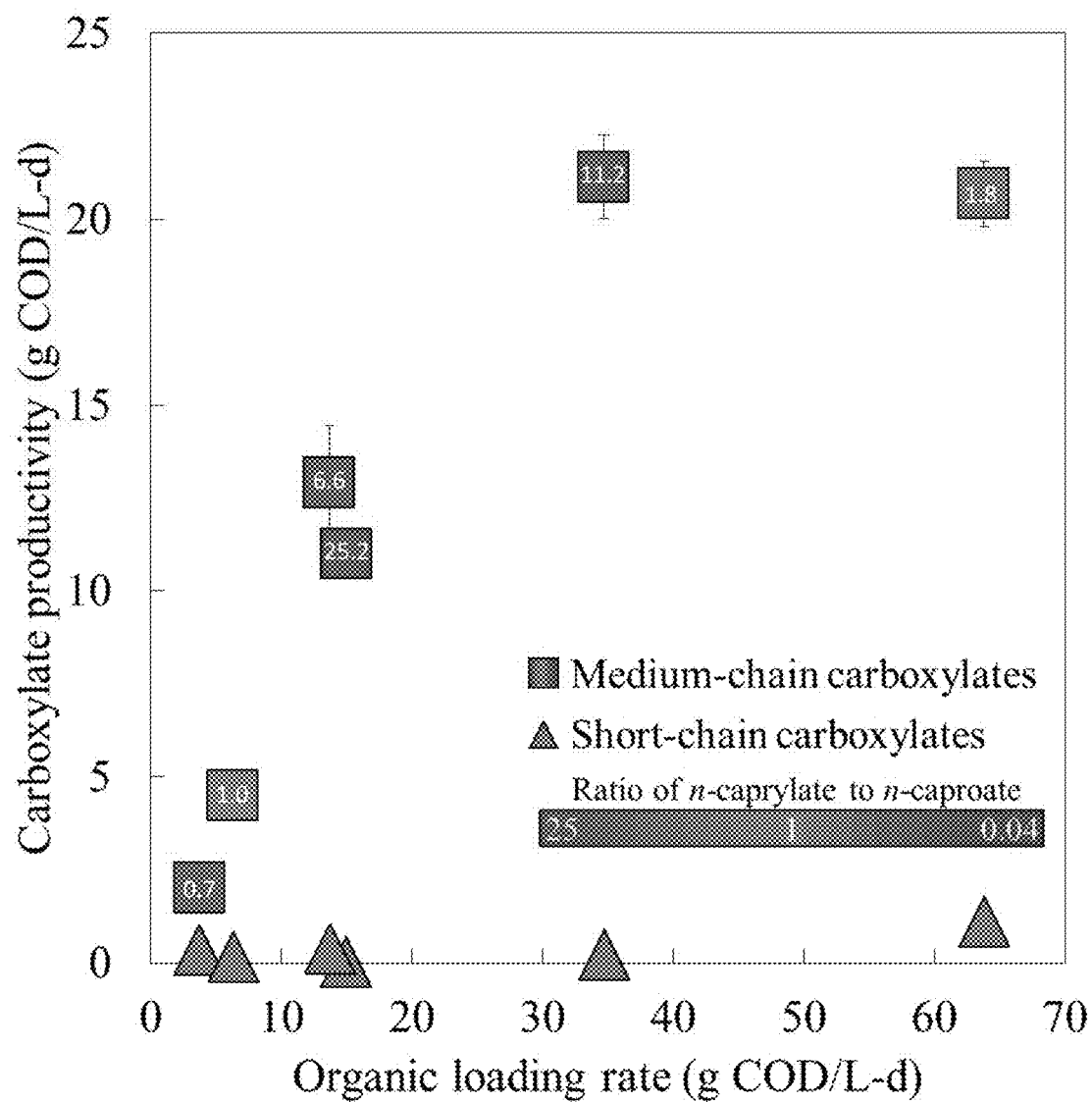
FIG. 1 shows examples of carboxylate productivities and product ratios of n-caprylate to n-caproate. Medium-chain carboxylate (MCC) productivities increased to 21.1 g COD/L-d by increasing organic loading rates (OLRs) up to 34.7 g COD/L-d. A higher OLR resulted in a stagnated MCC productivity. n-Caprylate (green) was the predominant product, with a product ratio of n-caprylate to n-caproate of 25 g COD/g COD (22.7 by weight) at an OLR of 15.0 g COD/L-d, and a product ratio of 11 g COD/g COD (10 by weight) at an OLR of 34.7 g COD/L-d. Error bars represent 95% confidence intervals. Data shown are from Phase II.
Figure 2:
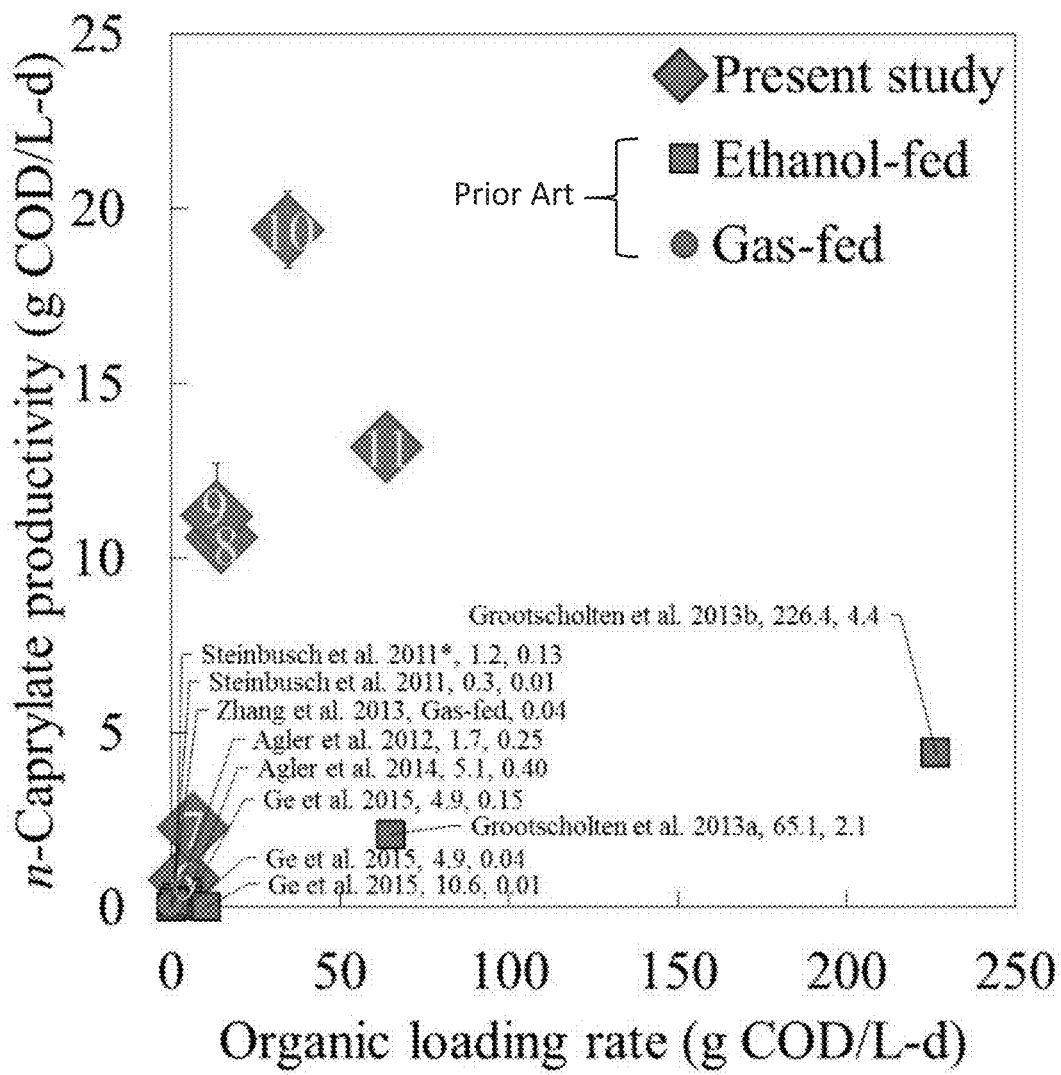
FIG. 2 shows n-caprylate productivities from bioreactors with ethanol as an electron donor, including Phase II. Results from previously published studies for which n-caprylate production was reported (small squares and X). Also shown are results from this Example (large squares). Operating periods from Phase II of the present Example are labeled with white font. Maximum instantaneous values reported are indicated (*). The referenced study (see main text), the organic loading rate (OLR), and the n-caprylate productivity are listed. Both n-caprylate productivities and OLRs are presented on logarithmic scales. One study produced n-caprylate in a bioreactor in which gas composed of carbon dioxide and hydrogen was fed; they did not report OLRs, so this marker was placed at an OLR near the sum of the total carboxylate volumetric production rates. Our study achieved maximum n-caprylate productivities up to 19.4 g COD/L-d (Period 10).

Results and Discussion. We achieved the highest n-caprylate productivity and specificity ever reported. During a period of more than 180 days we operated an upflow anaerobic filter with and without product extraction and with a continuous feed of synthetic ethanol and acetate. We achieved a maximum average MCC productivity of 21.1 g COD/L-d in this Example during Period 10 (FIG. 1). The corresponding n-caprylate productivity was 19.4 g COD/L-d (Table 2), which is more than four times the highest n-caprylate productivity (4.4 g COD/L-d) reported previously, which was achieved without product extraction and at a much higher OLR (FIG. 2). Importantly, the product ratio of n-caprylate to n-caproate was 11 (based on COD) during this operating period of 11 days in Period 10 (Table 1) at an HRT of 1.5 d (Table 2). During an earlier period at a lower MCC productivity (Period 8), we achieved a product ratio of n-caprylate to n-caproate of 25 (FIGS. 1-2). Both these product ratios are considerably higher than what had been observed. Previously, the maximum reported value was 1.47, but at very low productivities. Thus, this is the first Example that has reported mainly n-caprylate at a very high product specificity (product vs. other carboxylate products) of 96% (Period 8) and 91% (Period 10), which included all SCC and MCC products from this operating period (on a COD basis).

Even though the MCC productivity was high during the period with a maximum n-caprylate productivity (Period 10), we were over feeding the bioreactor slightly with a total OLR of 34.7 g COD/L-d (FIG. 1). This resulted not only in the observed decrease in the product ratio of n-caprylate to n-caproate from 25 to 11 (Period 8 to 10), but also resulted in a decrease in the COD conversion efficiencies to MCCs from 73% to 61% (n-caprylate plus n-caproate in COD/total OLR in COD; Table 3), respectively. The COD conversion efficiencies to MCCs based on ethanol COD decreased from 80% to 67% during this operating period (Table 3). A further increase in the OLR to 63.8 g COD/L-d during Period 11 resulted in decreases in the n-caprylate productivity, the n-caprylate-to-n-caproate ratio (1.7), and the COD conversion efficiency, while the total MCC productivity stagnated (FIG. 1). The over-feeding conditions during Period 10-11 led to increases in the concentrations of: 1) carboxylates (FIG. 3A) ethanol (FIG. 3B) in the broth of the bioreactor; and 2) hydrogen and methane in the biogas of the bioreactor (FIG. 9). The concentrations of hydrogen and methane only increased considerably during Period 11 to reach concentrations above 3,000 and 30,000 ppm, respectively (FIG. 9). This occurred when a large excess of reducing equivalents became available. A considerable fraction of the produced hydrogen was converted to methane via hydrogenotrophic methanogens at a pH of 5.2 with carbon dioxide being the limiting substrate for these methanogens. Clearly, it is important to not over feed the bioreactor when the objective is to achieve a high product ratio of n-caprylate to n-caproate.

A high substrate ratio of ethanol to acetate is needed to obtain a high product ratio of n-caprylate to n-caproate. During Phase II when high n-caprylate productivities were achieved, the substrate ratio of ethanol to acetate was 15. We had increased this ratio from 6 to 15 in Period 5 when product extraction was off. This change was made in tandem with an increase in the OLR from 1.8 to 3.8 g COD/L-d. These changes led to an increase in the n-caprylate-to-n-caproate ratio to 0.5 (FIG. 1). An ethanol-to-acetate ratio of 4.4 g COD/g COD without product extraction was previously used and achieved the highest n-caprylate productivity before this work, but with a relatively low n-caprylate-to-n-caproate ratio. The lower ethanol-to-acetate ratio may explain the considerably lower product ratio of 0.04 compared to 0.5 g COD/g COD, which we achieved without product extraction.

It was previously known with pure cultures of *C. kluyveri* in batch experiments that increasing the substrate ratios of ethanol to acetate led to increased product ratios of n-caproate (C6) to n-butyrate (C4) (FIG. 10). Production of n-caprylate was not seen. For example, when the concentration of ethanol was increased with a fixed acetate concentration, the product ratio of n-caproate to n-butyrate and the n-caproate productivity increased until the ethanol-to-acetate ratio was 6 (based on COD) and the ethanol concentration of 44 g COD/L (460 mM) became inhibiting (FIG. 10C). In a recent review, a thermodynamic model showed that both a higher substrate ratio of ethanol to acetate and a higher product ratio of n-caproate to n-butyrate ratio would be energetically advantageous for *C. kluyveri*. In relation to syngas fermentation, the relatively high ethanol-to-acetate ratios up to 30 (g COD/g COD) in syngas-fermentation effluent are an important advantage for chain elongation to a longer product. Use of this syngas fermentation product in reactor systems produced n-butyrate and n-caproate but n-caprylate production was not seen [28].

Figure 4:
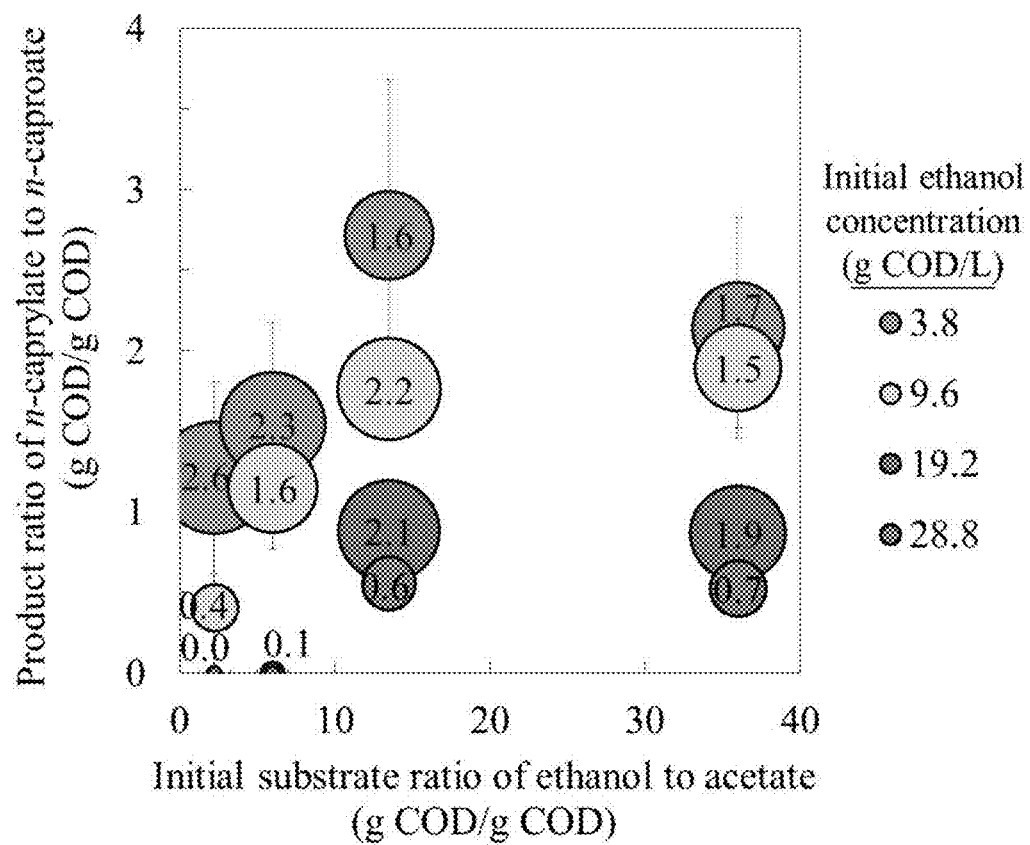
FIG. 4 shows product ratios and substrate ratios for a batch experiment with microbiomes. Increased substrate ratios of ethanol to acetate led to increased product ratios of n-caprylate to n-caproate. The total accumulated MCC concentration is indicated by the size of the circle and the corresponding black text of n-caproate plus n-caprylate in g COD/L (pH 5.4±0.1, 12-d incubation). Four initial concentrations of ethanol were evaluated. In general, a higher initial concentration of ethanol led to a lower product ratio. Substrate inhibition was apparent at 28.8 g COD/L (300 mM) ethanol for all substrate ratios.

Even though production of n-caprylate has not yet been reported with pure cultures of *C. kluyveri*, it has so with microbiomes. We, therefore, performed a batch experiment with microbiomes at a mildly acid pH to ascertain whether substrate ratios would have an effect on product ratios with n-caprylate. In general, a higher ethanol-to-acetate ratio, indeed, resulted in a higher n-caprylate-to-n-caproate ratio (FIG. 4). For the fixed starting ethanol concentration of 9.6 g COD/L (100 mM), this was true in the batch experiments for the entire range of substrate ratios (yellow circles in FIG. 4 and FIG. 11A). Two other observations from this batch experiment are pertinent, though: 1) a higher initial ethanol concentration lowers the n-caprylate-to-n-caproate ratio for each ethanol-to-acetate ratio (FIG. 4). For the fixed ethanol-to-acetate ratio of 13.5 g COD/g COD this is most clear with a considerably lower n-caprylate-to-n-caproate ratio throughout the entire range of increasing initial ethanol concentrations (third column from left in FIG. 4 and FIG. 11B); and 2) ethanol is inhibiting n-caprylate production and not acetate (FIG. 4). For the relatively low, fixed acetate concentration of ~0.7 g COD/L (~10 mM) with increasing initial ethanol concentrations, the product ratios and the n-caprylate concentration first increased, but then decreased at the two highest initial ethanol concentrations (FIG. 11C). In fact, we observed a considerable inhibition at an initial ethanol concentration of 28.8 g COD/L (300 mM) ethanol without accumulation of the possible inhibiting undissociated MCCs (FIG. 11B-C). From this work it is clear that for microbiomes a positive correlation exists between the ethanol-to-acetate ratio and the n-caprylate-to-n-caproate ratio, but that the concentration of ethanol in the bioreactor should be maintained below inhibiting conditions.

Product extraction is needed to obtain high product ratios of n-caprylate to n-caproate. The highest n-caprylate-to-n-caproate ratio that we achieved with microbiomes in our batch experiments without extraction was 2.7 g COD/g COD with an ethanol-to-acetate ratio of 13.5. Because we used similar conditions: the same inoculum, a close substrate ratio of 15, and a mildly acidic pH, the much higher achieved substrate ratio of 25 during Period 8 with our continuous anaerobic bioreactor can only be explained by product extraction. Accordingly, we did observe an average n-caprylate productivity increase from 0.2 to 0.8 COD/L-d from Period 5 to Period 6 when product extraction was started on Day 98 without any other operating changes (Table 2).

To understand how product extraction can achieve such as large increase in product ratio, we should first discuss thermodynamics and product inhibition. A recently published thermodynamic model shows that a higher product ratio of n-caproate to n-butyrate is energetically favorable for C. kluyveri by releasing more ATP. In general, the longer the MCC that is produced, the more reduced the chemical is, and the more ATP is released, which is advantageous for chain-elongating bacteria. However, thus far, the n-caprylate-to-n-caproate ratio has been low, while n-caprate (C10) production has not been demonstrated. The considerably higher product inhibition from the longer MCCs in bioprocess systems can explain this, because a strong correlation exists between the length of the chain and its toxicity. The pH value in the bioreactor broth plays an important role because the undissociated MCCAs inhibit microbial activity with mildly acidic pH values for the pKa (4.88 for n-caproate and n-caprylate). The undissociated MCCAs (e.g. n-caproic acid, n-caprylic acid) are hydrophobic and their hydrophobicity increases for MCCAs with longer carbon chains. These MCCAs can, therefore, penetrate the hydrophobic lipid membranes of microbial cells and even damage cytoplasmatic structures. Previous work found such damage in enteric bacteria. However, the membrane integrities remained intact, pointing toward exhaustion from expelling protons to maintain a neutral pH in the cytoplasm as the mechanism of toxicity for MCCAs.

Researchers have used two different approaches to maintain low concentrations of undissociated MCCAs in the bioreactor broth with the overarching goal to overcome product inhibition and to increase MCC productivities. These two approaches from different operating conditions are: 1) a neutral pH value of 6.5-7.5 and relatively short HRTs; and 2) a mildly acidic pH value of 5.0-5.5 and in-line product extraction. Here, we used the second approach. When reactor microbiomes are used to chain elongate, it is important to completely inhibit acetoclastic methanogens to prevent acetate conversion into methane. We accomplished this by operating the bioprocess at a mildly acidic pH conditions. In addition to inhibiting methanogens, the mildly acidic pH conditions ensure a sufficient chemical gradient for product extraction from the bioreactor broth. Product extraction via pertraction is considerably more efficient with longer carboxylates that have a ~10× lower maximum solubility concentration in their undissociated form for each 2 carbons that are added. This results in faster extraction rates for n-caprylate compared to n-caproate and a selective pressure, and likely added to the explanation of why our continuous bioreactor with in-line extraction achieved such superior n-caprylate productivities and selectivities.

Before the slight over feeding conditions during Period 8, we observed MCC extraction efficiencies of 99.7% and 95.5% for n-caprylate and n-caproate, respectively. However, these efficiencies decreased to 98.9% and 89.6%, respectively, during Period 10 and then 96.6% and 89.4%, respectively, during Period 11 when the OLRs were increased (Table 3). The resulting decrease in efficiency and the ability of microbiomes to achieve considerably higher MCC productivities with ethanol and acetate as a substrate than in this Example, indicates that in-line product extraction was limiting the production rates of our bioreactor. Since the biological chain elongation rates were higher than the extraction rates, MCCs accumulated in the bioreactor broth (Period 10-11 in FIG. 3 and Table 2). Due to the mild acidic conditions of our bioreactor (pH=5.2), undissociated n-caprylic acid and n-caproic acid concentrations were relatively high (pKa=4.88), possibly reaching inhibiting concentrations. Together with high concentrations of ethanol it explains why the MCC productivity stagnated in Period 11 (FIG. 1). In a separate abiotic experiment, we observed that the flow rate of the broth recycle (and not of the mineral oil solvent nor of the alkaline extraction solution) was directly proportional to the overall mass transfer coefficient of n-caproic acid (FIG. 12). Therefore, we increased the MCC extraction rates, and thus the MCC productivities and the n-caprylate specificities, in our Example by increasing the recycling flow of the bioreactor broth through the forward membrane contactor (FIG. 8).

The Achieved Maximum Concentrations of n-Caprylic Acid and Ethanol were Inhibiting.

During Period 5 without product extraction, we observed maximum average undissociated n-caproic acid and n-caprylic acid concentrations of 0.27 g COD/L (1.1 mM) and 0.21 g COD/L (0.6 mM), respectively (FIG. 3A). These increasing concentrations of undissociated carboxylic acids resulted in the sudden increase in residual ethanol concentrations to ~0.5 g COD/L (5 mM) on Day 92 (FIG. 3B). Next, switching on the product extraction system on Day 98 in Period 6 instantly removed the accumulated MCCs, resulting in an almost immediate relief of the residual ethanol concentrations in the bioreactor (FIG. 3A). Clearly, the high concentrations of undissociated carboxylic acids caused microbial inhibition.

The maximum concentration of undissociated n-caproic acid of 1.1 mM during Period 5 is considerably lower than the maximum concentrations that other studies have observed with microbiomes. For example, in a previous report a maximum undissociated n-caproic acid concentration of 10.5 mM in the bioreactor broth with ethanol as the electron donor, which is 11% of the solubility limit of undissociated n-caproic acid (93 mM) was previously reported. At the same time, the maximum concentration of undissociated n-caprylic acid of 0.63 mM in our bioreactor broth during Period 11 is 13% of the solubility limit (4.7 mM) and is considerably higher than reported by previous studies (FIG. 13). From this comparative analysis, we postulate that accumulated undissociated n-caprylic acid was inhibiting our microbiome rather than n-caproic acid. This inhibition of undissociated n-caprylic acid was used as an ecological tool to enrich for n-caprylate-producing bacteria in the microbiome during Phase I. We had switched off the extraction on purpose to accumulate MCCAs during Period 4 after which, for the first time, the n-caprylate-to-n-caproate ratio increased (FIG. 3A). Predominantly chain-elongating bacteria survived such high concentrations of MCCAs.

The ethanol concentration in the bioreactor broth increased to an ultimate concentration of 33 g COD/L (350 mM) during Periods 10-11 (FIG. 3B), but did not reach 44 g COD/L (460 mM), which had previously been observed to be inhibitory in pure culture studies of the type strain *C. kluyveri*. Possibly inhibiting ethanol concentrations need to be taken into consideration because 33 and 44 g COD/L are considerably lower than the maximum ethanol concentration of ~100 g COD/L (1 M) in syngas-fermentation effluent. However, an efficient chain elongation system can maintain a very low ethanol concentration in the bioreactor broth (Periods 6-7) (FIG. 3B) or non-inhibiting ethanol concentrations for long operating periods[2] Our batch experiments with microbiomes at an initial ethanol concentration of 28.8 g COD/L (300 mM) indicate that the average residual ethanol concentration of 27.3 g COD/L (284 mM) during Period 11 would have likely caused substrate inhibition. From our results with batch and bioreactor experiments it is, therefore, apparent that both high undissociated MCCA concentrations and a residual ethanol concentration of ~300 mM will inhibit the microbial processes. Likely, some interaction between these different inhibitions will be present.

Microbiome analysis showed a surprising absence of the type strain *C. kluyveri*, We also investigated the microbiome dynamics during the operating period. We observed 1634 operational taxonomic units (OTUs) from high-quality sequence reads with 48 of these OTUs exceeding 1% of the relative abundance in one or more reactor microbiome samples during the entire operating period (FIG. 14). In addition, these 48 OTUs accounted for 88.1%-96.0% of the total high-quality sequence reads for each sample. A total of 36 OTUs exceeded 1% of the relative abundance in at least one sample for Phase II during which we observed high n-caprylate productivities. These 36 OTUs were hierarchically ranked based on both the average relative abundance and the abundance profile throughout Phase II. This resulted in the highest abundant OTUs at the bottom of the heat map (FIG. 5). OTUs for *Acinetobacter* spp. and a Rhodocyclaceae K82 spp. were predominant during Phase II. Between Days 140-150 during Periods 7-8, the relative abundance of the *Acinetobacter* spp. OTU decreased. On the other hand, the relative abundance of the Rhodocyclaceae K82 spp. OUT increased during Periods 8-10 with the highest MCC productivities of this Example. Next, the relative abundance of Rhodocyclaceae K82 spp. decreased during the overloading conditions of Period 11. We did not find a statistical correlation between the abundances for the OTUs of *Acinetobacter* spp. and of Rhodocyclaceae K82 spp. and the n-caprylate productivities (p>0.05). However, we did find such correlations for five OTUs with a much lower abundance in the microbiome (FIG. 5), including: 1) *Desulfosporosinus meridiei* (p=0.01); 2) *Oscillospira* spp. (p=0.02); 3) *Burkholderia* spp. (p=0.02); and 4-5) unknown Ruminococcaceae (p=0.002; p=0.04). While the type strain *C. kluyveri* is known to elongate acetate into n-caproate with ethanol as an electron donor, the highest relative abundant *Clostridium* OTU found in this Example was less than two percent during Phase I. Thus, the absence of *C. kluyveri* during Phase II, the lack of any pure-culture studies that reported n-caprylate as a product, and an optimum pH of 6.5-7.5, indicates that we have a different type strain for chain elongation to n-caprylate at mildly acidic conditions.

Figure 6:
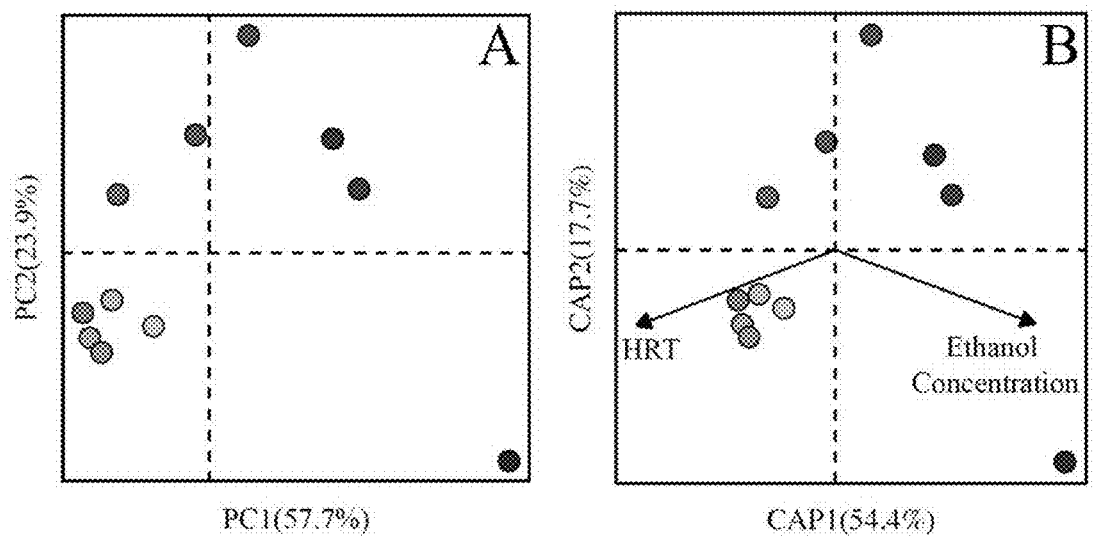
FIG. 6 shows beta diversity and constrained ordination for 11 microbiome samples during the high n-caprylate productivity of Phase II. Principal coordinates analysis (PCoA) (A) and capscale analysis (dbRDA) (B) were performed with sequence and performance data for 11 reactor microbiome samples. The increasing blue color of the circles for the 11 samples indicates the increasing length for the operating period of Phase II, including Day 106, 120, 126, 134, 140, 150, 155, 163, 174, 176, and 186. The five lighter blue circles (lower left quadrants) represent samples from early in Phase II (Periods 6-7), while the four darkest blue circles (right half) represent samples from the end of Phase II (Period 10-11). Average residual ethanol concentrations in the bioreactor broth and average hydraulic retention times (HRTs)

The number of OTUs within the community and their relative proportions did not vary considerably during the operating period (FIG. 15). The beta diversity, or dissimilarity of OTU composition between samples, showed a chronological path from earlier samples (lighter circles) to later samples (darker circles) for Phase II with a high n-caprylate productivity (FIG. 6A) and for the entire operating period including the inoculum (FIG. 16). The final sample from Day 186 (Period 11) was the most dissimilar sample during Phase II (darkest circle to the far right in FIG. 6A). To ascertain whether the operating conditions, environmental parameters, or functional performance affected the microbiome dissimilarity during Phase II with a high n-caprylate productivity, we performed constrained ordination. We found two parameters that explained 88% of the variation in the beta diversity during Phase II: 1) residual ethanol concentrations in the bioreactor broth (an environmental parameter); and 2) hydraulic retention time (and operating condition) (FIG. 6B), while the sample day number was not a significant (p>0.1) predictor of dissimilarity when considered in the model along with these two parameters. The presence of residual ethanol is, thus, important in shaping the microbiome, and clearly we had reached microbial inhibition with residual ethanol concentrations near 28 g COD/L (~300 mM) during Period 11 (FIG. 3B). In addition, we observed in Phase I that the n-caprylate concentration can be inhibiting the microbiome, however, we did not have enough samples for a statistically meaningful constrained ordination analysis. Finally, our work shows that the hydraulic retention time is an important parameter to shape the microbiome in our upflow anaerobic filter.

Conclusions. With a synthetic substrate of ethanol and acetate, which mimicked syngas fermentation effluent, we observed a sustained n-caprylate production via chain elongation with a reactor microbiome. The maximum n-caprylate productivity was 19.4 g COD/L-d at a product ratio of n-caprylate to n-caproate of 11 g COD/g COD. At a lower productivity, this ratio was even 25 g COD/g COD, resulting in a specificity of 96%. We obtained these results by combining: 1) a high substrate ratio of ethanol and acetate (15 g COD/g COD); 2) in-line product extraction; and 3) the selection of an acclimated microbiome form a sustained chain-elongating bioreactor. To our surprise, the type strain *C. kluyveri* was absent from the reactor microbiome. We found that both high residual concentrations of undissociated n-caprylic acid (0.62 mM) and ethanol (300 mM) inhibit microbial activity. In addition, residual ethanol concentrations affected the community structure of the microbiome during a period of high n-caprylate productivity. Syngas fermentation effluent represents a renewable source of ethanol and acetate at high substrate ratios for chain elongation. Upgrading the C2 molecules into predominantly C8 molecules by chain elongation represents a pathway to increase product value and reduce the energetic cost of product extraction from a biotechnology platform that includes syngas fermentation. Little to no methane is produced using this system Example 2

This example provides a description of methods and systems of the present disclosure.

A carboxylate bioreactor utilizing reverse beta oxidation has been shown in the past to produce significant levels of caproate and high levels of caprylate compared to other studies. The purpose of this Example is to examine the effects of influent molar ethanol to acetate ratios on the performance of an anaerobic bioreactor, in particular, the caprylate, caproate, and butyrate production rates. The bioreactor was initially fed media with an ethanol to acetate molar ratio of 10:1, 10:0 (only ethanol), 9:1, 8:2, 7:3, and 6:4. The reactor was operated for a period of about two weeks. The results suggest that higher ethanol to acetate ratios result in higher caprylate conversion efficiencies. This Example also demonstrated, for the first time, chain elongation in a continuously fed reactor using only ethanol as the substrate.

The goal of the Example is to experimentally examine the effects of the molar feed ratio of ethanol to acetate on the production of medium chain carboxylates in an anaerobic bioreactor more closely than has been done previously. The Example attempted to make use of previous work and verify the hypothesis that higher ethanol to acetate feed ratios results in higher caprylate production and caprylate specificity. The Example also tried to demonstrate that chain elongation and MCC production is possible using only ethanol as a substrate. 10.1241 Methods. Bioreactor Configuration, Setup, and Maintenance. The reactor that was used for the entirety of the experiment was custom designed and constructed. The reactor is an open culture, anaerobic bioreactor with a pertraction unit. The bioreactor itself is an open culture bioreactor that was originally inoculated with a population from a similar reactor that was fed corn beer.

Feed and Media. The feed of the bioreactor is composed of a synthetic version of the effluent expected from a syngas fermenter. The media is primarily composed of ethanol and acetate when included (as substrates for reverse beta-oxidation), a yeast extract, and tap water. Additional chemicals are used in lower concentrations, including chlorides, sulfates, phosphates, and various vitamins. The concentrations of ethanol and acetate are described later, in Experiment Design.

The feed is stored in a refrigeration unit which keeps the feed between 2 to 8 degrees Celsius. The influent is fed semi-continuously; it is kept on for 15 minutes and then kept off for 15 minutes. The feed pump was set to 1.6 L per day.

Bioreactor. The reactor is kept at both a steady pH of about 5.25 and a steady internal temperature of about 30 degrees Celsius. The pH is maintained by a pump that adds 0.5 M HCl when the pH falls out of range. Throughout the time of the experiment, the pH was kept at 5.25±0.10. The reactor is heated by a jacket that pumps heated water down the length of the cylindrical reactor. The jacket temperature is kept at about 40° C. +2° C., and the internal temperature of the reactor is kept at about 30° C. +1.5° C. For the duration of the following experiment, the reactor was kept at these temperatures, pH, and pump settings.

The bioreactor itself is filled with a packing material to promote biofilms. The bioreactors effective volume, taking into account the packing material, is ~0.7 L. A unit at the top of the reactor measures gas production.

Additionally, biomass samples were taken once per week, approximately twice per distinct feed ethanol to acetate ratio. Biomass samples were taken from the middle and bottom of the reactor. This procedure may have disturbed the ecological community of the bioreactor.

Pertraction Unit. The pertraction unit actively strips hydrophobic medium chain carboxylic acids from the reactor across a membrane into mineral oil with 30 g/L tri-n-octylphosphine oxide (TOPO). The loaded oil is then pumped to a second membrane pass where an alkali stripping solution deprotonates the acids into carboxylates, making them hydrophilic in the process. The hydrophilic carboxylates remain in the stripping solution as the unloaded oil returns to the first membrane. The membranes used to load and unload the oil are Liqui-Cel® Membrane Contractors, (product number S08057330; constructed in 2014). The membranes used to filter out particulates are Pentek GS-6 SED/5, Upper Saddle River, N.J., USA 5 micron sediment and rust particulate filters. The flow rate of the pumps used throughout the pertraction unit are set to 0.81 L/day.

The stripping volume of the reactor is maintained roughly at ~3.2 L. The stripping solution is kept above a pH of 9.00 by the use of a pump that adds 5M NaOH when the stripping pH falls below a pH of 9.00. The stripping solution is generally changed when the concentration of caprylate or another carboxylate is above 0.2M. The procedure for this event calls for turning off the stripping, pouring out most of the solution, leaving 0.45 L of the solution, and diluting that solution with DI water. Three times during the experiment the stripping solution was changed, on day 180, 201, and 222. For all three times, the new concentration after equilibrating was taken as zero and subsequent accumulation of carboxylates was added to the previous total.

Experimental Design. In order to observe the relationship between the molar ratio of ethanol to acetate in the feed to the production of medium chain carboxylates in an anaerobic bioreactor, the following experiment was designed. Using the bioreactor described in the passage above, the media fed to the reactor was composed of different ethanol to acetate molar ratios. During the first period of the experiment, the reactor was fed the molar ratio that it was fed for the previous months of 10:1 ethanol to acetate. After two weeks, the media would then be switched to a pure ethanol solution, while maintaining the same organic loading rate measured in g COD/L-day. Subsequently, the reactor feed ethanol to acetate molar ratio was decreased incrementally approximately every two weeks to 9:1, then 8:2, then 7:3, then 6:4, and finally 5:5 (the lowest possible feed that was previously determined to facilitate reverse beta oxidation). After dropping to a 5 to 5 molar ethanol to acetate ratio, the ratio will be increased for a brief time to 8 to 2 molar ratio, followed by a prolonged time of pure ethanol feed to achieve steady state. 10133 The initial feed of the system (10:1) was composed of 300 mM of ethanol and 30 mM of acetate. The corresponding total organic loading rate of the system for the entire experiment was calculated to be approximately 25 gCOD/L from a hydraulic retention time of about 1.3 days. The concentrations of ethanol and acetate in the feeds of the subsequent periods are listed below (Table 3).

TABLE 3

| EtOH:Ace (mol ratio) | Ethanol (mM) | Acetate (mM) | Days | Dates (2016) |
|---|---|---|---|---|
| 10 to 1 | 300 | 30 | 179-198 | Feb 11-March 1 |
| 10 to 0 | 320 | 0 | 198-208 | March 1-14 |

TABLE 3-continued

| EtOH:Ace (mol ratio) | Ethanol (mM) | Acetate (mM) | Days | Dates (2016) |
|---|---|---|---|---|
| 9 to 1 | 298 | 33 | 208-226 | March 14-29 |
| 8 to 2 | 274 | 68.5 | 226-240 | March 29-April 12 |
| 7 to 3 | 248.7 | 106.6 | 240-257 | April 12-29 |
| 6 to 4 | 221.3 | 147.6 | 257-275 | April 29-May 17 |
| 5 to 5 | 191.8 | 191.8 | 275- | May 17-present |

During the course of each period, samples were taken from the feed, the reactor broth, and the stripping solution of the bioreactor approximately four times a week. The concentrations of ethanol and the carboxylates were then determined by running the samples through two different GCs (solvents and VFAs respectively). The minimum limits of detection for the reactor broth concentrations were 0.05 gCOD/L for ethanol and about 0.02 gCOD/L for carboxylates. The minimum detection limits in the stripping was 0.02 gCOD/L for the carboxylates.

Over the course of the experiment, twice media was unsuccessfully added to the system. The first time, the temperature of the refrigerator dropped below freezing and the media froze in the middle of the 7:3 period. The media then melted and remained for the duration of the run. The second time was during the addition of the new 6:4 media, when the feed tubing was bent and feed did not flow to the reactor. The feed tubing was shortened and the media stayed for the remainder of the duration.

Three times during the experiment the stripping solution was changed, on day 180, 201, and 222 (10:1, 10:0, and 9:1 respectively). For all three times, the new concentration after equilibrating was taken as zero and subsequent accumulation of carboxylates was added to the previous total.

Calculations. A number of equations and methods were used to determine different variables:

Hydraulic retention time (HRT): The hydraulic retention time was determined by measuring the mass of effluent over a determined time. The effluent density was then approximated to be 1 gram per mL, and the hydraulic retention time was calculated by dividing the volume of the reactor (0.7 L) by the volumetric flow rate (proportional to mass divided by time).

Organic loading rate (OLR): The organic loading rate was determined by dividing the total concentration of the feed (the sum of ethanol, acetate, and yeast in g COD/L) by the hydraulic retention time (HRT).

Transfer Rate of carboxylates: The transfer rate of carboxylates was determined by first multiplying the concentration in the stripping by the volume of the stripping solution, resulting in gCOD. This data was graphed over time for the entire period. A linear regression was determined using Microsoft Excel's LINEST function. The slope (in gCOD/day) was then divided by the reactor volume, giving the transfer rate.

Effluent Rate of carboxylates: The effluent rate of the carboxylates was determined by averaging the concentration of the carboxylates in effluent and then dividing by the hydraulic retention time.

Production Rate of carboxylates: The total production rate is the sum of the transfer and the effluent rates for each respective carboxylate.

Conversion Efficiency: The conversion efficiency was found by dividing the production rate of the carboxylate by the organic loading rate.

Specificity of carboxylates: The specificity of a carboxylate was determined by dividing the production rate of the carboxylate by the sum of all of the production rates.

Pertraction Efficiency: The pertraction efficiency was determined by dividing the transfer rate of a carboxylate by the production rate of the carboxylate.

Confidence Intervals.

The 95% confidence intervals for the hydraulic retention time, organic loading rate, and effluent concentrations were determined by the following equation, where N are the samples:

$$Conf.\ \text{Interval} = \frac{STDEV.S(N)}{\sqrt{\text{Count}(N)}} * 1.96$$

The 95% confidence interval for the transfer rate was determined by finding the standard error of the slope approximation using Excel's LINEST function and multiplying it by 1.96 (the t-value of a 95% confidence interval).

The 95% confidence intervals for the effluent rate and conversion efficiency, as they are the product of two variables (one being an inverse), was determined by the following equation.

$$Conf.\ \text{Interval} = 1.96 * \sqrt{a^2 * \left(\frac{2*conf,b}{3.92}\right)^2 + b^2 * \left(\frac{2*conf,a}{3.92}\right)^2}$$

It is assumed in the equation above that the two variables (a and b) are independent for simplicity, which is not necessarily true.

For the production rate, being the sum of two variables, the confidence interval was determined with the following equation:

$$Conf.\ \text{Interval} = 1.96 * \sqrt{\left(\frac{2*conf,a}{3.92}\right)^2 + \left(\frac{2*conf,b}{3.92}\right)^2}$$

Discussion. The results of the following experiments clearly demonstrate a link between the molar ratio of ethanol to acetate in the feed and the production of higher carbon density medium chain carboxylates by reverse beta oxidation. As the molar ratio of ethanol to acetate in the feed was decreased, the conversion efficiency, specificity, and production rate of caprylate decreased rather dramatically and noticeably. Conversely, the conversion efficiency, specificity of butyrate increased as the molar ethanol to acetate ratio decreased. Being in between butyrate and caprylate in the reverse beta oxidation chain elongation reaction, it was predicted that initially the production rate of caproate would go up while the production rate of caprylate went down followed by the rate of caproate production going down itself. This result can be seen in FIGS. 21, 25, 26, and 28.

The maintained high pertraction efficiency for caprylate and the high caproate pertraction efficiency in the lower ethanol to acetate ratios (FIG. 29 and Table 3) and the either constant or decreasing concentrations in the effluent (FIGS. 22 and 23) together show that the production of these MCCs are most likely not limited by the mass transfer across the membranes into the stripping, but instead are limited by the production rates of the bacterial communities themselves.

In addition to the increasing caproate production and conversion from a feed ratio of 10:0 to 8:2, the overall production rate of MCCs increase from 10:0 to 9:1 to 8:2. This results in the maximum production rate of carboxylates (outside of the initial 10:1 period) coming when the feed was an 8:2 molar ratio of ethanol to acetate. After this point, the total production and conversion of carboxylates starts to go down. During this time, caproate production is increasing faster than caprylate production is decreasing, and after the 8:2 ratio, caproate and caprylate production is decreasing faster than butyrate is increasing. It should be noted that the pertraction efficiency of butyrate is significantly lower than caprylate or caproate for the entirety of the experiment. It is possible that the stripping solution cannot strip the broth (which the stripping was intended for MCCs), and evidence of this can be seen in FIG. 22 as the broth concentration of butyrate continually increases.

Reverse Beta Oxidation and Pure Ethanol Feed.

The results of the experiment demonstrate the kinetics of reverse beta oxidation and in the future could be analyzed further. The initiation of reverse beta oxidation is limited by the ethanol and acetate substrates. When acetate concentrations are sufficiently low enough to slow down the initiation of a new carboxylate by reverse beta oxidation, the high ethanol concentrations of the environment would continue to facilitate the propagation of reverse beta oxidation by the oxidation of ethanol, extending the carboxylates. As seen in FIG. 20, as the switch to pure ethanol decreases the concentration of butyrate and caproate, caprylate concentrations remain relatively unaffected.

Additionally in the pure ethanol feed ratio, it appears in FIG. 20 as though the concentration of acetate increases while caproate and butyrate go down. An explanation is that in the absence of acetate from their environment, the bacteria may have responded by increasing the production of acetate before reaching a steady state.

It should be noted further that this experiment not only gives evidence that a pure ethanol feed could work for a carboxylate bioreactor, but in fact that it is effective in giving higher carbon density carboxylates.

Comparisons to Other Studies with 10:1 Molar Ethanol to Acetate Ratios.

The results of the period before moving to the pure ethanol feed are interesting in comparison to previously reported results attained by similar feed ratios. The conversion efficiency of caprylate from the results of the previously reported experiments (68.7%) was in fact higher than the conversion efficiency of caprylate (55.9%) from the conditions that gave the highest reported caprylate production rate at an OLR of 34.7 gCOD/L-day. The conversion efficiency found here though is lower than the conversion efficiency (70.7%) which provided the highest caprylate to caproate production ratio in the previously reported (25:1 based on g COD) at an OLR of 15.0 g COD/L-day. The total conversion efficiency of medium chain carboxylates during the pre-experiment phase (83.5%) was higher than previously reported production of caprylate to caproate ratios (60.8% and 73.3% respectively).

Example 3

This example provides a description of methods and systems of the present disclosure.

Our bioreactor had been batch-fed semi-continuously through an operating period of 4 years. We used the carboxylate platform to convert the corn beer fermentation broth to medium chain carboxylic acids (MCCAs). In the fourth year, we performed no experiments, and solely operated the bioreactor to keep the biomass active. More surprising, yet, was that the production rate of n-caprylate (C8) was several times higher than previously, and higher than n-caproate (C6) because the pH of bioreactor broth had jumped from 5.5 to 6.75. Accordingly, we studied the effect of pH on the product rate of n-caproate and n-caprylate from corn beer (ethanol) fermentation with a 5-L anaerobic sequencing batch reactor (ASBR) with continuous pertraction (membrane-based liquid-liquid extraction).

The operating period consisted of five experimental phases based on different pH levels in the bioreactor (5.5, 6.0, 6.25, 6.75 and 7.0). We started with a pH of 6.75, and then decreased the pH to 6.25 and then to 5.5. After those phases were completed, we increased the pH again to 6.0 and then to 7.0. Each phase was operated for at least 3 hydraulic retention times (HRTs) after the system was found to operate in a stable performance. During all phases, the temperature of ASBR was controlled at 30±1° C. by circulating heated water through an external heating jacket of the glass bioreactor. The bioreactor was fed semi-continuously (every 2 days) with corn beer fermentation broth (containing yeast). That was diluted with tap water (diluted 3.4 times). The hydraulic retention time (HRT) was 15 days. The organic loading rate (OLR) of system was 7.66 g COD L$^{-1}$ d$^{-1}$ for the phase with a pH of 6.75 and 6.92 g COD L$^{-1}$ d$^{-1}$ for the rest of the 4 phases. The MCCAs were recovered from the bioreactor using a pertraction system (liquid-liquid extraction) similar to previous reports.

The production rate of n-caprylate decreased gradually from 1.47±0.05 to 1.1±0.01 g L$_{bioreactor}^{-1}$ day$^{-1}$ when the pH of bioreactor decreased from 6.75 to 6.25, and then to 0.73±0.13 g L$_{bioreactor}^{-1}$ day$^{-1}$ at a pH of 5.5. When we subsequently increased the pH again from 5.5 to 6.0 and then to 7.0, the production rate of caprylate increased again, reaching 1.1±0.15 g L$_{bioreactor}^{-1}$ day$^{-1}$ and 1.49±0.11 g L$_{bioreactor}^{-1}$ day$^{-1}$ respectively (FIG. 31A). This indicated that between a pH of 5.5 to 7.0 that we tested, the highest n-caprylate production occurred at the highest pH levels.

In the broth, the concentration of n-caprylate decreased gradually from 51.3±2.6 to 2.55±0.54 mM when pH decreased from 6.75 to 5.5. Expectedly, the concentration of n-caprylate increased from 2.55±0.54 mM to 25.5±1.4 mM when pH was increased from 5.5 to 7.0 (FIG. 31B). Similarly, the concentration of total combined MCCAs in the broth was lowest (21.6±1.8 mM) during the period of pH 5.5 in bioreactor.

At the end of each phase, we lowered the pH of the stripping solution with sulfuric acid, which spontaneously separates the MCCA oil from the stripping solution through phase separation. The main components of the MCCA oil were n-caproic acid and n-caprylic acid (other fatty acids were not detected, ≤GC detection limit: 0.12 mM). The results showed that the molar percentage of n-caprylate gradually increased from 75% to 97% when pH of bioreactor increased from 5.5 to 7.0 (FIG. 32).

In summary, the highest relative n-caprylate production occurred at the highest pH level of 7.0, while the highest relative n-caproate production occurred at the lowest pH of 5.5 (less green in FIG. 31). This can be explained by the differences for both the toxicity and the extraction rates between undissociated n-caprylic acid of n-caprylic acid at different pH levels (and their interactions). Since the pKa of n-caproate and n-caprylate is around 4.9 (and possibly a bit higher due to micel formation in the bioreactor, especially for n-caprylate), the relative level of undissociated acids is higher at the lower pH levels of the Example. Undissociated n-caproic acid and n-caprylic acid are highly toxic to the community, especially for n-caprylic acid that is toxic at an approximately 10× lower concentration than n-caproic acid, while the dissociated salt is not toxic at all. That is why we operate in-line extraction systems for our bioreactors to keep the concentrations in the bioreactor (and thus effluent) to a minimum. Therefore, at the lower pH levels in this Example n-caproate would not be further converted to n-caprylate as much due to high toxicity problems for n-caprylic acid than at the higher pH levels.

At the same time, the extraction rates for undissociated n-caprylic acid are much higher than for undissociated n-caproic acid due to the much more oily nature of n-caprylic acid compared to n-caproic acid (the maximum solubility concentration is about 10× lower for n-caprylic acid compared to n-caproic acid). Pertraction of n-caproic acid has to occur at the lower pH levels. We found here that n-caprylic acid can be extracted at a pH of 7. It is possible that the observed pKa is higher in our bioreactor for n-caprylic acid due to micel formation, but this does need to be investigated further. Therefore, only the longer chemical (C8) n-caprylic acid can be extracted at a pH of 7.0 (97% in FIG. 32) and automatically the system selects for this n-caprylic acid production at the higher pH levels. Thus, both the lower toxicity of n-caprylic acid and the higher extraction of n-caprylic acid compared to n-caproic acid at the higher pH levels explain why the relative production of n-caprylate is preferred at a neutral pH compared to a midly-acidic pH.

We had operated the bioreactors at a mildly acidic pH level of 5.5 (or even lower) in the past to prevent acetoclastic methanogens to convert all substrate and ethanol into methane. Thus, at a pH of 7.0 we would have anticipated a methanogenic anaerobic digester rather than a chain elongating bioreactor. Through separate experimentation with small serum bottles we found that the concentrations of undissociated n-caprylic acid were toxic to these methanogens. This explains why we can chain elongate at the higher pH levels without adding a methanogenic-inhibiting compound such as bromo-ethanesulfonate (BrES). We added anaerobic digester biomass from an active digester to the pH 7 bioreactor and we did not observe a shift to a methanogenic system even after waiting one month (no change). This substantiates the claim that we can operate a chain elongating bioreactor sustainably at a pH level of 7.0.

Example 4

This example provides a description of methods and systems of the present disclosure.

In this example, we examined the effect of different ethanol-to-acetate substrate molar ratios on the production of medium chain carboxylates. Higher ethanol-to-acetate substrate molar ratios led to higher selectivity for n-caprylate. The highest n-caprylate selectivity in this Example occurred when the substrate contained primarily ethanol (ethanol-to-acetate molar ratio >100), however, the overall medium chain productivity of the bioreactor declined. At an approximately one to one substrate molar ratio, n-caprylate production stopped in the bioreactor. Finally, Illumina 16S rRNA gene sequencing of the bioreactor microbiome across time and in two sampling locations on the bioreactor revealed a relatively uneven microbiome that was dominated by Firmicutes and Proteobacteria phyla members.

Here, our main objective was to experimentally determine what substrate ethanol-to-acetate ratio was optimal to promote n-caprylate production in a continuously operated bioreactor with product extraction. In addition, this Example aimed to investigate whether n-caprylate could be produced from primarily ethanol in the substrate (i.e., ethanol-to-acetate substrate molar ratio >100). A previously published thermodynamic model was extended in this example to n-caprylate and the experimental data collected was used to validate the model. Finally, this example sed Illumina 16S rRNA gene sequencing to investigate what OTUs were present in the bioreactor microbiome during the operating period and correlated the relative abundance of these OTUs with n-caprylate specificities.

MATERIALS AND METHODS. Bioreactor Setup. The bioreactor system that was operated in this example was also used in other examples and is described herein. Briefly, an upflow anaerobic filter (working volume 0.7 L) was operated with a continuous in-line, membrane-based liquid-liquid extraction (i.e., pertraction) system. The feed rate used in this Example was approximately 0.6 L d$^{-1}$, while the system recycle flow rate was 130 L d$^{-1}$, which resulted in a recycle feed ratio of over 200. The pH of the bioreactor broth was maintained at 5.26±0.09 via addition of 0.5 M hydrochloric acid to the well-mixed feed and recycle inlet at the base of the bioreactor. The temperature of the bioreactor was maintained at 30±1° C. The hydraulic retention time used in this Example was ~1.2 days. The pH of the alkaline extraction solution was maintained at 9.48±0.34 via addition of 5 M sodium hydroxide.

Growth Medium and Inoculum. The growth medium used in this Example is known in the art and has been described previously. For each operating period, the substrate concentrations of ethanol and acetate were varied to achieve the targeted substrate molar ratios of ethanol and acetate, while maintaining organic loading rates in the range of 18.7 to 28.2 g COD L$^{-1}$ d$^{-1}$ (Table 4). As mentioned above, this bioreactor microbiome was also used in another example described herein. No new inoculum was added to the bioreactor between studies.

TABLE 4

Operating data for the bioreactor. Average hydraulic retention time (HRT), influent ethanol and acetate concentration, substrate molar ratios (ethanol-to-acetate), and organic loading rates (OLR) per period are reported as mean ± s.e.

| Period | Days | HRT | Substrate Molar Ratio | Ethanol (mM) | Acetate (mM) | OLR (g COD L$^{-1}$ d$^{-1}$) |
| --- | --- | --- | --- | --- | --- | --- |
| Period 1 | 155 to 198 | 1.2 ± 0.02 | 7.8 ± 0.65 | 200.42 ± 9.42 | 25.68 ± 1.75 | 18.72 ± 0.81 |
| Period 2 | 198 to 211 | 1.17 ± 0.05 | 183.29 ± 38.86 | 289.14 ± 3.64 | 1.58 ± 0.33 | 25.15 ± 1.1 |
| Period 3 | 211 to 227 | 1.27 ± 0.07 | 11.29 ± 1.38 | 281.97 ± 5.21 | 24.97 ± 3.01 | 23.88 ± 1.43 |
| Period 4 | 227 to 240 | 1.16 ± 0.04 | 4.45 ± 0.29 | 281.69 ± 10.5 | 63.35 ± 3.35 | 28.17 ± 1.24 |
| Period 5 | 240 to 257 | 1.17 ± 0.04 | 2.43 ± 0.17 | 228.81 ± 10.65 | 94.09 ± 4.74 | 25.19 ± 1.18 |

TABLE 4-continued

Operating data for the bioreactor. Average hydraulic retention time (HRT), influent
ethanol and acetate concentration, substrate molar ratios (ethanol-to-acetate),
and organic loading rates (OLR) per period are reported as mean ± s.e.

| Period | Days | HRT | Substrate Molar Ratio | Ethanol (mM) | Acetate (mM) | OLR (g COD L$^{-1}$ d$^{-1}$) |
|---|---|---|---|---|---|---|
| Period 6 | 257 to 275 | 1.2 ± 0.05 | 1.93 ± 0.08 | 216.13 ± 5.26 | 111.83 ± 3.41 | 24.63 ± 1.08 |
| Period 7 | 275 to 291 | 1.2 ± 0.04 | 1.22 ± 0.06 | 177.87 ± 4.53 | 146.25 ± 6.24 | 23.34 ± 0.85 |

Bioreactor Operation. In the main phase of this example, we operated the bioreactor at the following substrate (ethanol-to-acetate) molar ratios: 7.8, 137.6, 11.3, 4.5, 2.5, 1.9, and 1.2 (Table 4). We operated the bioreactor at each ratio for a period of at least two weeks (at least 11 HRTs). Following the loss of performance at the 1.2 molar ratio, we ran another set of similar substrate molar ratios: 3.4, 4.4, and 90.1. The HRTs and OLRs for these later molar ratios, which are not the main focus of the paper, can be found in Table 5.

Liquid and Gas Analysis. Liquid samples (1.5 mL) were collected from the bioreactor influent, the bioreactor broth, and the alkaline extraction solution, as has been described in Example 1. Analysis of the samples to determine carboxylate and ethanol concentrations was carried out by gas chromatography using previously reported methods. The concentrations of methane, carbon dioxide, and hydrogen gases (detection limit 0.2%) were measured using a previously known GC method/system.

Calculations and Statistical Analysis of Operational Data. Carboxylate production rates are calculated as the average values for each operating period. Average effluent production rates (g COD L$^{-1}$ d$^{-1}$) and average transfer rates via product extraction (g COD L$^{-1}$ d$^{-1}$) were summed to yield the total production rates (g COD L$^{-1}$ d$^{-1}$). COD stands for chemical oxygen demand. Standard errors were reported. The average effluent production rates were calculated by dividing the average carboxylate concentration per period by the average HRT for that period. The average HRT per period was calculated based on the average influent flow rate per period, which was determined volumetrically. The average transfer rates were calculated by first plotting the increasing concentrations of the individual carboxylates in the alkaline extraction solution vs. time. Then the linear model function, lm, in R was used to determine the slope and standard error of the best-fit line through these points. The slope was then divided by the bioreactor working volume (0.7 L) to get the average transfer rate per period. We calculated the conversion efficiency as the individual carboxylate total production rate divided by the organic loading rate per period. In addition, specificity was calculated as the individual carboxylate total production rate divided by the combined total production rate for all carboxylates during each period (where the carboxylates included are n-butyrate, n-caproate, and n-caprylate). Furthermore, pertraction efficiency was calculated as the average transfer rate divided by the total production rate for each carboxylate. Finally, RStudio (version 1.0.136) was used for all data analyses.

Thermodynamic Model Development. Here, we extended a previously published generalized stoichiometric model to predict the thermodynamic favorability of n-caprylate formation at different substrate molar ratios. FIG. 33 shows the extended model. Details on the model development can be found herein under the section entitled "Thermodynamic Model Development". Briefly, the model uses stoichiometric relationships to predict the moles of caprylate and the amount of ATP that would be produced based on the moles of ethanol and acetate provided to the system. For the purpose of this model, the moles of n-butyrate and n-caproate formed were also fixed, to variables "b" and "c", respectively. The boundary for the metabolic flux was set to 10 moles of ethanol and acetate combined (therefore by setting moles of ethanol is equal to "a" in the model, moles of acetate is set to "10-a"). Based on this stoichiometry and the ethanol and carboxylate concentrations measured in the bioreactor, the Gibbs free energy of the reaction is calculated as well as the Gibbs free energy required for ATP formation. If the Gibbs free energy of the reaction was more negative than the Gibbs free energy required for ATP formation, the reaction was deemed feasible.

Microbial Community Analysis. We collected biomass samples for Illumina 16S rRNA gene sequencing analysis from the bottom and middle of the bioreactor approximately weekly throughout the operating period. The method of collecting biomass samples from the bioreactor broth has been previously described with the exception that, in the previous study biomass samples were only collected from the middle of the bioreactor, whereas in this Example we also collected them from a bottom sampling port. Pelleted biomass samples were stored at ~80° C. until further processing. Genomic DNA was extracted using the PowerSoil-htp 96 Well Soil DNA Isolation kit (MO BIO Laboratories Inc., Carlsbad, Calif.) according to the protocol of the manufacturer. The DNA amplification protocol was described previously with the following exceptions: Mag-Bind RxnPure Plus magnetic beads solution (Omega Biotek, Norcross, Ga., USA) was used instead of Mag-Bind E-Z Pure and 50 ng DNA per sample was pooled instead of 100 ng. It should be noted that duplicate PCR reactions of each DNA extract were performed and pooled prior to sequencing. Paired-end reads were joined in QIIME version 1.9.1 using the joined_paired_ends.py script and then the joined reads were uploaded to QIITA (qiita.microbio.me) for further processing. The sortmerna method was used to bin sequences in operational taxonomic units (OTUs) at 97% identity. Taxonomy was assigned for representative sequences selected for each OTU using the Greengenes v13.8 database from August 2013. The remaining analyses were performed locally in QIIME v1.9.1 and RStudio v1.0.136. Singletons were removed from the dataset resulting in 932 unique OTUs.

Alpha diversity was analyzed via Gini coefficient, observed OTUs, and Shannon diversity. In addition, heat maps were created to represent OTU relative abundance via the gplots package in R. Correlations of OTU relative abundance with n-caprylate specificities was investigated using the Spearman's rank correlation coefficient via the Hmisc package in RStudio. Correlations with p>0.001 were considered significant. Only OTUs that reached at least 1% relative abundance in any one bioreactor sample were considered in the correlation analysis.

Sequences were submitted to EBI under the following accession number. Sequences and study metadata are publically available in QIITA, which is an open-source microbiome storage and analysis resource.

RESULTS AND DISCUSSION. Higher Ethanol-to-Acetate Molar Ratio in Substrate Leads to Higher N-Caprylate Specificity. We observed that higher ethanol-to-acetate molar ratio in the substrate led to higher n-caprylate specificity in the products of the bioreactor (FIG. 34, Table 6). Here n-caprylate specificity is defined as the production rate of n-caprylate vs. the combined production rates of n-butyrate, n-caproate, and n-caprylate on a COD basis. The highest n-caprylate specificity achieved in this example was 82±10% at the highest substrate molar ratio tested, 183.3±38.9 (Table 6). To our knowledge, this is the highest substrate molar ratio that has been tested in the literature for medium chain carboxylate production. At the lowest substrate molar ratio used in this Example (i.e., 1.2±0.1 moles of ethanol per moles of acetate), n-butyrate production and specificity was much higher than at the higher substrate molar ratios tested, while no n-caprylate production was observed (FIG. 34, Table 6).

With the exception of Period 1, we decreased the substrate molar ratio during the operating period from 183.2 in Period 2 to 1.22 in Period 7. When the substrate molar ratio of ethanol to acetate decreased, acetate and n-butyrate concentrations increased in the effluent of the bioreactor (FIG. 35 and Table 7). In Period 2, at the highest substrate molar ratio (183.3±38.9) used in this example, the average acetate and n-butyrate concentrations measured in the effluent leaving the bioreactor were 4.1±0.6 mM and 3.6±0.9 mM, respectively (FIG. 35, Table 7). As the substrate molar ratio was decreased throughout the course of the Example (Periods 2 to 7), the acetate and n-butyrate concentrations in the bioreactor increased. At the lowest substrate molar ratio employed in this Example (1.2±0.6) in Period 7, the average acetate and n-butyrate concentrations in the effluent were 88.2±8.4 mM and 18.3±0.9 mM, respectively (FIG. 35, Table 7). Since the bioreactor had a high recycle ratio of ~220 (broth recycle flow rate divided by effluent flow rate), the concentration leaving in the effluent can be considered roughly equivalent to the concentration in the bioreactor.

We extended a previously reported hermodynamic model to predict the thermodynamic favorability of n-caprylate formation at the different ethanol-to-acetate ratios experienced by the bioreactor microbiome. Since the bioreactor was well-mixed, we used the average measured effluent concentrations (FIG. 35, Table 7) in this model to represent the closest approximation of the conditions the microbiome saw. Similar to a previously observed trend for n-caproate, our model predicted that higher ethanol-to-acetate ratios experienced by the microbiome generally lead to more favorable thermodynamic conditions for chain elongation to n-caprylate (FIG. 38). In other words, the Gibbs free energy of the n-caprylate formation reaction was more negative than the Gibbs free energy required for ATP production at the substrate molar ratios of 183.3, 11.3, and 4.4 (which resulted in ethanol-to-acetate ratios measured in the bioreactor of 16.4, 7.0, and 3.1, which we used in the model), indicating that the formation of n-caprylate was thermodynamically feasible at these ratios. For the most part, our model described what we observed experimentally, with the exception of the first period of the Example. In Period 1, when the substrate molar ratio was 7.8±0.7, the n-caprylate conversion efficiency was the highest achieved in our Example (68±7%) (Table 8) and the ethanol concentration leaving in the effluent was low at 15.6±1.0 mM (Table 7). The relatively faster conversion rate of ethanol in this period resulted in a relatively lower ethanol-to-acetate molar ratio measured in the effluent of 3.0 (Table 7). At this ethanol-to-acetate molar ratio and the observed concentrations of n-butyrate, n-caproate, and n-caprylate, our model predicted that n-caprylate formation becomes thermodynamically feasible (FIG. 38), even though we observed the highest n-caprylate production rates in this period (Table 9). Our model is an over simplification of what occurred in the bioreactor and does not represent what the microbes see. In addition, our thermodynamic model does not account for the kinetics in the bioreactor system. The model also does not account for effect of the continuously operating pertraction system, which was continuously and preferentially removing longer chain carboxylates from the bioreactor environment.

N-Caprylate Production with Primarily Ethanol in Substrate but Lower Overall Productivity. The highest substrate molar ratio resulted in the highest n-caprylate specificity (FIG. 34), as well as the highest n-caprylate to n-caproate productivity ratio of 5.9±0.7 (Table 6). However, it did not result in the highest conversion efficiency (Table 8). In fact, in this period (Period 2), the n-caprylate conversion efficiency (43±5%) was lower than in Period 1 under the 7.8 substrate molar ratio, where the n-caprylate conversion efficiency was 68±7% (Table 8). During Period 2, the ethanol concentration increased in the effluent of the bioreactor (FIG. 35B). The concentration remained well below the concentrations that have previously been found to be inhibitory. However, it is clear that excess ethanol was not being fully utilized by the bioreactor. Similar to the results in this Example, it was also found in Example 1 that a lower n-caprylate productivity in the period where the highest n-caprylate to n-caproate productivity ratio was observed. Thus, it appears that at higher ethanol-to-acetate molar ratios there is a trade-off between improved n-caprylate specificity and decreased overall productivity. In this Example, relatively short HRTs (i.e., 1.2 days) were employed. A longer HRT may allow for improved production at these higher ethanol-to-acetate substrate ratios, because less product is washed out.

n-Caproate and n-caprylate contain six or eight carbon atoms in their chain, respectively. Thus they are relatively hydrophobic and easy to extract from solution, as compared to n-butyrate. Indeed, it can be seen that the average extraction efficiency per period for n-butyrate ranged from a minimum of 11.8% to a maximum of 66.8%, whereas the average extraction efficiency for n-caproate per period was always greater than 65% and for n-caprylate was always greater than 96% in the periods where n-caprylate production was detected (Table 10). Due to the high extraction efficiency for n-caprylate that we observed in this Example, it is unlikely that are n-caprylate production rates were limited by mass transfer limitations.

Microbiome Shifts Correlated to N-Caprylate Specificity. We performed a time-series analysis of the microbiome that was sampled from two locations in our bioreactor: a bottom and a middle sampling port. We used Illumina 16S rRNA gene sequencing to analyze the samples. Similar to the microbial community stratification that has previously been observed in upflow anaerobic sludge blanket reactors, we observed clear differences in the compositions of the microbiomes sampled from the bottom and the middle of the bioreactor. The majority of samples from the bottom of the bioreactor had a higher relative abundance of the phylum Firmicutes compared to the phylum Proteobacteria, whereas the reverse was true in the middle of the bioreactor (FIG. 39). In addition, the bottom of the bioreactor had a more diverse microbiome as indicated by the Shannon diversity index and Gini coefficient (Table 11). Though the bioreactor was well-mixed due to the high recycle rate employed, it is unlikely that the ethanol and carboxylate concentrations were uniform throughout the bioreactor. Substrate and acid (0.5M HCl) for pH control were added at the base of the bioreactor, which may have caused slightly higher concentrations of un-dissociated carboxylic acids and ethanol to be seen by the microbes at the bottom of the bioreactor, as compared to the middle. Nevertheless, we did observe common OTUs between the middle and the bottom bioreactor samples, which are indicated on the heat maps (FIGS. 36 and 37). Of the OTUs that reached over one percent relative abundance in the bioreactor samples from the bottom and middle of the bioreactor (40 and 45 OTUs, respectively) and are shown in the heat maps, 28 of these OTUs were shared between the two sampling locations.

For both the bottom and the middle of the bioreactor, we examined which OTUs were positively or negatively correlated with n-caprylate specificities based on Spearmans rank coefficient (p<0.001) (FIGS. 36 and 37). Some common patterns emerged between the two sampling locations. Two different OTUs belonging to the family Ruminococcaceae were positively correlated to n-caprylate specificities in one of the two locations (OTU ID 720944 in the middle; OTU ID 300620 in the bottom). In addition, a Veillonellaceae family OTU (ID 225954) and an *Oscillospira* OTU (ID 4386437), which belongs to the Ruminococcaceae family, were positively correlated to n-caprylate specificities in both locations. Members of the Ruminococcaceae family, specifically the *Clostridium* cluster IV, including *Oscillospira*, have been found to be associated with: 1) n-butyrate production in the human gut, 2) n-caproate production from lactate in Chinese strong liquor fermentation, and 3) n-caproate, n-caprylate, and trace amounts of n-decanoate production from biorefinery thin stillage. Another OTU that is in the *Clostridium* cluster IV, an OTU belonging to the *Anaerofilum* genus (ID 130679), was also positively correlated to n-caprylate specificities in our bioreactor, though it was only seen in the bottom bioreactor samples. In Example 1, using the same bioreactor, members of the Ruminococcaceae family (the same OTUs as ones mentioned above that were positively correlated in this Example—IDs 720944 and 300620), as well as an OTU classified to *Oscillospira* genus level were also found to be positively correlated with n-caprylate productivity (the *Oscillospira* OTU (ID 115035) found in Example iwas also found in middle and bottom bioreactor samples but was not found to be correlated to n-caprylate specificity). In Example 1, biomass samples were only collected from the middle of the bioreactor.

Common patterns were also observed between the bottom and middle of the bioreactor in terms of which OTUs were negatively correlated with n-caprylate specificities. Different OTUs classified as *Acetobacter* spp. (OTU ID 4333237 in the bottom and OTU ID 635373 in the middle), a *Desulfosporosinus meridiei* OTU (ID 3406110), a *Lactobacillus zeae* OTU (ID 73609), and an OTU in the family Xanthomonadaceae (ID 588916) were negatively correlated with n-caprylate specificities. In the middle of the bioreactor, a *Methanobacterium* OTU (ID 2508129) was found to be negatively correlated to n-caprylate specificities. *Acetobacter* is an obligate aerobe that can convert ethanol to acetic acid. In was observed that *Acetobacter* in survived in the anaerobic bioreactors and it is possible that their survival could be due to trace amounts of oxygen entering in the non-anaerobic feed because we did not attempt to make the feed line completely anaerobic. It was observed that the populations of *Lactobacillus* and *Acetobacter* spp. declined and the overall medium chain carboxylate productivity of the bioreactor increased. This observation may be due to the substrates used (ethanol, acetate, and basal media).

Bioreactor System Unable to Recover Performance After Low Substrate Ratio. Following the lowest substrate ratio 1.2 moles ethanol to moles acetate, the bioreactor never recovered to its prior level of performance. In Period 8 (following low ratio), the substrate molar ratio was increased to 3.38. Despite the increase in the substrate molar ratio, the n-caprylate productivity did not recover to previous levels (Table 9). Medium chain conversion efficiency for this period was only 19.6±2.1% (Table 8). In this period, gas production began to increase. Across the main periods of the Example (Periods 1 to 7) the average gas production was 0.38±0.01 mL d$^{-1}$. In Period 8, the gas production increased to 1.22±0.06 mL d$^{-1}$, and by Period 11 the gas production increased to 2.74±0.04 mL d$^{-1}$ (Table 12). It is possible that at the low substrate molar ratio in Period 7 (1.2), methanogens were able to take over the system and shift the bioreactor away from medium chain carboxylic acid production.

The microbiome in this bioreactor is shaped to efficiently produce medium chain carboxylates by lowering the pH and using product extraction. In a previous study, which used a similar setup to produce medium chain carboxylates from corn beer, it was observed that higher n-caproate productivity correlated with a more uneven microbiome. Similarly the community in our bioreactor was relatively uneven (Table 11). Shaping the bioreactor to produce medium chain carboxylates at high rates and efficiencies may come at the price of decreased bioreactor stability, since it took so long to regain stability. Work is needed to further study these observations, and to find operating conditions that can mitigate this problem of this non-resistant community.

Conclusions. In conclusion, this Example demonstrated that higher ethanol-to-acetate substrate molar ratios lead to higher n-caprylate specificities. At very low ethanol-to-acetate substrate molar ratio (~1), no n-caprylate production was observed. To our knowledge, this is the first Example to demonstrate efficient n-caprylate production from primarily ethanol in the substrate (i.e., ethanol-to-acetate molar ratio greater than 100), though it should be noted that the n-caprylate conversion efficiency was lower at this ratio than at lower ratios tested. This Example also characterized the microbiome present at the different substrate molar ratios tested and examined which microbes were correlated with improved n-caprylate specificity in the bioreactor.

SUPPLEMENTARY METHODS. Thermodynamic Model Development. As mentioned herein, the previously published generalized stoichiometric model predicted the thermodynamic favorability of n-caproate formation at different ethanol-to-acetate substrate molar ratios. In this Example, we extended the model to predict n-caprylate formation at different ethanol-to-acetate substrate molar ratios. The model uses stoichiometric relationships to predict the moles of n-caprylate and the amount of ATP that would be produced based on the moles of ethanol and acetate provided to the system. The boundary for the metabolic flux in the model was set to 10 moles of carbon moieties consumed. In our model, moles of ethanol is set to "a" and therefore, the moles of acetate is 10-a. For the purpose of this model, the moles of n-butyrate and n-caproate formed were also fixed, as variables "b" and "c".

In our model, the stoichiometry of all metabolites (i.e., ethanol, acetate, n-butyrate, n-caproate, and n-caprylate, molecular hydrogen, water, intermediary metabolites, redox mediators, and ATP) depends on the variables "a", "b", and "c". The stoichiometry for re-oxidation of reduced ferredoxin via H2-ase or Rnf and ATP synthase varies depending on these variables, which determines the molecular hydrogen production and ATP production, respectively. Based on this stoichiometry, as well as the ethanol and carboxylate concentrations measured in the bioreactor, the Gibbs free energy of the reaction is calculated as well as the Gibbs free energy required for ATP formation. If the Gibbs free energy of the reaction was more negative than the Gibbs free energy required for ATP formation, the reaction was deemed feasible. For the purpose of these calculations the standard Gibbs free energies were taken from Kleerebezem and van Loosdrecht.

TABLE 5

Operating data for later periods for the bioreactor. Average hydraulic retention time (HRT), influent ethanol and acetate concentration, substrate molar ratios (ethanol-to-acetate), and organic loading rates (OLR) per period are reported as mean ± s.e.

| Period | Days | HRT | Substrate Molar Ratio | Ethanol mM | Acetate (mM) | OLR (g COD $L^{-1}$ $d^{-1}$) |
|---|---|---|---|---|---|---|
| Period 8 | 291 to 337 | 1.14 ± 0.04 | 3.38 ± 0.35 | 218.15 ± 9.68 | 64.64 ± 6.1 | 23.46 ± 1.16 |
| Period 9 | 337 to 358 | 1.2 ± 0.04 | 4.35 ± 0.35 | 245.15 ± 11.92 | 56.39 ± 3.55 | 24 ± 1.31 |
| Period 10 | 358 to 370 | 1.14 ± 0.04 | 4 | 220.82 ± 17.14 | NA | 24 |
| Period 11 | 370 to 397 | 1.12 ± 0.05 | 90.14 ± 12.08 | 286.51 ± 6.08 | 3.18 ± 0.42 | 26.22 ± 1.35 |

TABLE 6

Specificities per period (n-butyrate, n-caproate, or n-caprylate Production vs. total production of these carboxylates) and C8 to C6 ratio

| Period | Substrate Molar Ratio | C8 to C6 Ratio | Specificity (%) | | |
|---|---|---|---|---|---|
| | | | N-Butyrate | N-Caproate | N-Caprylate |
| Period 1 | 7.8 ± 0.65 | 3.04 + 0.32 | 3.57 + 0.4 | 23.85 + 2.05 | 72.57 + 8.2 |
| Period 2 | 183.29 ± 38.86 | 5.92 + 0.74 | 4.21 + 0.98 | 13.85 + 1.57 | 81.94 + 10.17 |
| Period 3 | 11.29 ± 1.38 | 1.95 + 0.42 | 3.7 + 0.91 | 32.64 + 5.45 | 63.66 + 14.03 |
| Period 4 | 4.45 ± 0.29 | 0.67 + 0.07 | 14.2 + 1.54 | 51.34 + 3.33 | 34.47 + 3.61 |
| Period 5 | 2.43 ± 0.17 | 0.63 + 0.16 | 33.38 + 3.81 | 40.97 + 6.41 | 25.65 + 5.96 |
| Period 6 | 1.93 ± 0.08 | 0.66 + 0.13 | 40.51 + 3.89 | 35.8 + 4.5 | 23.69 + 4.31 |
| Period 7 | 1.22 ± 0.06 | NA | 97.18 | 1.67 | NA |
| Period 8 | 3.38 ± 0.35 | 1.23 + 0.23 | 64.44 + 3.71 | 15.93 + 1.75 | 19.62 + 3.12 |
| Period 9 | 4.35 ± 0.35 | 0.13 + 0.01 | 92.97 + 5.72 | 6.25 + 0.47 | 0.78 + 0.07 |
| Period 10 | 4 | 1 + 0.31 | 59.24 + 12.78 | 20.34 + 2.51 | 20.42 + 6.86 |
| Period 11 | 90.14 ± 12.08 | 0.46 + 0.22 | 56.09 + 7.56 | 29.99 + 6.41 | 13.92 + 6.14 |

TABLE 7

Average effluent concentrations (mM) in bioreactor per period (mean ± s.e.). nd if concentration was below detection limit (0.2 mM). If only one measurement was above detection limit, only that measurement is reported. Valerate, isocaproate, and heptanoate were not detected in the bioreactor during the Example.

| Period | Concentration in Effluent (mM) (mean ± s.e.) | | | | | | | |
|---|---|---|---|---|---|---|---|---|
| | Ethanol | Acetate | Propionate | Isobutyrate | N-Butyrate | Isovalerate | N-Caproate | N-Caprylate |
| P1 | 15.6 ± 1 | 5.1 ± 0.3 | nd | 0.4 ± 0 | 4.7 ± 0.4 | nd | 4.5 ± 0.2 | 1.5 ± 0.1 |
| P2 | 67.3 ± 8.8 | 4.1 ± 0.6 | nd | 0.4 ± 0 | 3.6 ± 0.9 | 0.4 | 2.9 ± 0.4 | 1.4 ± 0.1 |
| P3 | 88.3 ± 1.9 | 12.6 ± 1.5 | nd | nd | 2.5 ± 0.2 | nd | 2.8 ± 0.2 | 0.9 ± 0.1 |
| P4 | 49.7 ± 4.8 | 16 ± 1.5 | nd | 0.4 ± 0 | 9 ± 1.3 | nd | 2.5 ± 0.2 | 0.3 ± 0.1 |
| P5 | 48.5 ± 4.3 | 35.6 ± 2.2 | nd | 0.5 ± 0 | 18.1 ± 0.6 | nd | 0.9 ± 0.1 | nd |
| P6 | 54.8 ± 4 | 56.3 ± 4.9 | nd | nd | 20 ± 1.2 | nd | 0.5 ± 0 | nd |
| P7 | 49.7 ± 3.2 | 88.2 ± 8.4 | nd | 0.4 | 18.3 ± 0.9 | nd | 0.4 ± 0.0 | 0.2 |
| P8 | 58.5 ± 5.3 | 28.6 ± 5.4 | 0.5 ± 0 | 0.7 ± 0 | 28 ± 1.4 | nd | 0.5 ± 0 | 0.2 |

TABLE 8

Conversion efficiencies (individual carboxylate production rate divided by organic loading rate) for n-butyrate, n-caproate, n-caprylate, and the combined medium chain carboxylic acids (MCCA; includes n-caproate and n-caprylate) per period.

| Period | Substrate Molar Ratio | Conversion Efficiency (%) | | | |
|---|---|---|---|---|---|
| | | N-Butyrate | N-Caproate | N-Caprylate | MCCA |
| P1 | 7.8 ± 0.65 | 3.36 ± 0.33 | 22.46 ± 1.55 | 68.34 ± 6.87 | 90.8 ± 7.44 |
| P2 | 183.29 ± 38.86 | 2.21 ± 0.49 | 7.29 ± 0.67 | 43.11 ± 4.52 | 50.4 ± 4.7 |
| P3 | 11.29 ± 1.38 | 2.24 ± 0.5 | 19.75 ± 2.53 | 38.53 ± 7.42 | 58.28 ± 8.19 |
| P4 | 4.45 ± 0.29 | 9.75 ± 1.06 | 35.25 ± 2.3 | 23.67 ± 2.49 | 58.92 ± 3.84 |
| P5 | 2.43 ± 0.17 | 23.36 ± 2.15 | 28.67 ± 4.05 | 17.95 ± 3.99 | 46.62 ± 5.88 |
| P6 | 1.93 ± 0.08 | 32.65 ± 2.76 | 28.85 ± 3.38 | 19.09 ± 3.36 | 47.95 ± 4.99 |
| P7 | 1.22 ± 0.06 | 21.38 ± 3.52 | 0.37 ± 0.02 | 0.25 ± NA | 0.62 ± NA |
| P8 | 3.38 ± 0.35 | 35.5 ± 2.23 | 8.78 ± 0.99 | 10.81 ± 1.74 | 19.59 ± 2.11 |
| P9 | 4.35 ± 0.35 | 33.24 ± 2.35 | 2.23 ± 0.19 | 0.28 ± 0.03 | 2.51 ± 0.2 |
| P10 | 4 | 47.6 ± NaN | 16.34 ± NaN | 16.41 ± NaN | 32.74 ± NaN |
| P11 | 90.14 ± 12.08 | 18.53 ± 1.97 | 9.91 ± 1.95 | 4.6 ± 1.99 | 14.51 ± 2.83 |

TABLE 9

Production rates of n-butyrate, n-caproate, and n-caprylate. Total production rate is sum of effluent and transfer rate. C8 to C6 production ratio is also reported. In Period 7 transfer rate for both n-caproate and n-caprylate was negative based on stripping data so set to zero. N-Caprylate effluent measurement only had one value. Therefore could not calculate C8 to C6 ratio. In P9 stripping was off.

| Period | N-Butyrate Production (g COD/L/d) | | | N-Caproate Production g COD/L/d | | | N-Caprylate Production Rate (g COD/L/d) | | |
|---|---|---|---|---|---|---|---|---|---|
| | Effluent Rate | Transfer Rate | Total Rate | Effluent Rate | Transfer Rate | Total Rate | Effluent Rate | Transfer Rate | Total Rate |
| P1 | 0.63 ± 0.06 | NA | 0.63 ± 0.06 | 0.96 ± 0.04 | 3.25 ± 0.22 | 4.21 ± 0.23 | 0.44 ± 0.02 | 12.36 ± 1.16 | 12.8 ± 1.16 |
| P2 | 0.49 ± 0.12 | 0.07 ± 0.03 | 0.56 ± 0.12 | 0.64 ± 0.1 | 1.19 ± 0.11 | 1.83 ± 0.15 | 0.41 ± 0.02 | 10.43 ± 1.03 | 10.84 ± 1.03 |
| P3 | 0.31 ± 0.03 | 0.22 ± 0.11 | 0.53 ± 0.11 | 0.57 ± 0.05 | 4.15 ± 0.53 | 4.72 ± 0.54 | 0.25 ± 0.03 | 8.95 ± 1.69 | 9.2 ± 1.69 |
| P4 | 1.24 ± 0.18 | 1.51 ± 0.21 | 2.75 ± 0.27 | 0.55 ± 0.05 | 9.38 ± 0.48 | 9.93 ± 0.48 | 0.1 ± 0.04 | 6.57 ± 0.64 | 6.67 ± 0.64 |
| P5 | 2.46 ± 0.11 | 3.42 ± 0.45 | 5.88 ± 0.47 | 0.2 ± 0.02 | 7.03 ± 0.96 | 7.22 ± 0.96 | NA | 4.52 ± 0.98 | 4.52 ± 0.98 |
| P6 | 2.67 ± 0.19 | 5.37 ± 0.55 | 8.04 ± 0.58 | 0.11 ± 0.01 | 7 ± 0.77 | 7.11 ± 0.77 | NA | 4.7 ± 0.8 | 4.7 ± 0.8 |
| P7 | 2.44 ± 0.14 | 2.55 ± 0.79 | 4.99 ± 0.8 | 0.09 ± 0 | 0 | 0.09 ± 0 | 0.06 | 0 | 0.06 |
| P8 | 3.94 ± 0.24 | 4.39 ± 0.22 | 8.33 ± 0.32 | 0.12 ± 0.01 | 1.94 ± 0.21 | 2.06 ± 0.21 | 0.06 ± NA | 2.47 ± 0.39 | 2.54 ± 0.39 |
| P9 | 7.98 ± 0.36 | NA | 7.98 ± 0.36 | 0.54 ± 0.03 | NA | 0.54 ± 0.03 | 0.07 ± 0.01 | NA | 0.07 ± 0.01 |
| P10 | 4.38 ± 0.36 | 7.04 ± 1.99 | 11.42 ± 2.02 | 0.06 ± 0 | 3.86 ± 0.04 | 3.92 ± 0.04 | NA | 3.94 ± 1.23 | 3.94 ± 1.23 |
| P11 | 1.23 ± 0.08 | 3.63 ± 0.44 | 4.86 ± 0.45 | 0.14 ± 0.04 | 2.46 ± 0.49 | 2.6 ± 0.49 | 0.08 ± 0 | 1.13 ± 0.52 | 1.21 ± 0.52 |

TABLE 10

Extraction efficiencies per period (mean and s.e.) Extraction system was off for P9.

| Period | Average Extraction Efficiency (%) | | |
|---|---|---|---|
| | N-Butyrate | N-Caproate | N-Caprylate |
| P1 | NA | 77.25 + 6.71 | 96.6 + 12.63 |
| P2 | 11.75 + 5.61 | 65.18 + 7.93 | 96.23 + 13.23 |
| P3 | 41.6 + 22.62 | 87.98 + 15.07 | 97.27 + 25.55 |
| P4 | 54.86 + 9.25 | 94.46 + 6.6 | 98.5 + 13.38 |
| P5 | 58.13 + 8.97 | 97.28 + 18.56 | 100 + 30.72 |
| P6 | 66.77 + 8.36 | 98.49 + 15.23 | 100 + 24.12 |
| P7 | 51.02 + 17.84 | NA | NA |
| P8 | 52.67 + 3.38 | 94.24 + 13.91 | 97.53 + 21.39 |
| P9 | strip off | strip off | strip off |
| P10 | 61.65 + 20.59 | 98.53 + 1.46 | 100 + 44.19 |
| P11 | 74.63 + 11.48 | 94.73 + 26.15 | 93.71 + 58.95 |

TABLE 11

Alpha Diversity Metrics; bottom and middle of bioreactor; max depth 12940 sequences per sample; 10 rarefactions.

| Bioreactor Position | Gini Coefficient | Observed OTUs | Shannon Diversity |
|---|---|---|---|
| Bottom | 0.969 ± 0.004 | 162 ± 14 | 4.603 ± 0.288 |
| Middle | 0.975 ± 0.006 | 159 ± 18 | 3.942 ± 0.560 |

TABLE 12

Gas Production Rate per period (for the main periods in the Example only an average rate across all periods is reported; P1 is not included because data was not available)

| Period | Gas Production Rate (mL d$^{-1}$) |
|---|---|
| Main (P2 to P7) | 0.38 ± 0.01 |
| P8 | 1.22 ± 0.06 |
| P9 | 1.19 ± 0.03 |
| P10 | 1.66 ± 0.27 |
| P11 | 2.74 ± 0.04 |

Although the present disclosure has been described with respect to one or more particular embodiments and/or examples, it will be understood that other embodiments and/or examples of the present disclosure may be made without departing from the scope of the present disclosure.

The invention claimed is:

1. A method for producing a product composition comprising n-caprylic acid and/or n-caprylate, with a C8 to C6 ratio higher than 1:1, comprising:
   a) providing a reaction medium comprising a microbiome comprising a plurality of chain-elongating bacteria and having a pH of 5-7.5;
   b) adding a substrate comprising ethanol or a mixture of ethanol and acetate; and
   c) holding the reaction medium at a temperature of 15° C. to 45° C. during an acclimation phase until the reaction mixture produces a desired amount of n-caprylic acid or n-caprylate;
   d) continuously removing at least a portion or all of the n-caprylic acid or n-caprylate formed in the reaction medium during the acclimation phase, wherein the reaction medium is maintained at a pH of 5-7.5 during c) and, optionally, d); and
   e) continuously removing during a production phase at least a portion or all of the n-caprylic acid or n-caprylate formed in the reaction medium to form the product composition, wherein the plurality of chain elongating bacteria comprises Rhodocyclaceae K82 spp, *Arcobacter* sup., *Burkholderia* spp., *Oscillospira* spp., *Anaerofilum* spp., *Desulfosporosinus meridiei*, *Methanobacterium* spp., *Lactobacillus* spp., *Dsygonomonas* spp., *Prevotella* spp., *Bacteroides* spp., *Desulfovivrio* spp., *Caloramator* spp., *Acinetobactor* spp., or a combination thereof.

2. The method of claim 1, wherein additional substrate is added during the acclimation phase and/or during the production phase.

3. The method of claim 1, wherein the substrate is ethanol.

4. The method of claim 1, wherein the substrate is a mixture of ethanol and acetate.

5. The method of claim 4, wherein the ethanol and acetate molar ratio is 4.5 or greater.

6. The method of claim 4, wherein the ethanol and acetate molar ratio is 10 or greater.

7. The method of claim 1, further comprising a selection period that is carried out as part of the acclimation phase, subsequent to the acclimation phase, or as part of the production phase, wherein during the selection period no n-caprylic acid or n-caprylate is removed from the reaction mixture.

8. The method of claim 1, further comprising a selection period that is carried out as part of the acclimation phase, subsequent to the acclimation phase, or as part of the production phase, wherein during the selection period the concentration of n-caprylic acid and/or n-caprylate in the reaction mixture is greater than 0.1 g/COD/L.

9. The method of claim 1, further comprising a selection period that is carried out as part of the production phase, subsequent to the acclimation phase, or as part of the production phase, wherein during the selection period no n-caprylic acid or n-caprylate is removed from the reaction mixture.

10. The method of claim 1, further comprising a selection period that is carried out as part of the production phase, subsequent to the acclimation phase, or as part of the production phase, wherein during the selection period the concentration of n-caprylic acid and/or n-caprylate in the reaction mixture is greater than 0.1 g COD/L.

11. The method of claim 1, wherein the reaction mixture is under ambient pressure.

12. The method of claim 1, wherein the reaction mixture is present in an anaerobic environment.

13. The method of claim 1, wherein after the acclimation phase the reaction mixture produces n-caprylate corresponding to at least 1 g chemical oxygen demand (COD)/L-d.

14. The method of claim 1, wherein during the production phase the reaction mixture has a product ratio of n-caprylate to n-caproate of at least 10 g COD/g COD.

15. The method of claim 1, wherein the product composition comprises at least 50% n-caprylic acid and/or n-caprylate by weight based on the total amount of product compounds in the product composition.

16. The method of claim 1, wherein the pH is 6.5-7.

17. The method of claim 1, wherein after the acclimation phase at least 0.01% by weight caprylic acid is produced by the reaction medium based on the total weight of the reaction medium.

18. The method of claim 1, wherein the product composition comprises less than 20%, by weight caproate products based on the weight of all of the product compounds in the product composition.

19. The method of claim 1, further comprising extracting the product composition from the reaction mixture using a solvent or mixture of solvents wherein the product composition comprises 50% or greater by weight of the n-caprylic acid and/or n-caprylate.

* * * * *